US006982153B1

(12) United States Patent
Pelletier et al.

(10) Patent No.: US 6,982,153 B1
(45) Date of Patent: Jan. 3, 2006

(54) **DNA SEQUENCES FROM *STAPHYLOCOCCUS AUREUS* BACTERIOPHAGE 77 THAT ENCODE ANTI-MICROBIAL POLYPEPTIDES**

(75) Inventors: Jerry Pelletier, Baie-d'Urfe (CA); Philippe Gros, St. Lambert (CA); Michael DuBow, Montreal (CA)

(73) Assignee: Targanta Therapeutics, Inc., St. Laurent (CA)

( * ) Notice: Subject to any disclaimer, the term of this patent is extended or adjusted under 35 U.S.C. 154(b) by 0 days.

(21) Appl. No.: 09/407,804

(22) Filed: Sep. 28, 1999

Related U.S. Application Data

(60) Provisional application No. 60/110,992, filed on Dec. 3, 1998.

(51) Int. Cl.
 *C12P 21/02* (2006.01)
 *C07H 21/04* (2006.01)
(52) U.S. Cl. .............. 435/69.1; 435/252.3; 435/254.11; 435/320.1; 536/23.72
(58) Field of Classification Search ............... 536/23.1, 536/23.7, 24.1; 435/320.1, 252.3, 325, 69.1, 435/254.11, 23.72
 See application file for complete search history.

(56) References Cited

U.S. PATENT DOCUMENTS

| 3,691,016 A | 9/1972 | Patel ........................... 435/181 |
| 3,969,287 A | 7/1976 | Jaworek et al. ................. 260/8 |
| 4,195,128 A | 3/1980 | Hildebrand et al. ........ 435/178 |
| 4,229,537 A | 10/1980 | Hodgins et al. ............. 435/177 |
| 4,247,642 A | 1/1981 | Hirohara ...................... 435/178 |
| 4,330,440 A | 5/1982 | Ayers et al. ............. 525/54.31 |
| 6,737,248 B2 * | 5/2004 | Kunsch et al. .............. 435/69.1 |

FOREIGN PATENT DOCUMENTS

| EP | 0 072 925 A2 | 3/1983 |
| EP | 0 748 871 A1 | 12/1996 |
| EP | 0 786 519 A2 | 7/1997 |
| WO | WO 89/00199 | 1/1989 |
| WO | WO 95/27043 | 10/1995 |
| WO | WO 97/23599 A2 * | 7/1997 |

OTHER PUBLICATIONS

Black et al. "DNA encoding a *Staphylococcus aureus* protein" Aug. 21, 1997, Database N_Geneseq_1101, Accession No.: AAT83989.*
Kaneko et al., "Panton-Valentine Leukocidin Genes in a Phage-like Particle Isolated from Mitomycin C-Treated *Staphylococcus aureus* V8 (ATCC 49775)," Biosci. Biotech. Biochem., 61(11) 1960-1962, 1997.*
Sequence alignments for SEQ ID Nos: 4-7 and 9.*
Adelman et al., "In Vitro Deletional Mutagenesis For Bacterial Production Of The 20,000-Dalton Form Of Human Pituitary Growth Hormone", DNA, 2(3):183-93, 1983.

Altschul et al., "Gapped BLAST and PSI-BLAST: a new generation of protein database search programs", Nucleic Acids Research, 1997, vol. 25, No. 17, pp. 3389-3402.
Cohen, "Epidemiology of Drug Resistance: Implications for a Post-Antimicrobial Era", ML Science, vol. 257, Aug. 21, 1992, pp. 1050-1055.
Diaz et al., "Construction of a broad-host-range pneumococcal promoter-probe plasmid", Gene, 90:163-167, 1990.
Durfee et al., "The retinoblastoma protein associates with the protein phosphatase type 1 catalytic subunit", Genes & Development, 7:555-569, 1993.
Eichenbaum et al., "Use of Lactococcal nisA Promoter To Regulate Gene Expression in Gram-Positive Bacteria: Comparison of Induction Level and Promoter Strength", Applied and Environmental Microbiology, 64:2763-2769, 1998.
Endo et al., "A new protein containing an SH2 domain that inhibits JAK kinases", Nature, 387:921-924, 1997.
Field et al., "Purifications Of A RAS-Responsive Adenylyl Cyclase Complex From *Saccharomyces cerevisiae* By Use Of An Epitope Addition Method", Mol. Cell. Biol., 8:2159-2165, 1988.
Fink, "Where are the Limits of Life?", Book Reviews, 322:469-470, 1998.
Garvey et al., "The complete sequence of *Bacillus* phage Ø29 gene 16: a protein required for the genome encapsidation reaction", Gene, 40:311-316, 1985.
Gutierrez et al., "Signals in the Ø29 DNA-Terminal Protein Template for the Initiation of Phage Ø29 DNA Replication", Virology, 155:474-483, 1986.
Jorgensen et al., "Antimicrobial Resistance among Respiratory Isolates of *Haemophilus influenza, Moraxella catarrhalis*, and *Streptococcus pneumoniae* in the United States", Antimicrobial Agents and Chemotherapy, 34:2075-2080, 1990.
Kaneko et al., "Complete nucleotide sequence and molecular characterization of the temperate staphylococcal bacteriophage φPVL carrying Pantom-Valentine leukocidin genes", Genes 215:57-67, 1998.
Karimova et al., "A bacterial two-hybrid system based on a reconstituted signal transduction pathway", Proc. Natl. Acad. Sci., 95:5752-5756, 1998.
Katagari et al., "Multiple Possible Sites of BRCA2 Interacting With DNA Repair Protein RAD5 1", Genes, Chromosomes & Cancer, 21:217-222, 1998.
Kreiswirth et al., "The Toxic Shock Syndrome Exotoxin Structural Gene Is Not Detectably Transmitted By A Prophage", Nature, Oct. 20-26;305(5936):709-12, 1983.

(Continued)

Primary Examiner—Robert A. Wax
(74) Attorney, Agent, or Firm—Sughrue Mion, PLLC

(57) ABSTRACT

The disclosure concerns particular bacteriophage open reading frame, and portions and products of those open reading frames which have antimicrobial activity. Methods of using such products are also described.

16 Claims, 15 Drawing Sheets

OTHER PUBLICATIONS

Kodaira et al., "The dnaX gene Encodes the DNA Polymerase III Holoenzyme τ Submit, the dnaZ Gene Product", Mol Gen Genet, 192:80-86, 1983.

Lee et al., "*Escherichia coli* DnaX product, the τ subunit of DNA polymerase III, is a multifunctional protein with single-stranded DNA-dependent ATPase activity", Proc. Natl. Acad. Sci., 84:2713-2717, 1987.

Loessner et al., "The Two-Component Lysis System Of *Staphylococcus aureus* Bacteriophage Twort: A Large TTG-Start Holin And An Associated Amidase Endolysin", FEMS Microbiol Lett., May 15;162(2):265-74, 1998.

Maki et al., "DNA Polymerase III Holoenzyme of *Escherichica coli*", The Journal of Biological Chemistry, 263:6547-6554, 1988.

Mancini et al., "Complementation of the fol2 Deletion in *Sccharmoyces cerevisiae* by Human and *Escherichia coli* Genes Encoding GTP Cyclohydrolase I", Biochemical and Biophysical Research Communications, 255:521-527, 1999.

Martin et al., "Analysis of the Complete Nucleotide Sequence and Functional Organization of the Genome of *Streptococcus pneumoniae* Bacteriophage Cp-1", Journal of Virology, 70:3678-3687, 1996.

McDonnell et al., ""Diplophage": A Bacteriophage of *Diplococcus pneumoniae*", Virology, 63:577-582, 1975.

Nardese et al., "Disruption of the GTP-Cyclohidrolase I Gene In *Saccharomyces cerevisiae*", Biochemical and Biophysical Research Communications, 218:273-279, 1996.

Neu, "The Crisis in Antibiotic Resistance", Science, 257: 1064-1073, 1992.

Oskouian et al., "Repression And Catabolite Repression Of The Lactose Operon of *Staphylococcus aureus*", J. Bacteriol, Jul., 172(7):3804-12, 1990.

Pickett et al., "Encapsidation of Heterologous RNAs by Bacteriophage MS2 Coat Protein", Nucleic Acids Research, 21:4621-4626, 1993.

Qin et al., "A Strategy for Rapid, High-Confidence Protein Identification", Anal. Chem., 69:3995-4001, 1997.

Qiu et al., "Dimerization by Translation Initiation Factor 2 Kinase GCN2 Is Mediated by Interactions in the C-Terminal Ribosome-Binding Region and the Protein Kinase Domain", Molecular and Cellular Biology, 18:2697-2711, 1998.

Reisinger et aJ., "Lambda Kil-Mediated Lysis Requirse the Phage Context", Virology, 193:1033-1036, 1993.

Rost et al., "Bridging The Protein Sequence-Structure Gap By Structure Predictions", Annu. Rev.Biophys, Biomol. Struct., 25:113-36, 1996.

Salamov et al., "Combining Sensitive Database Searches With Multiple Intermediates to Detect Distant Homologues", Protein Eng., 12:95-100, 1999.

Schenk et al., "Improved Method For Electroporation of *Staphylococcus aureus*", FEMS Microbiology Letters, 94: 133-138, 1992.

Sheehan et al., "The lytic enzyme of the pneumococcal phage Dp-1: a chimeric lysin of intergeneric origin", Molecular Microbiology, 25:717-725, 1997.

Smidt et al., "Physiologic Importance of Pyrroloquinoline Quinone", P.S.E.B.M., 197:19-26, 1991.

Sopta et al., "Isolation of Three Proteins That Bind to Mammalian RNA Polymerase II", 260:10353-10360, 1985.

Steiner et al., "The Missing Link in Phage Lysis of Gram-Positive Bacteria: Gene 14 of *Bacillus subtilis* Phage φ29 Encodes the Functional Homolog of Lambda S Protein", Journal of Bacteriology, 175:1038-1042, 1993.

Swanstrom et al., "Agar Layer Method for Production of High Titer Phage Stocks", Proc. Soc. Exptl. Biol. & Med., 78:372-375, 1951.

Tauriainen et al., "Recombinant Luminescent Bacterial for Measuring Bioavailable Arsenite and Antimonite", Applied and Environmental Microbiology, 63:4456-4461, 1997.

Tomasz, "Model for the Mechanism Controlling the Expression of Competent State in *Pneumococcus* Cultures", Journal of Bacteriology, 91:1050-1061, 1966.

Tsuchihashi et al., "Translational frameshifting generates the γ subunit of DNA polymerase III holoenzyme", Proc. Natl. Acad. Sci., 87:2516-2520, 1990.

Yoshikawa et al., "Nucleotide sequence analysis of DNA replication origins of the small *Bacillus* bacteriphages: evolutionary relationships", Gene, 1985.

* cited by examiner

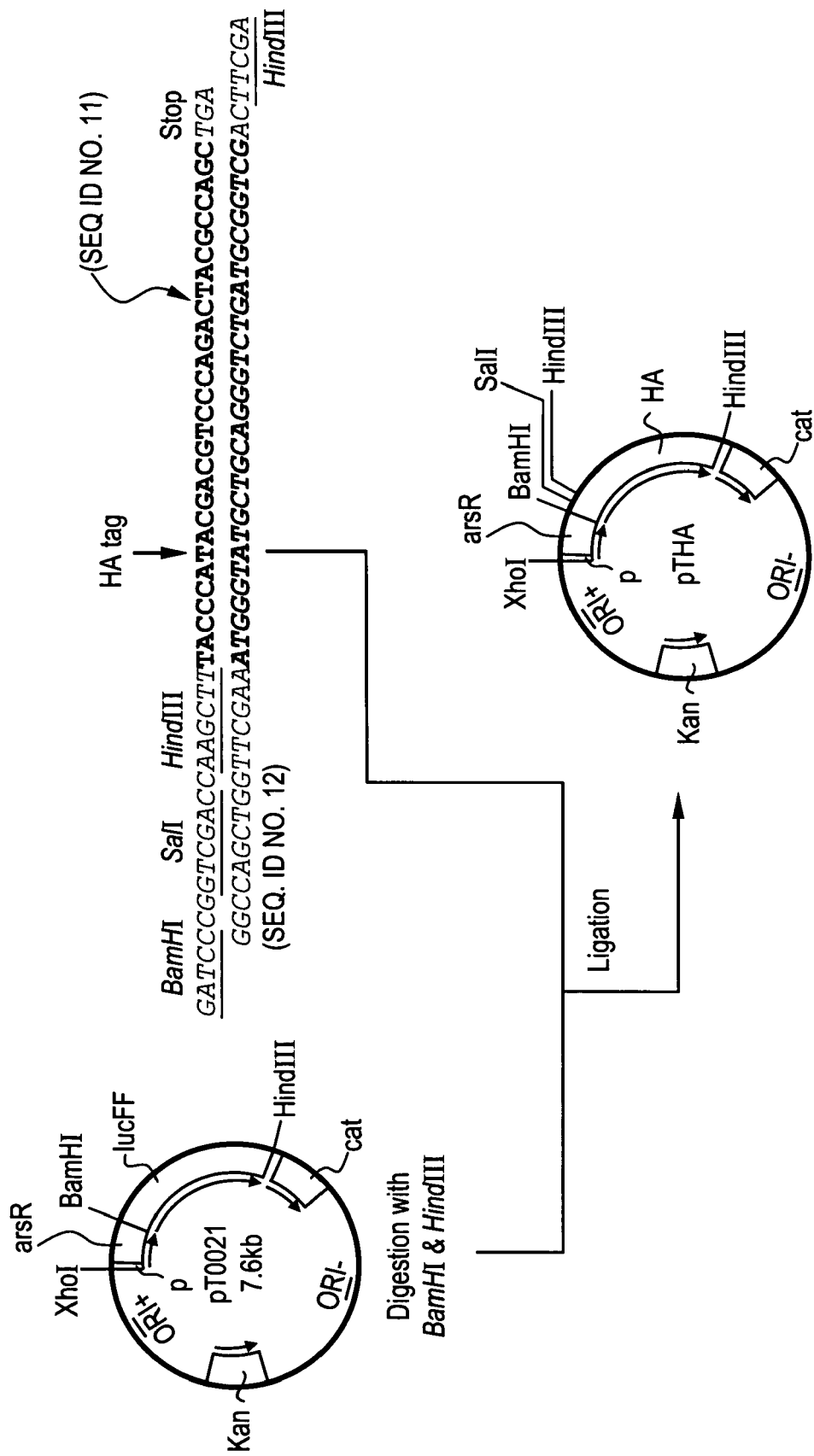

Functional assay on semi-solid support media

Functional assay in liquid medium

-                     5 μM

-                     5 μM

-             5 μM

-             5 μM

-             5 µM

-             5 µM

-                   5 μM

-                   5 μM

−

5 μM

—

5 μM

−

5 μM

−

5 μM

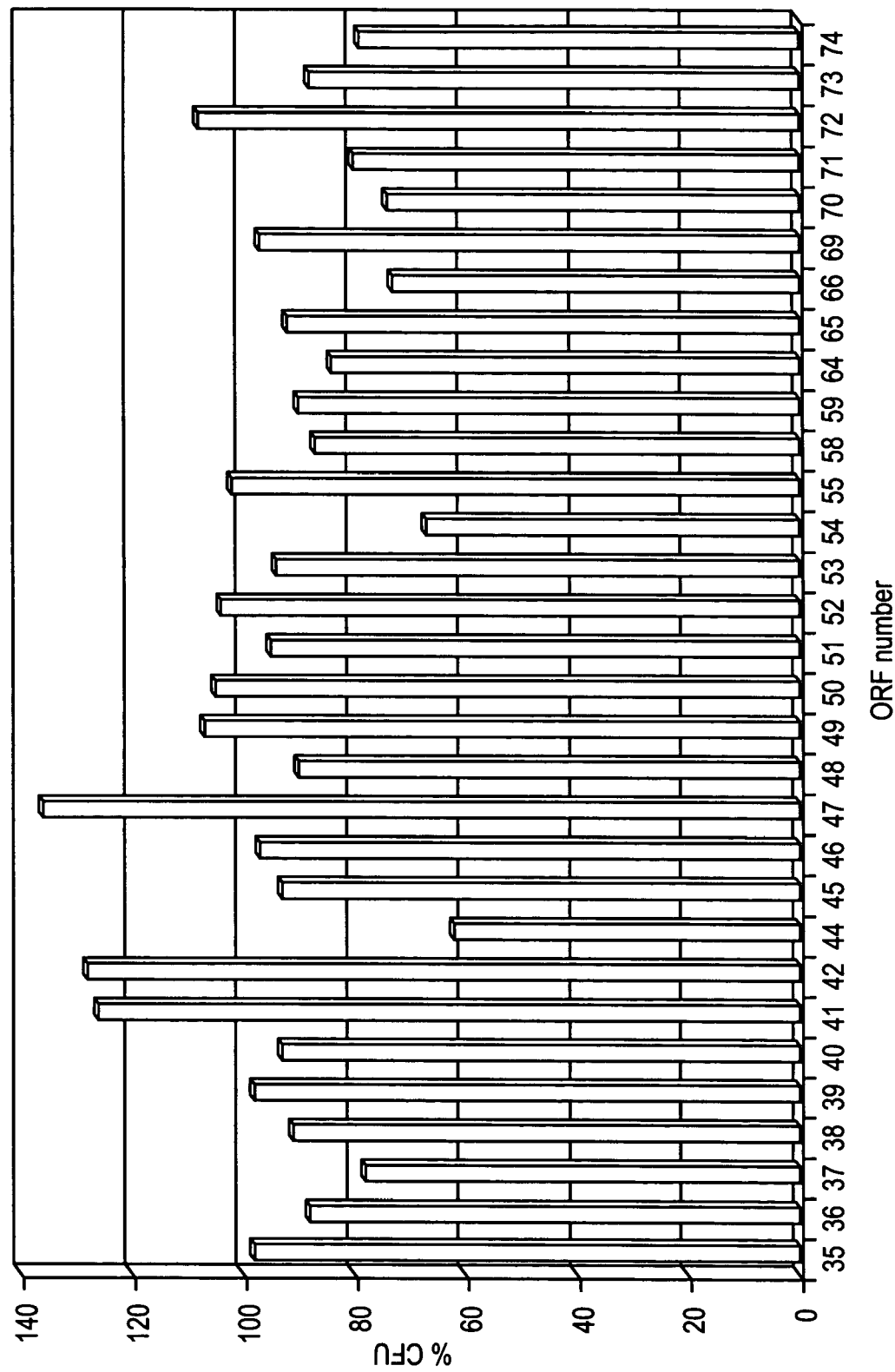

SEQUENCE LISTING

<160> NUMBER OF SEQ ID NOS: 29

<210> SEQ ID NO 1
<211> LENGTH: 10
<212> TYPE: DNA
<213> ORGANISM: Staphylococcus aureus bacteriophage 77

<400> SEQUENCE: 1
gcgtcgaccg                                                                  10

<210> SEQ ID NO 2
<211> LENGTH: 20
<212> TYPE: DNA
<213> ORGANISM: Staphylococcus aureus bacteriophage 77

<400> SEQUENCE: 2
tattatccaa aacttgaaca                                                       20

<210> SEQ ID NO 3
<211> LENGTH: 20
<212> TYPE: DNA
<213> ORGANISM: Staphylococcus aureus bacteriophage 77

<400> SEQUENCE: 3
cggtggtata tccagtgatt                                                       20

<210> SEQ ID NO 4
<211> LENGTH: 714
<212> TYPE: DNA
<213> ORGANISM: Staphylococcus aureus bacteriophage 77

<400> SEQUENCE: 4
atgacgcata atatagaaaa acgcattaat aaattaaaaa cttctggaaa tccaaaattt      60
aaaaagttag attcagatat tcactattta ctcaagagat ttgaaggtga aaaaaaccat     120
aaaggttttt atccaaagtt taaacaagga gaaatagttt ttgtagattt cggtataaac     180
gttaataaag aattttctaa ttcacacttt gcaatagtga tgaataaaaa tgattctaat     240

```
acggaggata tagtaaatgt tattccctta tcctctaaag aaaacaaaaa gtatttaaag     300
atgaattttg atttgaaatg ggagtattat ttaagattgt ttttaaattt aattagcgcg     360
caaaataatt cagctatatt aaagaagtt  ttcgataaaa ataccaaaa  aaacaacaca     420 gaattcatca ctaaagatta ttttattgaa tttatatctg atagtttaga aattgaaaat     480
aaattaaata aaattgacag aaacattaat aacatagtat cagcaattga taaggtaaaa     540
aaattaaaag gtaatagtta cgcttgcata aattctttcc agccgattag taagtttcgc     600
ataagaaaag ttttaccca  aaaaattaaa aatccagtaa tagattcttc ggatattatg     660
ttactgataa atagaattaa taataatata ttgcagatcc ctgatataag atga          714

<210> SEQ ID NO 5
<211> LENGTH: 651
<212> TYPE: DNA
<213> ORGANISM: Staphylococcus aureus bacteriophage 77

<400> SEQUENCE: 5
atgaacgagc aaataatagg aagcatatat actttagcag gaggtgttgt gctttattca     60
gttaaagaga ttttaggta  ttttacagat tctaacttac aacgtaaaaa atcaattta    120 gaacaaatat atccgatata tttagattgt tttaaaaagg ctaaaagat  gattggagct    180 tatattattc aacagaaca  gcatgaattt ttagattttt ttgatattga agtctttaat    240
aatttagata agcaaagtaa aaaagcgtat gaaaatgtta ttggatttag acaaatgatt    300
aatttatcaa atagagttaa ggcaatggaa gattttaaga tgagtttcaa caatgaattt    360
agtacaaatc agatttttt  taatccttct tttgttatgg aaacaattgc tattataaat    420
gaatatcaaa aagatatatc ttatttaaaa aatataatta ataaaatgaa tgaaaataga    480
gcttataatc atattgatag ttttatcact tcagagtacc gacgaaaaat aaacgattat    540
aatctttatc ttgataaatt tgaagaacag tttagtcaaa agtttaaaat aaacagaact    600
tcgataaaag aaagaattat tattaattta acaagagga  gatttaaatg a             651

<210> SEQ ID NO 6
<211> LENGTH: 261
<212> TYPE: DNA
<213> ORGANISM: Staphylococcus aureus bacteriophage 77

<400> SEQUENCE: 6
atgtattacg aaataggcga atcatacgc  aaaaatattc atgttaacgg attcgatttt     60
aagctattca ttttaaaagg tcatatgggc atatcaatac aagttaaaga tatgaacaac    120
gtaccaatta acatgctta  tgtcgtagat gagaatgact tagatatggc atcagactta    180
tttaaccaag caatagatga atggattgaa gagaacacag acgaacagga cagactaatt    240
aacttagtca tgaaatggta g                                              261

<210> SEQ ID NO 7
<211> LENGTH: 162
<212> TYPE: DNA
<213> ORGANISM: Staphylococcus aureus bacteriophage 77

<400> SEQUENCE: 7
atgagcaaca tttataaaag ctacctagta gcagtattat gcttcacagt cttagcgatt     60
gtacttatgc cgtttctata cttcactaca gcatggtcaa ttgcgggatt cgcaagtatc    120
gcaacattca tgtactacaa agaatgcttt ttcaaagaat aa                       162
```

<210> SEQ ID NO 8
<211> LENGTH: 159
<212> TYPE: DNA
<213> ORGANISM: Staphylococcus aureus bacteriophage 77

<400> SEQUENCE: 8

| | | | | | |
|---|---|---|---|---|---|
| atggtaacca | agaattttt | aaaaactaaa | cttgagtgtt | cagatatgta | cgctcagaaa | 60 |
| ctcatagatg | aggcacaggg | cgatgaaaat | aggttgtacg | acctatttat | ccaaaaactt | 120 |
| gcagaacgtc | atacacgccc | cgctatcgtc | gaatattaa | | | 159 |

<210> SEQ ID NO 9
<211> LENGTH: 297
<212> TYPE: DNA
<213> ORGANISM: Staphylococcus aureus bacteriophage 77

<400> SEQUENCE: 9

| | | | | | |
|---|---|---|---|---|---|
| atgttcaata | taaaacgaaa | aacggaggaa | gtcaagatgt | attacgaaat | aggcgaaatc | 60 |
| atacgcaaaa | atattcatgt | taacggattc | gattttaagc | tattcatttt | aaaaggtcat | 120 |
| atgggcatat | caatacaagt | taaagatatg | aacaacgtac | caattaaaca | tgcttatgtc | 180 |
| gtagatgaga | atgacttaga | tatggcatca | gacttattta | ccaagcaat | agatgaatgg | 240 |
| attgaagaga | acacagacga | acaggacaga | ctaattaact | tagtcatgaa | atggtag | 297 |

<210> SEQ ID NO 10
<211> LENGTH: 41708
<212> TYPE: DNA
<213> ORGANISM: Staphylococcus aureus bacteriophage 77

<400> SEQUENCE: 10

| | | | | | |
|---|---|---|---|---|---|
| gatcaaaata | cttggggaac | ggttagggag | taaacttcgc | gataattta | aaaattcatg | 60 |
| tataacccc | ctcttataac | cattttaagg | caggtgatga | atggagatt | atagtcgatg | 120 |
| aaaatttagt | gcttaaagaa | aaagaaaggc | tacaagtatt | atataaagac | atacctagca | 180 |
| ataaattaaa | agtagttgat | ggtttaatta | ttcaagcagc | aaggctacgt | gtaatgcttg | 240 |
| attacatgtg | ggaagacata | aaagaaaag | gtgattatga | tttatttact | caatctgaaa | 300 |
| aggcgccacc | atatgaaagg | gaaagaccag | tagccaaact | atttaatgct | agagatgctg | 360 |
| catatcaaaa | aataatcaaa | caattatcgg | atttattgcc | cgaagagaaa | gaagacacag | 420 |
| aaacgccatc | tgatgattac | ctatgattag | taataaatac | gttgatgaat | atataaattt | 480 |
| gtggaaacaa | ggaaagataa | ttttaaataa | agaaagaatt | gatctcttta | attatctaca | 540 |
| aaaacatata | tattcacgag | atgatgtata | ttttgatgaa | cagaaaatcg | aggattgtat | 600 |
| caaatttatt | gaaaaatggt | attttccaac | attaccattt | caaaggttta | tcatagctaa | 660 |
| tatatttctt | atagataaaa | atacagatga | agctttcttt | acagaatttg | ctattttcat | 720 |
| gggacgtgga | ggcgggaaaa | acggtctaat | aagtgctatt | agtgattttc | tttctacgcc | 780 |
| cttacacgga | gttaaagaat | atcacatctc | cattgttgct | aatagtgaag | atcaagcaaa | 840 |
| aacatcgttt | tgatgaaatca | gaccgttttt | aatggataac | aaacgaaata | agacgggtaa | 900 |
| aacgccaaaa | gctccttatg | aagttagtaa | agcaaaaata | ataaaccgtg | caactaaatc | 960 |
| ggttattcga | tataacacat | caaacacaaa | aaccaaagac | ggtggacgtg | aggggtgtgt | 1020 |
| tattttgat | gaaattcatt | atttctttgg | tcctgaaatg | gtaaacgtca | aacgtggtgg | 1080 |
| attaggtaaa | aagaaaaata | gaagaacgtt | ttatataagt | actgatggtt | ttgttagaga | 1140 |
| gggttatatc | gatgcaatga | agcacaaaat | tgcaagtgta | ttaagtggca | aggttaaaaa | 1200 |

-continued

```
tagtagattg tttgcttttt attgtaagtt agacgatcca aaagaagttg atgacagaca    1260
gacgtgggaa aaggcgaacc caatgttaca taaaccgtta tcagaatacg ctaaaacact    1320
gctaagcacg attgaagaag aatataacga tttaccattc aaccgttcaa ataagcccga    1380
attcatgact aagcgaatga atttgcctga agttgacctt gaaaaagtaa tagcaccatg    1440
gaaagaaata ctagcgacta atagagagat accaaattta gataatcaaa tgtgtattgg    1500
tggtttagac tttgcaaaca ttcgagattt tgcaagtgta gggctattat tccgaaaaaa    1560
cgatgattac atttggttag gacattcgtt tgtaagacaa gggttttttgg atgatgtcaa    1620
attagaacct cctattaaag aatgggaaaa aatgggatta ttgaccattg tcgatgatga    1680
tgtcattgaa attgaatata tagttgattg gttttttaaag gctagagaaa aatatgggct    1740
tgaaaaagtc atagctgata attatagaac tgatattgta agacgtgcgt ttgaggatgc    1800
tggcataaaa cttgaagtac ttagaaatcc aaaagcaata catggattac ttgcaccacg    1860
tatcgataca atgtttgcga aacataacgt aatatatgga gacaatcctt tgatgcgttg    1920
gtttactaat aatgttgctg taaaaatcaa gccggatgga aataaagagt atatcaaaaa    1980
agatgaagtc agacgtaaaa cggatggatt catggctttt gttcacgcat tatatagagc    2040
agacgatata gtagacaaag acatgtctaa agcgcttgat gcattaatga gtatagattt    2100
ctaatagagg aggtgagaca tgagtattct agaaaagata tttaaaacta ggaaagatat    2160
aacatatatg cttgatttag atatgataga agatctatca caacaagcgt atgtgaaacg    2220
tttagcgatt gatagttgta ttgaatttgt tgcgcgagct gtcgctcaaa gtcattttaa    2280
agtattggaa ggtaatagaa ttcaaaagaa tgatgtttac tacaagttaa atataaaacc    2340
aaatactgac ttatcaagcg atagtttttg gcaacaagtt atatataaac taatttatga    2400
taacgaggtt ttaatcgtag taagtgacag caaagaatta cttatcgcag atagctttta    2460
cagagaagag tacgctttgt atgatgatat attcaaagat gtaacggtta aagattatac    2520
ttatcaacgt actttcacaa tgcaagaggt catatattta aagtacaaca acaataaagt    2580
gacacacttt gtagaaagtc tattcgaaga ttacgggaaa atattcggaa gaatgatagg    2640
tgcacaatta aaaaactatc aaataagagg gattttgaaa tctgcctcta gcgcatatga    2700
cgaaaagaat atagaaaaat tacaagcgtt cacaaataaa ttattcaata ctttttaataa    2760
aaatcaacta gcaatcgcgc ctttgataga aggttttgat tatgaggaat tatctaatgg    2820
tggtaagaat agtaacatgc cttttttctga attgagtgag ctaatgagag atgcaataaa    2880
aaatgttgcg ttgatgattg gtataccctcc aggttttgatt tacggagaaa cagctgattt    2940
ggaaaaaaac acgcttgtat ttgagaagtt ctgtttaaca cctttattaa aaaagattca    3000
gaacgaatta aacgcgaaac tcataacaca aagcatgtat ttgaaagata caagaataga    3060
aattgtcggt gtgaataaaa aagacccact tcaatatgct gaagcaattg acaaacttgt    3120
aagttctggt tcatttacaa ggaatgaggt gcggattatg ttaggtgaag aaccatcaga    3180
caatcctgaa ttagacgaat acctgattac taaaaactac gaaaaagcta acagtggtga    3240
aaatgatgaa aagaaaaag atgaaaacac tttgaaaggt ggtgatgaag atgaaagcgg    3300
agattaaagg cgtcatcgtt tccaacgaag ataaatgggt ttacgaaatg cttggtatgg    3360
attcgacttg tcctaaagat gttttaacac aactagaatt tagtgatgaa gatgttgata    3420
ttataattaa ctcaaatggt ggtaacctag tagctggtag tgaaatatat acacatttaa    3480
gagctcataa aggcaaagtg aatgttcgta tcacagcaat agcagcaagt gcggcatcgc    3540
ttatcgcaat ggctggtgac cacatcgaaa tgagtccggt tgctagaatg atgattcaca    3600
```

-continued

| | |
|---|---|
| atccttcaag tattgcgcaa ggagaagtga aagatctaaa tcatgctgca gaaacattag | 3660 |
| aacatgttgg tcaaataatg gctgaggcat atgcggttag agctggtaaa aacaaacaag | 3720 |
| aacttataga aatgatggct aaggaaacgt ggctaaatgc tgatgaagcc attgaacaag | 3780 |
| gttttgcgga tagtaaaatg tttgaaaacg acaatatgca aattgtagca agcgatacac | 3840 |
| aagtgttatc gaaagatgta ttaaatcgtg taacagcttt ggtaagtaaa acgccagagg | 3900 |
| ttaacattga tattgacgca atagcaaata aagtaattga aaaataaat atgaaagaaa | 3960 |
| aggaatcaga aatcgatgtt gcagatagta aattatcagc aaatggattt tcaagattcc | 4020 |
| tttttaata caaaaatagg aggtcataaa atgactataa atttatcgga aacattcgca | 4080 |
| aatgcgaaaa acgaatttat taatgcagta acaacggtg aaccgcaaga aagacaaaat | 4140 |
| gaattgtacg gtgacatgat taaccaacta tttgaagaaa ctaaattaca agcaaaagca | 4200 |
| gaagctgaaa gagtttctag tttacctaaa tcagcacaaa cttgagtgc aaaccaaaga | 4260 |
| aatttcttta tggatatcaa taagagtgtt ggatataaag aagaaaaact tttaccagaa | 4320 |
| gaaacaattg atagaatctt cgaagattta acaacgaatc atccattatt agctgactta | 4380 |
| ggtattaaaa atgctggttt gcgtttgaag ttcttaaaat ccgaaacttc tggcgtggct | 4440 |
| gtttggggta aaatctatgg tgaaattaaa ggtcaattag atgctgcgtt cagtgaagaa | 4500 |
| acagcaattc aaaataaatt gacagcgttt gttgttttac aaaagatttt aaatgatttt | 4560 |
| ggtcctgcgt ggattgaaag atttgttcgt gttcaaatcg aagaagcatt tgcagtggcg | 4620 |
| cttgaaactg cgttcttaaa aggtactggt aaagaccaac cgattggctt aaaccgtcaa | 4680 |
| gtacaaaaag gtgtatcggt aactgatggt gcttatccag agaaagaaga acaaggtacg | 4740 |
| cttacatttg ctaatccgcg cgctacggtt aatgaattga cgcaagtgtt taaataccac | 4800 |
| tcaactaacg agaaaggtaa atcagtagcg gttaaaggta atgtaacaat ggttgttaat | 4860 |
| ccgtccgatg cttttgaggt tcaagcacag tatacacatt taaatgcaaa tggcgtatat | 4920 |
| gttactgctt taccatttaa tttgaatgtt attgagtcta cagttcaaga agcaggtaag | 4980 |
| gttttaacgt acgttaaagg tctatatgat ggttatttag ctggtggtat taatgttcag | 5040 |
| aaatttaaag aaacacttgc gttagatgat atggatttat acactgcaaa acaatttgct | 5100 |
| tacggcaaag cgaaagataa taagttgct gctgtttgga attagattt aaaaggacat | 5160 |
| aaaccagctt tagaagatac cgaagaaaca ctataaaatt ttatgaggtg ataaaatggt | 5220 |
| gaaatttaaa gttgttagag aatttaaaga catagagcac aatcaacaca gtacaaagt | 5280 |
| aggggagttg tatccagctg aagggtataa caatcctcgt gttgaattgt tgacaaatca | 5340 |
| aatcaaaaat aagtacgaca aagtttatat cgtaccttta gataagctga caaaacaaga | 5400 |
| attattagaa ctatgcgaat cattacaaaa aaaagcgtct agttcaatgg ttaaaagtga | 5460 |
| aatcatcgac ttattgaatg gtgaagacaa tgacgattga tgatttgctt gtcaaattta | 5520 |
| aatcacttga aaagattgac cataattcag aggatgagta cttaaagcag ttgttaaaaa | 5580 |
| tgtcgtacga gcgtataaaa aatcagtgcg gagttttga attagagaat ttaataggtc | 5640 |
| aagaattgat acttatacgc gctagatatg cttatcaaga tttattagaa cacttcaacg | 5700 |
| acaattacag acctgaaata atagattttt cgttatctct aatggaggta tcagaagatg | 5760 |
| aagaaagtgt ttaagaaacc tagaattaca actaaacgtt taaatacgcg tgttcatttt | 5820 |
| tataagtata ctgaaaataa tggtccagaa gctggagaaa aagaagaaaa attattatat | 5880 |
| agctgttggg cgagtattga tggtgtctgg ttacgtgaat tagaacaagc tatctcaaac | 5940 |

```
ggaacgcaaa atgacattaa attgtatatt cgtgatccgc aaggtgatta tttacccagt    6000
gaagaacatt atcttgaaat tgaatcaaga tatttcaaaa atcgtttgaa tataaagcaa    6060
gtatcaccag atttggataa taaagacttt attatgattc gcggaggata tagttcatga    6120
gtgtgaaagt gacaggtgat aaagcattag aaagagaatt agaaaaacat tttggcataa    6180
aagagatggt aaaagttcaa gataaggcgt taatagctgg tgctaaggta attgttgaag    6240
aaataaaaaa acaactcaaa ccttcagaag actcaggagc actgattagt gagattggtc    6300
gtactgaacc tgaatggata aaggggaaac gtactgttac aattaggtgg cgtgggcctt    6360
ttgaacgatt tagaatagta catttaattg aaaatggtca tgttgagaaa aagtcaggaa    6420
aatttgtaaa acctaaagct atgggtggga ttaatagagc aataagacaa gggcaaaata    6480
agtattttga gacgctaaaa agggagttga aaaaattgtg attgatattt tgtacaaagt    6540
tcatgaagtg attagtcaag acagaattat tagagagcac gtaaatatca ataatattaa    6600
gttcaataaa taccctaatg taaaagatac tgatgtacct tttattgtta ttgacgatat    6660
cgacgaccca atacctacaa cttatactga cggagatgag tgtgcatata gttatattgt    6720
ccaaatagat gttttttgtta agtacaatga tgaatataat gcgagaatca taagaaataa    6780
gatatctaat cgcattcaaa agttattatg gtctgaacta aaaatgggaa atgtttcaaa    6840
tggaaaaccg gaatatatag aagaatttaa aacatataga agctctcgcg tttacgaggg    6900 catttttttat aaggaggaaa attaaatggc agtaaaacat gcaagtgcgc caaaggcgta    6960
tattaacatt actggtttag gtttcgctaa attaacgaaa gaaggcgcgg aattaaaata    7020
tagtgatatt acaaaaacaa gaggattaca aaaaattggt gttgaaactg gtggagaact    7080
aaaaacagct tatgctgatg gcggtccaat tgaatcaggg aatacagacg gagaaggtaa    7140
aatctcatta caaatgcatg cgttccctaa agagattcgc aaaattgttt ttaatgaaga    7200
ttatgatgaa gatggcgttt acgaagagaa acaaggtaaa caaaacaatt acgtagctgt    7260
atggttcaga caagagcgta agacggtac atttagaaca gttttattac ctaaagttat    7320
gtttacaaat cctaaaatcg atggagaaac ggctgagaaa gattgggatt ctcaagtga    7380 agaggttgaa ggtgaggcac ttttcccttt agttgataat aaaaagtcag tacgtaagta    7440
tatctttgat tcagctaaca tgacaaatca tgatggagac ggtgaaaaag gcgaagaggc    7500
tttcttaaag aaaattttag gcgaagaata tactggaaac gtgacagagg gtaacgaaga    7560
aactttgtaa caaaaccggc ttcatcggaa actgcggtaa agtcggttaa tataccagat    7620
agcattaaaa cacttaaagt tggcgacaca tacgatttaa atgttgtagt agagccatct    7680
aatcaaagta agttattgaa atacacaaca gatcaaacga atattgtatc aatcaatagt    7740
gatggtcaag ttactgcgga agcacaaggc attgctacgg ttaaagcaac agttggtaat    7800
atgagtgaca ctataacaat aaatgtagaa gcataagagg gggcaacccc tctattttat    7860
ttgaaaataa ggagagtatt ataaaatggc aaaattaaaa cgtaacatta ttcaattagt    7920
agaagatcca aaagcaaatg aaattaaatt acaaacgtac ttaacaccac acttcatttc    7980
atttgaaatt gtatacgaag caatggattt aatcgatgat attgaggacg aaaatagcac    8040
gatgaagcca agagaaatcg ctgacagatt gatggatatg gttgtaaaaa tttacgataa    8100
ccaattcaca gttaaagacc taaagaacg tatgcatgca cctgatgaa tgaatgcact    8160 tcgtgaacaa gtgattttca ttactcaagg tcaacaaact gaggaaacta gaaattttat    8220
ccagaacatg aaataaagcc tgaagattta acatataaag caatgttgaa aaatatggat    8280
actctcatga tggacttaat tgaaaatggt aaagacgcta acgaagtttt aaaaatgcca    8340
```

-continued

```
tttcattatg tgctttccat atatcaaaat aaaaataatg acatttctga agaaaaagca    8400
gaggctttaa ttgatgcatt ttaaccttaa ccgtttggtt agggttattt ttttgaactt    8460
ttttagaaag gaggtaaaaa atgggagaaa gaataaaagg tttatctata ggtttggatt    8520
tagatgcagc aaatttaaat agatcatttg cagaaatcaa acgaaacttt aaaactttaa    8580
attctgactt aaaattaaca ggcaacaact tcaaatatac cgaaaaatca actgatagtt    8640
acaaacaaag gattaaagaa cttgatggaa ctatcacagg ttataagaaa aacgttgatg    8700
atttagccaa gcaatatgac aaggtatctc aagaacaggg cgaaaacagt gcagaagctc    8760
aaaagttacg acaagaatat aacaaacaag caaatgagct gaattattta gaaagagaat    8820
tacaaaaaac atcagccgaa tttgaagagt tcaaaaaagc tcaagttgaa gctcaaagaa    8880
tggcagaaag tggctgggga aaaccagta aagttttga aagtatggga cctaaattaa    8940
caaaaatggg tgatggttta aaatccattg gtaaaggttt gatgattggt gtaactgcac    9000
ctgttttagg tattgcagca gcatcaggaa aagcttttgc agaagttgat aaaggtttag    9060
atactgttac tcaagcaaca ggcgcaacag gcagtgaatt aaaaaaattg cagaactcat    9120
ttaaagatgt ttatggcaat tttccagcag atgctgaaac tgttggtgga gttttaggag    9180
aagttaatac aaggttaggt tttacaggta agaacttga aaatgccaca gagtcattct    9240
tgaaattcag tcatataaca ggttctgacg gtgtgcaagc cgtacagtta attacccgtg    9300
caatgggcga tgcaggtatc gaagcaagtg aatatcaaag tgttttggat atggtagcaa    9360
aagcggcgca agctagtggg ataagtgttg atacattagc tgatagtatt actaaatacg    9420
gcgctccaat gagagctatg ggctttgaga tgaaagaatc aattgcttta ttctctcaat    9480
gggaaaagtc aggcgttaat actgaaatag cattcagtgg tttgaaaaaa gctatatcaa    9540
attggggtaa agctggtaaa aacccaagag aagaatttaa gaagacatta gcagaaattg    9600
aaaagacgcc ggatatagct agcgcaacaa gtttagcgat tgaagcattt ggtgcaaagg    9660
caggtcctga tttagcagac gctattaaag gtggtcgctt tagttatcaa gaattttta    9720
aaactattga agattcccaa ggcacagtaa accaaacatt taaagattct gaaagtggct    9780
ccgaaagatt taaagtagca atgaataaat taaaattagt aggtgctgat gtatgggctt    9840
ctattgaaag tgcgtttgct cccgtaatgg aagaattaat caaaaagcta tctatagcgg    9900
ttgattggtt ttccaattta agtgatggtt ctaaaagatc aattgttatt ttcagtggta    9960
ttgctgctgc aattggtcct gtagtttttg ggttaggtgc atttataagt acaattggca   10020
atgcagtaac tgtattagct ccattgttag ctagtattgc aaaggctggt ggattgatta   10080
gttttttatc gactaaagta cctatattag gaactgtctt cacagcttta actggtccaa   10140
ttggcattgt attaggtgta ttggctggtt tagcagtcgc atttacaatt gcttataaga   10200
aatctgaaac atttagaaat tttgttaatg gtgcaattga aagtgttaaa caaacattta   10260
gtaattttat tcaatttatt caaccttttcg ttgattctgt taaaaacatc tttaaacaag   10320
cgatatcagc aatagttgat ttcgcaaaag atatttggag tcaaatcaat ggattcttta   10380
atgaaaacgg aatttccatt gttcaagcac ttcaaaatat atgcaacttt attaaagcga   10440
tatttgaatt tattttaaat tttgtaatta accaattat gttcgcgatt tgcaagtgaa   10500
tgcaatttat ttggccggcg gttaaagcct tgattgtcag tacttgggag aacataaaag   10560
gtgtaataca aggtgcttta aatatcatac ttggcttgat taagttcttc tcaagtttat   10620
tcgttggtga ttggcgagga gtttgggacg ccgttgtgat gattcttaaa ggagcagttc   10680
```

```
aattaatttg gaatttagtt caattatggt ttgtaggtaa aatacttggt gttgttaggt     10740
actttggcgg gttgctaaaa ggattgatag caggaatttg ggacgtaata agaagtatat     10800
tcagtaaatc tttatcagca atttggaatg caacaaaaag tattttttgga tttttattta    10860 atagcgtaaa atcaatttc acaaatatga aaaattggtt atctaatact tggagcagta     10920
tccgtacgaa tacaatagga aaagcgcagt cattatttag tggcgtcaaa tcaaaattta    10980
ctaatttatg gaatgcgacg aaagaaattt ttagtaattt aagaaattgg atgtcaaata    11040
tttggaattc cattaaagat aatacggtag gaattgcaag ccgtttatgg agtaaggtac    11100
gtggaatttt cacaaatatg cgcgatggct tgagttccat tatagataag attaaaagtc    11160
atatcggcgg tatggtaagc gctattaaaa aaggacttaa taaattaatc gacggtttaa    11220
actgggtcgg tggtaagttg ggaatggata aaataccta gttacacact ggtacagagc     11280
acacacatac tactacaaga ttagttaaga acggtaagat tgcacgtgac acattcgcta    11340
cagttgggga taagggacgc ggaaatggtc caaatggttt tagaaatgaa atgattgaat    11400
tccctaacgg taaacgtgta atcacaccta atacagatac taccgcttat ttacctaaag    11460
gctcaaaagt atacaacggt gcacaaactt attcaatgtt aaacggaacg cttccaagat    11520
ttagtttagg tactatgtgg aaagatatta atctggtgc atcatcggca tttaactgga    11580
caaaagataa aataggtaaa ggtaccaaat ggcttggcga taaagttggc gatgttttag    11640
attttatgga aaatccaggc aaactttaa attatatact tgaagctttt ggaattgatt     11700
tcaattcttt aactaaaggt atgggaattg caggcgacat aacaaaagct gcatggtcta    11760
agattaagaa aagtgctact gattggataa aagaaattt agaagctatg ggcggtggcg     11820
atttagtcgg cggaatatta gaccctgaca aaattaatta tcattatgga cgtaccgcag    11880
cttataccgc tgcaactgga agaccatttc atgaaggtgt cgattttcca tttgtatatc    11940
aagaagttag aacgccgatg ggtggcagac ttacaagaat gccatttatg tctggtggtt    12000
atggtaatta tgtaaaaatt actagtggcg ttatcgatat gctatttgcg catttgaaaa    12060
actttagcaa atcaccacct agtggcacga tggtaaagcc cggtgatgtt gttggtttaa    12120
ctggtaatac cggatttagt acaggaccac atttacattt tgaaatgagg agaaatggac    12180
gacattttga ccctgaacca tatttaagga atgctaagaa aaaggaaga ttatcaatag     12240 gtggtggcgg tgctacttct ggaagtggcg caacttatgc cagtcgagta atccgacaag    12300
cgcaaagtat tttaggtggt cgttataaag gtaaatggat tcatgaccaa atgatgcgcg    12360
ttgcaaaacg tgaaagtaac taccagtcaa atgcagtgaa taactgggat ataaatgctc    12420
aaagaggaga cccatcaaga ggattattcc aaatcatcgg ctcaactttt agagcaaacg    12480
ctaaacgtgg atatactaac tttaataatc cagtacatca aggtatctca gcaatgcagt    12540
acattgttag acgatatggt tggggtggtt ttaaacgtgc tggtgattac gcatatgcta    12600
caggtggaaa agttttgat ggttggtata acttaggtga agacggtcat ccagaatgga    12660
ttattccaac agatccagct cgtagaaatg atgcaatgaa gattttgcat tatgcagcag    12720
cagaagtaag agggaaaaaa gcgagtaaaa ataagcgtcc tagccaatta tcagacttaa    12780
acgggtttga tgatcctagc ttattattga aaatgattga acaacagcaa caacaaatag    12840
ctttattact gaaaatagca caatctaacg atgtgattgc agataaagat tatcagccga    12900
ttattgacga atacgctttt gataaaaagg tgaacgcgtc tatagaaaag cgagaaaggc    12960
aagaatcaac aaaagtaaag tttagaaaag gaggaattgc tattcaatga tagacactat    13020
taaagtgaac aacaaaacaa ttccttggtt gtatgtcgaa agagggtttg aaataccctc    13080
```

-continued

```
ttttaattat gttttaaaaa cagaaaatgt agatggacgt tcggggtcta tatataaagg    13140
gcgtaggctt gaatcttata gttttgatat acctttggtg gtacgtaatg actatttatc    13200
tcacaacggc attaaaacac atgatgacgt cttgaatgaa ttagtaaagt tttttaacta    13260
cgaggaacaa gttaaattac aattcaaatc taaagattgg tactggaacg cttatttcga    13320
aggaccaata aagctgcaca aagaatttac aatacctgtt aagttcacta tcaaagtagt    13380
actaacagac ccttacaaat attcagtaac aggaaataaa aatactgcga tttcagacca    13440
agtttcagtt gtaaatagtg ggactgctga cactccttta attgttgaag cccgagcaat    13500
taaaccatct agttacttta tgattactaa aaatgatgaa gattatttta tggttggtga    13560
tgatgaggta accaagaaag ttaaggatta catgcctcct gtttatcata gtgagtttcg    13620
tgatttcaaa ggttggacta agatgattac tgaagatatt ccaagtaatg acttaggtgg    13680
taaggtcggc ggtgactttg tgatatccaa tcttggcgaa ggatataaag caactaattt    13740
tcctgatgca aaaggttggg ttggtgctgg cacgaaacga gggctcccta aagcgatgac    13800
agattttcaa attacctata aatgtattgt tgaacaaaaa ggtaaaggtg ccggaagaac    13860
agcacaacat atttatgata gtgatggtaa gttacttgct tctattggtt atgaaaataa    13920
atatcatgat agaaaaatag gacatattgt tgttacgttg tataaccaaa aaggagaccc    13980
caaaaagata tacgactatc agaataaacc gataatgtat aacttggaca gaatcgttgt    14040
ttatatgcgg ctcagaagag taggtaataa attttctatt aaaacttgga aatttgatca    14100
cattaaagac ccagatagac gtaaacctat tgatatggat gagaaagagt ggatagatgg    14160
cggtaagttt tatcagcgtc cagcttctat catagctgtc tatagtgcga agtataacgg    14220
ttataagtgg atggagatga atgggttagg ttcattcaat acggagattc taccgaaacc    14280
gaaaggcgca agggatgtca ttatacaaaa aggtgattta gtaaaaatag atatgcaagc    14340
aaaaagtgtt gtcatcaatg aggaaccaat gttgagcgag aaatcgtttg gaagtaatta    14400
tttcaatgtt gattctgggt acagtgaatt aatcatacaa cctgaaaacg tctttgatac    14460
gacggttaaa tggcaagata gatatttata gaaaggagag gagagtgtga tacatgtttt    14520
agattttaac gacaagatta tagatttcct ttctactgat gacccttcct tagttagagc    14580
gattcataaa cgtaatgtta atgacaattc agaaatgctt gaactgctca tatcatcaga    14640
aagagctgaa aagttccgtg aacgacatcg tgttattata agggattcaa acaaacaatg    14700
gcgtgaattt attattaact gggttcaaga tacgatggac ggctacacag agatagaatg    14760
tatagcgtct tatcttgctg atataacaac agctaaaccg tatgcaccag gcaaatttga    14820 gaaaagaca acttcagaag cattgaaaga tgtgttgagc gatacaggtt gggaagtttc    14880
tgaacaaacc gaatacgatg gcttacgtac tacgtcatgg acttcttatc aaactagata    14940
tgaagtttta aagcaattat gtacaaccta taaaatggtt ttagattttt atattgagct    15000
tagctctaat accgtcaaag gtagatatgt agtactcaaa aagaaaaaca gcttattcaa    15060
aggtaaagaa attgaatatg gtaaagattt agtcgggtta actaggaaga ttgatatgtc    15120
agaaatcaaa acagcattaa ttgctgtggg acctgaaaat gacaaaggga agcgtttaga    15180 gctagtgtg acagatgacg aagcgcaaag tcaattcaac ctacctatgc gctatatttg    15240
ggggatatat gaaccacaat cagatgatca aaatatgaat gaaacacgat taagttcttt    15300
agccaaaaca gagttaaata aacgtaagtc ggcagttatg tcatatgaga ttacttctac    15360
tgatttggaa gttacgtatc cgcacgagat tatatcaatt ggcgatacag tcagagtaaa    15420
```

```
acatagagat tttaacccgc cattgtatgt agaggcagaa gttattgctg aagaatataa   15480
cataatttca gaaaatagca catatacatt cggtcaacct aaagagttca aagaatcaga   15540
attacgagaa gagtttaaca agcgattgaa cataatacat caaaagttaa acgataaatat  15600 tagcaatatc aacactatag ttaaagatgt tgtagatggt gaattagaat actttgaacg   15660
caaaatacac aaaagtgata caccgccaga aaatccagtc aatgatatgc tttggtatga   15720
tacaagtaac cctgatgttg ctgtcttgcg tagatattgg aatggtcgat ggattgaagc   15780
aacaccaaat gatgttgaaa aattaggtgg tataacaaga gagaaagcgc tattcagtga   15840
attaaacaat attttatta atttatctat acaacacgct agtcttttgt cagaagctac   15900
agaattactg aatagcgagt acttagtaga taatgatttg aaagcggact acaagcaag   15960 tttagacgct gtgattgatg tttataatca aattaaaaat aatttagaat ctatgacacc   16020
cgaaactgca acgattggtc ggttggtaga tacacaagct ttatttcttg agtatagaaa   16080
gaaattacaa gatgtttata cagatgtaga agatgtcaaa atcgccattt cagatagatt   16140
taaattatta cagtcacaat acactgatga aaaatataaa gaagcgttgg aaataatagc   16200
aacaaaattt ggtttaacgg tgaatgaaga tttgcagtta gtcggagaac ctaatgttgt   16260
taaatcagct attgaagcag ctagagaatc cacaaaagaa caattacgtg actatgtaaa   16320
aacatcggac tataaaacag acaaagacgg tattgttgaa cgtttagata ctgctgaagc   16380
tgagagaacg actttaaaag gtgaaatcaa agataaagtt acgttaaacg aatatcgaaa   16440
cggattggaa gaacaaaaac aatatactga tgaccagtta agtgatttgt ccaataatcc   16500
tgagattaaa gcaagtattg aacaagcaaa tcaagaagcg caagaagctt aaaatcata   16560 cattgatgct caagatgatc ttaaagagaa ggaatcgcaa gcgtatgctg atggtaaaat   16620
ttcggaagaa gagcaacgcg ctatacaaga tgctcaagct aaacttgaag aggcaaaaca   16680
aaacgcagaa ctaaaggcta gaaacgctga aaagaaagct aatgcttata cagacaacaa   16740
ggtcaaagaa agcacagatg cacagaggaa acattgact cgctatggtt ctcaaattat   16800
acaaaatggt aaggaaatca aattaagaac tactaaagaa gagtttaatg caaccaatcg   16860
tacactttca aatatattaa acgagattgt tcaaaatgtt acagatggaa caacaatcag   16920
atatgatgat aacggagtgg ctcaagcttt gaatgtgggg ccacgtggta ttagattaaa   16980
tgctgataaa attgatatta acggtaatag agaaataaac cttcttatcc aaaatatgcg   17040
agataaagta gataaaaccg atattgtcaa cagtcttaat ttatcaagag agggtcttga   17100
tatcaatgtt aatagaattg gaattaaagg cggtgacaat aacagatatg ttcaaataca   17160
gaatgattct attgaactag gtggtattgt gcaacgtact tggagaggga aacgttcaac   17220
agacgatatt tttacgcgac tgaaagacgg tcacctaaga tttagaaata acaccgctgg   17280
cggttcactt tatatgtcac attttggtat ttcgacttat attgatggtg aaggtgaaga   17340
cggtggttca tctggtacga ttcaatggtg ggataaaact tacagtgata gtggcatgaa   17400
tggtataaca atcaattcct atggtggtgt cgttgcacta acgtcagata taatcgggt   17460 tgttctggag tcttacgctt catcgaatat caaaagcaaa caggcaccgg tgtatttata   17520
tccaaacaca gacaaagtgc ctggattaaa ccgatttgca ttcacgctgt ctaatgcaga   17580
taatgcttat tcgagtgacg gttatattat gtttggttct gatgagaact atgattacgg   17640
tgcgggtatc aggttttcta aagaaagaaa taaggtcttg gttcaaattg ttaatggacg   17700
atatgcaaca ggtggagata caacaatcga agcagggtat ggcaaattta atatgctgaa   17760
acgacgtgat ggtaataggt atattcatat acagagtaca gacctactgt ctgtaggttc   17820
```

```
agatgatgca ggagatagga tagcttctaa ctcaatttat agacgtactt attcggccgc   17880
agctaatttg catattactt ctgctggcac aattgggcgt tcgacatcag cgcgtaaata   17940
caagttatct atcgaaaatc aatataacga tagagatgaa caactggaac attcaaaagc   18000
tattcttaac ttacctatta gaacgtggtt tgataaagct gagtctgaaa ttttagctag   18060
agagctgaga gaagatagaa aattatcgga agacacctat aaacttgata gatacgtagg   18120
tttgattgct gaagaggtgg agaatttagg attaaaagag tttgtcacgt atgatgacaa   18180
aggagaaatt gaaggtatag cgtatgatcg tctatggatt catcttatcc ctgttatcaa   18240
agaacaacaa ctaagaatca agaaattgga ggagtcaaag aatgcaggat aacaaacaag   18300
gattacaagc taatcctgaa tatacaattc attatttatc acaggaaatt atgaggttaa   18360
cacaagaaaa cgcgatgtta aaagcgtata taagaaaaa taagaaaaat caacaatgtg   18420
ctgaggaaga gtaatcctta gcactatttt tatacaaaaa tttaaggagg tcatttaatt   18480
atggcaaaag aaattatcaa caatacagaa aggtttattt tagtacaaat cgacaaagaa   18540
ggtacagaac gtgtagtata tcaagatttc acaggaagtt ttacaacttc tgaaatggtt   18600
aaccatgctc aagattttaa atctgaagaa aacgctaaga aaattgcgga gacgttaaat   18660
ttgttatatc aattaactaa caaaaaacaa cgtgtgaaag tagttaaaga agtagttgaa   18720
agatcagatt tatctccaga ggtaacagtt aacactgaaa cagtatgaaa agctatgagt   18780
tagatactca tagtctttat tcttttagaa agcgggtgta ctgaattggg gtggttcaaa   18840
aaacacgaac atgaatggcg catcagaagg ttagaagaga atgataaaac aatgctcagc   18900
acactcaacg aaattaaatt aggtcaaaaa acccaagagc aagttaacat taaattagat   18960
aaaaccttag atgctattca aaaagaaaga gaaatagatg aaaagaataa gaaagaaaat   19020
gataagaaca tacgtgatat gaaaatgtgg gtgcttggtt tagttgggac aatatttggg   19080
tcgctaatta tagcattatt gcgtatgctt atgggcatat aagagaggtg attaccatgt   19140
tcggattaaa ttttggagct tcgctgtgga cgtgtttctg gtttggtaag tgtaagtaat   19200
agttaagagt cagtgcttcg gcactggctt tttattttgg ataaaaggag caaacaaatg   19260
gatgcaaaag taataacaag atacatcgta ttgatcttag cattagtaaa tcaattctta   19320
gcgaacaaag gtattagccc aattccagta gacgatgaaa ctatatcatc aataatactt   19380
actgtagtcg ctttatatac aacgtataaa gacaatccaa catctcaaga aggtaaatgg   19440
gcaaatcaaa aattaaagaa atataaagct gaaaataagt atagaaaagc aacagggcaa   19500
gcgccaatta aagaagtaat gacacctacg aatatgaacg acacaaatga tttagggtag   19560
gtggttgata tatgttaatg acaaaaaatc aagcagaaaa atggtttgac aattcattag   19620
ggaaacaatt caacccagat ggttggtatg gatttcagtg ttatgattac gccaatatgt   19680
tctttatgtt agcgacaggc gaaaggctgc aaggtttata tgcttataat atcccgtttg   19740
ataataaagc aaagattgaa aaatatggtc aaataattaa aaactatgac agcttttttac   19800 cgcaaaagtt ggatattgtc gttttcccgt caaagtatgg tggcggagct ggacacgttg   19860
aaattgttga gagcgcaaat ttaaatactt tcacatcatt tggtcaaaac tggaacggta   19920
aaggttggac taatggcgtt gcgcaacctg gttgggtcc tgaaactgtg acaagacatg   19980
ttcattatta tgacaatcca atgtatttta ttaggttaaa cttccctaac aacttaagcg   20040
ttggcaataa agctaaaggt attattaagc aagcgactac aaaaaagag gcagtaatta   20100 aacctaaaaa aattatgctt gtagccggtc atggttataa cgatcctgga gcagtaggaa   20160
```

```
acggaacaaa cgaacgcgat tttatacgta aatatataac gcctaatatc gctaagtatt    20220
taagacatgc aggacatgaa gttgcattat acggtggctc aagtcaatca caagatatgt    20280
atcaagatac tgcatacggt gttaatgtag gcaataaaaa agattatggc ttatattggg    20340
ttaaatcaca ggggtatgac attgttctag aaatacattt agacgcagca ggagaaagcg    20400
caagtggtgg gcatgttatt atctcaagtc aattcaatgc agatactatt gataaaagta    20460
tacaagatgt tattaaaaat aacttaggac aaataagagg tgtgacacct cgtaatgatt    20520
tactaaatgt taatgtatca gcagaaataa atataaatta tcgtttatct gaattaggtt    20580
ttattactaa taaaaatgat atggattgga ttaagaaaaa ctatgacttg tattctaaat    20640
taatagccgg tgcgattcat ggtaagccta taggtggttt ggtagctggt aatgttaaaa    20700
catcagctaa aaacaaaaaa aatccaccag tgccagcagg ttatacactc gataagaata    20760
atgtccctta taaaaagaa caaggcaatt acacagtagc taatgttaaa ggtaataatg    20820 taagagacg ttattcaact aattcaagaa ttacaggggg attacccaac aacacaacaa    20880
ttacgtatga cggtgcatat tgtattaatg gttatagatg gattacttat attgctaata    20940
gtggacaacg tcgttatata gcgacaggag aggtagacaa ggcaggtaat agaataagta    21000
gttttggtaa gtttagcacg atttagtatt tacttagaat aaaaattttg ctacattaat    21060
tatagggaat cttacagtta ttaaataact atttggatgg atgttaatat tcctatacac    21120
tttttaacat ttctctcaag atttaaatgt agataacagg caggtacttc ggtacttgcc    21180 tatttttta tgttatagct agccttcggg ctagtttttt gttatgatgt gttacacatg    21240
catcaactat ttacatctat ccttgttcac ccaagcatgt cactggatgt ttttttcttgc    21300 gatagagagc atagttttca tactactccc cgtagtatat atgactttag cattcccgta    21360
taacagttta cggggtgctt ttatgttata attgctttta tatagtagga gtgaactata    21420
tagccgggca gaggccatgt atctgactgt tggtcccaca ggagacatct tccttgtcat    21480
cactcgatac atatatctta acaacataga aatgttacat tcgctataac cgtatcttaa    21540
tcgatacggt tatatttatt ccctacaac caacaaaacc acagatccta ttaatttagg    21600
attgtggtta tttttgcgt tttttgggg caaaaaaagg gcagattatt tgaaaagggg    21660
caaacgcttg tggaaaagct aaaaggttaa aaatgacaaa aaccttgata caacagtgtt    21720
tttggacgct cgtgtacgtt agagaatgac cggtttacca tcatacaagg gtgggattaa    21780
cttgtgttaa aaagccttta atatcagttg ttacaaagga tttgtagcgt ctttaaaaat    21840
aaaaaagggc agaaaaggg cagataccttt ttagtacaca agttttttcta atttttgctc    21900 taactctctg tccattttct ctgttacatg tgtatacacc tttatagtcg ttttttcatc    21960
tgtatgtcct actcttttca taattgcttt taacgatata ttcatttccg ccaataaact    22020
tatgtgtgta tgccttagtg tgtgagtagt aactttttta tttatattta atgattctgc    22080
agctgaggac aatcgtttgt ttatcctact gccttgcata ggatttcctt ggcaagttgt    22140
gaatataaac cctctatcaa catagcttgg ttcccattgt tgcatctttt tattttctaa    22200
cattattttt ttcaatacat ttgctatcct tgaattgatg gcgattttc ttcttgaacc    22260 tgcggtctta gtagtatctt tgtgaccaaa tccagcatta catttgattc tgtgaatagt    22320
gccattaata gcgatcgttt tattttttgag gtcaacatct ttaacttgga gagctaataa    22380
ctcacctatg cgcataccctg ttaaagcttg aacttctaca gccccagcaa ctaaaatacg    22440
agctctatac tgcatgttat tatcgttcag tataaaatcg cgtatctgta ttacctgttc    22500
catctctaaa tagttataca ttttcgcttc ttcttttttct atatcttcta tcgtcttact    22560
```

-continued

```
cttctttggt agtgtgacgc tatttaatat gtgttcgttt ggataattgt aaaatttaac   22620
ggcgtattta atagcttctt tcatatgtcc aagttgacgc tttacctgat ttgcagaata   22680
tacgtttgat aatttgttaa taaatgtttg catgtacttt gtatcaattt tgtttaaaag   22740
taaattttga gaactgttct ttttgatgtt tttgattctt gttttcaaat tatcaagcgt   22800
cgttacttta aagccagatg tttttatatg atattcaagc cattcatcta ataacgcgtg   22860
aaaagtcaaa gttttttaatt cgcttgacga cttgttgttt agttttttctt ttattttttc   22920
ttctaaacga aacattgcct cttttttgcga ttgctttgta ttcttattca agacaacact   22980
tacacgtttc catttatctg tatacggatc tttgtatttc tcgtagtatc tatacttcgt   23040
ttcattgttc ttattttttaa attttttcaaa ccacattttta catccctcct caaaattggc   23100
aaaaaataat aagggtaggc gggctaccca tgaaaattgt ataaaaaaag acgcctgtat   23160
aaaatacaga cgccacttat aattataaga ttacatggtt aattaccaaa aatggtaacg   23220
aatatatacg tgttttaaag gataaacctt taatatatta aaattatatc atcttatatc   23280
agggatctgc aatatattat tattaattct atttatcagt aacataatat ccgaagaatc   23340
tattactgga ttttttaattt tttggggtaa aacttttctt atgcgaaact tactaatcgg   23400
ctggaaagaa tttatgcaag cgtaactatt accttttaat ttttttacct tatcaattgc   23460
tgatactatg ttattaatgt ttctgtcaat tttatttaat ttattttcaa tttctaaact   23520
atcagatata aattcaataa ataatcttt agtgatgaat tctgtgttgt tttttttggta   23580
ttttttatcg aaaacttctt ttaatatagc tgaattattt tgcgcgctaa ttaaatttaa   23640
aaacaatctt aaataatact cccatttcaa atcaaaattc atctttaaat acttttttgtt   23700
ttctttagag gataagggaa taacatttac tatatcctcc gtattagaat catttttatt   23760
catcactatt gcaaagtgtg aattagaaaa ttctttatta acgtttatac cgaaatctac   23820
aaaaactatt tctccttgtt taaactttgg ataaaaacct ttatggtttt tttcaccttc   23880
aaatctcttg agtaaatagt gaatatctga atctaacttt ttaaattttg gatttccaga   23940
agttttttaat ttattaatgc gttttttctat attatgcgtc atcatttctc ctttattctc   24000
gctcacactc tcaccaccat tcaacgtcta cacttgtagg cgttttttga ttagtaaaat   24060
cataatgaat cttctttggt taacttatcg ccatctattt tttgtgaaat aaattccaag   24120
tatttacgcg cattatgtga cgataaatct ttaggtaact cataagtgaa tggttgatta   24180
ccactagtta aaacttcata tactatagtt tctttttttta ttttgcaatt agttattttc   24240
attataaact ccttttaaac actgctgaaa tagacgtctt tttcaaataa gcatgattaa   24300
tactttaatt ctttaatcca catatattta aaagtgaggt agtaggtaat aaatataaga   24360
cttaaagtta agattgcttt tttcatgtca atttctcctt tgtttatatt tatattaaag   24420
cgctaaaatat acgttattaa tcacaataca actttgccca ttactttaat atcactaaac   24480
gaagcgactt tgatatcatc atacttcgga tttagagata ccaaattaat atagtcttcg   24540
catatatcta cacgcttgat aagacttact ccatctaata caacgagtgc aattgtacca   24600
tctttaatag aatcttcttt cttaataaaa gcgtatgttc cttgttttaa cataggttcc   24660
attgaatcac cattaactaa aatacaaaaa tcagcatttg atggcgtttc gtcttctttta   24720
aaaaatactt cttcatgcaa tatgtcatca tataattctt ctcctatgcc agcaccagtt   24780
gcaccacatg caaatacga tactagttta gactctttat attcatctat agaagtgact   24840
ttattctgtt catctaattg ctcatttgca tagttaagta cgttttcttg gcggggaggt   24900
```

```
gtgagttgag aaaatatgtt attgattttt gacattatcg tttcatcttg acgttcttcg   24960
tcaggaactc gataagaatc tacatcatac cccataagcc acgcttcacc gacatttaaa   25020
gttttagata ataagaataa tttatgttgg tctggagaag accttccatt aacatactgg   25080
gataagtgac ttttttgacat tttaatattc aattcttttt gaaagggttt cgactttct   25140 agaatatcta cttgacgcaa gttcctatct ttcataattt gttttaatct ttcagaagtg   25200
ttttgcattg gtaatgcctc cttgaaattc attatatagg aagggaaata aaaatcaata   25260
caaaagttca actttttaa cttttttgtgt tgacattgtt caaaattggg gttatagtta   25320
ttatagttca aatgttgaa cttaggaggt gattatttga atactaatac aacttttgat   25380
ttttcgttat tgaacggtaa gatagtcgaa gtgtactcga cacaatttaa ctttgctata   25440
gctttaggtg tatcagaaag aactttgtct ttgaagttga acaacaaagt accatggaaa   25500
acaacagaca ttattaaagc ttgtaagtta ttgggaatac ctataaaaga tgttcacaaa   25560
tattttttta aacagaaagt tcaaatgttt gaacttaata agtaaaggag gcataacaca   25620
tgcaagaacg agaaaaggtt aataaaagta acacatcttc aaatgaagca tcaaaacctt   25680
ttaggacaaa ttgaagctta cgacaaaacg cttaaagaaa taaagtacac tcgagacctt   25740
tacaacaaac acctaagcat gaacaacgaa gacgcattcg ctggtttgga aatggtagag   25800
gatgaaatta ctaaaaagct acgaagtgct atcaaagagt tccaaaaagt agtgaaagcg   25860
ttagacaagc ttaacggtgt tgaaagcgat aacaaagtta ctgatttaac agagtggcgg   25920
aaagtgaatc agtaacattc acttcttaat ataaccacgc ttatcaacat ccacattgag   25980
cagatgtgag cgagagctgg cgatgatatg agccgcgttt aaatacattc gatagtcatt   26040
gcgataaccg tctgctgaat gtgggtgttg aggaaaaagg aggatactca aatgcaagca   26100
ttacaaacat ttaattttaa agagctacca gtaagaacag tagaaattga aaacgaacct   26160
tattttgtag gaaaagatat tgctgagatt ttaggatatg caagatcaaa caatgccatt   26220
agaaatcatg ttgatagcga ggacaagctg acgcaccaat ttagtgcatc aggtcaaaac   26280
agaaatatga tcattatcaa cgaatcagga ttatacagtc taatcttcga tgcttctaaa   26340
caaagcaaaa acgaaaaaat tagagaaacc gctagaaaat tcaaacgctg ggtaacatca   26400
gatgtcctac cagctattcg caaacacggt atatacgcaa cagacaatgt aattgaacaa   26460
acattaaaag atccagacta catcattaca gtgttgactg agtataagaa agaaaaagag   26520
caaaacttac ttttacaaca gcaagtagaa gttaacaaac caaagtatt attcgctgac   26580 tcggtagctg gtagtgataa ttcaatactt gttggagaac tagcgaaaat acttaaacaa   26640
aacggtgttg atataggaca aaacagattg ttcaaatggt taagaaataa tggatatctc   26700
attaaaaaga gtggagaaag ttataactta ccaactcaaa agagtatgga tctaaaaatc   26760
ttggatatca aaaacgaat aattaataat ccagatggtt caagtaaagt atcacgtaca   26820
ccaaaagtaa caggcaaagg acaacaatac tttgttaata gttttttagg agaaaaacaa   26880
acatcttaaa aggaggaaca caatggaaca aatcacatta accaaagaag agttgaaaga   26940
aattatagca aaagaagtta gagaggctat aaatggcaag aaaccaatca gttcaggttc   27000 aatttttcagt aaagtaagaa tcaataatga cgatttagaa gaaatcaata aaaaactcaa   27060
tttcgcaaaa gatttgtcgc taggaagatt gaggaagctc aatcatccga ttccgctaaa   27120
aaagtatcag catggcttcg aatcaattca tcaaaaagct tatgtacaag atgttcatga   27180
ccatattaga aaattaacat tatcaatttt tggagtgaca cttaattcag acttgagtga   27240
aagtgaatac aacctagcag caaaagttta tcgagaaatc aaaaactatt atttatacat   27300
```

-continued

```
ctatgaaaag agagtttcag aattaactat cgatgatttc gaataaagga ggaacaacaa   27360
atgttacaaa aatttagaat tgcgaaagaa aaaaataaat taaaactcaa attactcaag   27420
catgctagtt actgtttaga agaaacaac aaccctgaac tgttgcgagc agttgcagag    27480
ttgttgaaaa aggttagcta aattcaacgg taaggatttg ccctgcctcc acacttagag   27540
tttgagatcc aacaaacaca taagttttag tagggtctag aaaaaatgtt tcgatttcct   27600
cttttgtaac agtttcaatt ccttcatatc ctggaaaaac aattttcttt aaatccgaaa   27660
catgtttttt tgaaccatcc tttaaagtaa ctagaagttt catacttatc acctccttag   27720
gttgataaca acattataca cgaaaggagc ataaacaata tgcaagcatt acaaacaaat   27780
tcgaacatcg gagaaatgtt caatattcaa gaaaagaaa atggagaaat cgcaatcagc    27840
ggtcgagaac ttcatcaagc attagaagtt aagacagcat ataaagattg gtttccaaga   27900
atgcttaaat acggatttga agaaaataca gattacacag ctatcgctca aaaaagagca   27960
acagctcaag gcaatatgac tcactatatt gaccacgcac tcacactaga cactgcaaaa   28020
gaaatcgcaa tgattcaacg tagtgaacct ggcaaacgtg caagacaata tttcatccaa   28080
gttgaaaaag catggaacag cccagaaatg attatgcaac gtgctttaaa aattgctaac   28140
aacacaatca atcaattaga aacaaagatt gcacgtgaca aaccaaaaat tgtatttgca   28200
gatgcagtag ctactactaa gacatcaatt ttagttggag agttagcaaa gatcattaaa   28260
caaaacggta taaacatcgg gcaacgcaga ttgtttgagt ggttacgtca aaacggattc   28320
cttattaaac gcaagggtgt ggattataac atgcctacac agtattcaat ggaacgtgag   28380
ttattcgaaa ttaaagaaac atcaatcaca cattcggacg gtcacacatc aattagtaag   28440
acgccaaaag taacaggtaa aggacaacaa tactttgtta acaagttttt aggagaaaaa   28500
caaacaactt aataggagga attacaaatg aacgcactat acaaaacaac cctcctcatc   28560
acaatggcag ttgtgacgtg gaaggtttgg aagattgaga agcacactag aaaacctgtg   28620
attagtagca gggcgttgag tgactatcta aacaacaaat ctttaaccat accgaaagat   28680
gctgaaaatt ctactgaatc tgctcgtcgc cttttgaagt tcgccgaaca aactattagc   28740
aaataacaac attatacacg aaaggaaaga tagaaatgcc aaaaatcata gtaccaccaa   28800
caccagaaaa cacatataga ggcgaagaaa aatttgtgaa aaagttatac gcaacaccta   28860
cacaaatcca tcaattgttt ggagtatgta gaagtacagt atacaactgg ttgaaatatt   28920
accgcaaaga taatttaggt gtagaaaatt tatacattga ttattcacca acaggcactc   28980
tgattaatat ttctaaattg gaagagtatt tgatcagaaa gcataaaaaa tggtattagg   29040
aggatattaa atgagcaaca tttataaaag ctacctagta gcagtattat gcttcacagt   29100
cttagcgatt gtacttatgc cgtttctata cttcactaca gcatggtcaa ttgcgggatt   29160
cgcaagtatc gcaacattca tgtactacaa agaatgcttt ttcaaagaat aaaaaaactg   29220
ctacttgttg gagcaagtaa cagtatcaaa cacttaagaa aaaattcatg ttcaatataa   29280
aacgaaaaac ggaggaagtc aagatgtatt acgaaatagg cgaaatcata cgcaaaaata   29340
ttcatgttaa cggattcgat tttaagctat tcatttaaa aggtcatatg gcatatcaa    29400 tacaagttaa agatatgaac aacgtaccaa ttaaacatgc ttatgtcgta gatgagaatg   29460
acttagatat ggcatcagac ttatttaacc aagcaataga tgaatggatt gaagagaaca   29520
cagacgaaca ggacagacta attaacttag tcatgaaatg gtaggaggtc gctatgaagc   29580
agactgtaac ttatatcatt cgtcataggg atatgccaat ttatataact aacaaaccaa   29640
```

```
ctgataacaa ttcagatatt agttactcca caaatagaaa tagagctagg gagtttaacg   29700
gtatggaaga agcgagtatc aatatggatt atcacaaagc aatcaagaaa acagtgacag   29760
aaactattga gtacgaggag gtagaacatg actgaggaaa acaagaacc acaagaaaaa    29820 gtaagcatac tcaaaaaact aaagataaat aatatcgctg agaaaataa aaggaaattc    29880 tataaatttg cagtatacgg aaaaattggc tcaggaaaaa ccacgtttgc tacaagagat   29940
aaagacgctt tcgtcattga cattaacgaa ggtggaacaa cggttactga cgaaggatca   30000
gacgtagaaa tcgagaacta tcaacacttt gtttatgttg taaattttt acctcaaatt    30060 ttacaggaga tgagagaaaa cggacaagaa atcaatgttg tagttattga aactattcaa   30120
aaacttagag atatgacatt gaatgatgtg atgaaaaata agtctaaaaa accaacgttt   30180
aatgattggg gagaagttgc tgaacgaatt gtcagtatgt acagattaat aggaaaactt   30240
caagaagaat acaaattcca ctttgttatt acaggtcatg aaggtatcaa caaagataaa   30300
gatgatgaag gtagcactat caaccctact atcactattg aagcgcaaga acaaattaaa   30360
aaagctatta cttctcaaag tgatgtgtta gctagggcaa tgattgaaga atttgatgat   30420
aacggagaaa agaaagctag atatattcta aacgctgaac cttctaatac gtttgaaaca   30480
aagattagac attccccttc aataacaatt aacaataaga aatttgcaaa tcctagcatt   30540
acggacgtag tagaagcaat tagaaatgga aactaaaaat taattaaaag gacggtatt    30600 aattatgaaa tcacaggac aagcgcaatt tactaaagaa acaaatcaag aaaagtttta    30660
taacggctca gcagggtttc aagctggaga attcacagtg aaagttaaaa atattgaatt   30720
caatgataga gaaaatagat atttcacaat cgtatttgaa aatgatgaag gcaaacaata   30780
taaacataat caatttgtac cgccgtataa atatgatttc caagaaaaac aattgattga   30840
attagttact cgattaggta ttaagttaaa tcttcctagc ttagattttg ataccaatga   30900
tcttattggt aagttttgtc acttggtatt gaaatggaaa ttcaatgaag atgaaggtaa   30960
gtattttacg gatttttcat ttattaaacc ttacaaaaag ggcgatgatg ttgttaacaa   31020
acctattccg aagacagata agcaaaaagc tgaagaaaat aacggggcac aacaacaaac   31080
atcaatgtct caacaaagca atccattttga aagcagtggc caatttggat atgacgacca   31140
agatttagcg ttttaaggtg tggttttaaat gcaatacatt acaagatacc agaaagataa   31200
cgacggtact tattccgtcg ttgctactgg tgttgaactt gaacaaagtc acattgactt   31260
actagaaaac ggatatccac taaaagcaga agtagaggtt ccggacaata aaaaactatc   31320
tatagaacaa cgcaaaaaaa tattcgcaat gtgtagagat atagaacttc actggggcga   31380
accagtagaa tcaactagaa aattattaca aacagaattg gaaattatga aaggttatga   31440
agaaatcagt ctgcgcgact gttctatgaa agttgcaagg gagttaatag aactgattat   31500
agcgtttatg tttcatcatc aaataccctat gagtgtagaa acgagtaagt tgttaagcga   31560
agataaagcg ttattatatt gggctacaat caaccgcaac tgtgtaatat gcggaaagcc   31620
tcacgcagac ctggcacatt atgaagcagt cggcagaggc atgaacagaa acaaaatgaa   31680
ccactatgac aaacatgtat tagcgttatg tcgcgaacat cacaacgagc aacatgcgat   31740
tggcgttaag tcgtttgatg ataaatacca cttgcatgac tcgtggataa agttgatga    31800 gaggctcaat aaaatgttga aaggagagaa aaaggaatga atagactaag aataataaaa   31860
atagcactcc taatcgtcat cttggcggaa gagattagaa atgctatgca tgctgtaaaa   31920
gtggagaaaa ttttaaaatc tccgtttagt taatacaggt ttttacaaaa gctttaccat   31980
aggcggacaa actaattgag cctttttga tgtctattac ccagggctg taatgtaact    32040
```

```
ttaatacttc aaattcaatg ccagaaagtt tacttattgt ttctaggttg tgtcctgact   32100
ttaacattct tttaacaaat tctaatcccg aaacaaatct ttgtttttct ataatcttat   32160
taaagtgatt taaaaactga ggagcataaa acttattata aattccttt tttgttaagt    32220
aagacatgtc aaaagtttca tttaaaaccc ctaaccttac taggttatta attgaaattt   32280
cggttgattc tatatctaac ggagagtctt ttattaacgt gtccgatata ttcataccgt   32340
cattctttgg gtttaaaacc gctctatatt taacggcagg atgtacttcg tgattcttta   32400
aatgttttaa aagaatagca tcatttgggg ataattgttt aattatttca acaaatgaat   32460
ggtgggttaa tgagttttt ctgtcatcca tagatgatgc tattagtttt gcgaacatat    32520
tacttaaagt tttttcacta atgtaaaact ttgaagcttc tagagcagga cctagaagag   32580
aaaattgtgg ttcttgtaaa ttattttag gtacagaaga tatttctttt ttaaattgtt    32640
ctttgaattt ttcaaattct acttctcttt gataaataac tttatccaca taaggtgga    32700
atttcccaaa gacaagttcc caagttttag agaatgtttc tacaggccct tttgatgcgc   32760
cttcaataat tttatcaata cctttaccta aaataggatc cataattatt cacccccaat   32820
ctaacgcaat agcgataata aaattatacc agaaggaga atcaacatga ctgaccaacc    32880
aagttactac tcaataatta cagcaaatgt cagatacgat aaccgactta ctgcagcga    32940
aaagttactt tttgcagaaa taacatcttt aagtaacaaa tacggatact gcacagcaag   33000
taatggttac tttgcaactt tatacaacgt tgttaaggaa actatatctc gtagaatttc   33060
gaaccttacc aactttggtt atctaaaaat cgaaattatc aaagaaggta atgaagttaa   33120
acaaaggaag atgtacccct tgacgcaaac gtcaataacct attgacgcaa aaatcaatac   33180
ccctattgat aattctgtca ataccctat tgacgcaaat gtcaaagaga atattacaag    33240
tattaataat acaagtaata acaatataaa tagaatagat atattgtcgg gcaacccgac   33300
agcatcttct ataccctata aagaaattat cgattactta acaaaaaag cgggcaagca   33360
ttttaaacac aatacagcta aaacaaaaga ttttattaaa gcaagatgga atcaagattt   33420
taggttggag gattttaaaa aggtgattga tatcaaaaca gctgagtggc taaacacgga   33480
tagcgataaa taccttagac cagaaacact ttttggcagt aaatttgagg ggtacctcaa   33540
tcaaaaaata caaccaactg gcacggatca attggaacgc atgaagtacg acgaaagtta   33600
ttgggattag ggggatatta tgaaaccact attcagcgaa aagataaacg aaagcttgaa   33660
aaaatatcaa cctactcatg tcgaaaaagg attgaaatgt gagagatgtg gaagtgaata   33720
cgacttatat aagtttgctc ctactaaaaa acacccgaat ggttacgagt ataaagacgg   33780
ttgcaaatgt gaaatctatg aggaatataa gcgaaacaag caacggaaga taaacaacat   33840
attcaatcaa tcaaacgtta atccgtctt aagagatgca acagtcaaaa actacaagcc   33900
acaaaatgaa aaacaagtac acgctaaaca aacagcaata gagtacgtac aaggcttctc    33960
tacaaaagaa ccaaaatcat taatattgca aggttcatac ggaactggta aaagccacct   34020
agcatacgct atcgcaaaag cagtcaaagc taaagggcat acggttgctt ttatgcacat   34080
accaatgttg atggatcgta tcaaagcgac atacaacaaa aatgcagtag agactacaga   34140
cgagctagtc agattgctaa gtgatattga tttacttgta ctagatgata tgggtgtaga   34200
aaacacagag cacactttaa ataaactttt cagcattgtt gataacagag taggtaaaaa   34260
caacatcttt acaactaact ttagtgataa agaactaaat caaaatatga actggcaacg   34320
tataaattcg agaatgaaaa aaagagcaag aaaagtaaga gtaatcggag acgatttcag   34380
```

```
ggagcgagat gcatggtaac caaagaattt ttaaaaacta aacttgagtg ttcagatatg    34440
tacgctcaga aactcataga tgaggcacag ggcgatgaaa ataggttgta cgacctattt    34500
atccaaaaac ttgcagaacg tcatacacgc cccgctatcg tcgaatatta aggagtgtta    34560
aaaatgccga agaaaaata ttacttatac cgagaagatg gcacagaaga tattaaggtc    34620
atcaagtata aagacaacgt aaatgaggtt tattcgctca caggagccca tttcagcgac    34680
gaaaagaaaa ttatgactga tagtgaccta aaacgattca aaggcgctca cgggcttcta    34740
tatgagcaag aattaggttt acaagcaacg atatttgata tttagaggtg gacgatgagt    34800
aaatacaacg ctaagaaagt tgagtacaaa ggaattgtat ttgatagcaa agtagagtgt    34860
gaatattacc aatatttaga aagtaatatg aatggcacta attatgatca tatcgaaata    34920
caaccgaaat tcgaattatt accaaaacta gataaacaac gaaagattga atatattgca    34980
gacttcgcgt tatatctcga tggcaaactg attgaagtta tcgacattaa aggtatgcca    35040
accgaagtag caaaacttaa agctaagatt ttcagacata aatacagaaa cataaaactc    35100
aattggatat gtaaagcgcc taagtataca ggtaaaacat ggattacgta cgaggaatta    35160
attaaagcaa gacgagaacg caaaagagaa atgaagtgat ctaatgcaac aacaagcata    35220
tataaatgca acgattgata taaggatacc tacagaagtt gaatatcagc attttgatga    35280
tgtggataaa gaaaaagaag cgctggcaga ttacttatat aacaatcctg acgaaatact    35340
agagtatgac aatttaaaaa ttagaaacgt aaatgtagag gtggaataaa tgggcagtgt    35400
tgtaatcatt aataataaac catataaatt taacaatttt gaaaaaagaa ataatggcaa    35460
agcgtgggat aaatgctgga attgtttcta aacgtgttag aggttgttgg gagttttcag    35520
aagctttaga cgcgccttat ggcatgcacc taaaagaata tagagaaatg aaacaaatgg    35580
aaaagattaa acaagcgaga ctcgaacgtg aattggaaag agagcgaaag aaagaggctg    35640
agctacgtaa gaagaagcca catttgttta atgtacctca aaaacattca cgtgatccgt    35700
actggttcga tgtcacttat aaccaaatgt tcaagaaatg gagtgaagca taatgagcat    35760
aatcagtaac agaaaagtag atatgaacaa acgcaagac aacgttaagc aacctgcgca    35820
ttacacatac ggcgacattg aaattataga ttttattgaa caagttacgg cacagtaccc    35880
accacaatta gcattcgcaa taggtaatgc aattaaatac ttgtctagag caccgttaaa    35940
gaatggtcat gaggatttag caaaggcgaa gttttacgtc gatagagtat ttgacttgtg    36000
ggagtgatga ccatgacaga tagcggacgt aaagaatact taaaacattt tttcggctct    36060
aagagatatc tgtatcagga taacgaacga gtggcacata tccatgtagt aaatggcact    36120
tattactttc acggtcatat cgtgccaggt tggcaaggtg tgaaaaagac atttgataca    36180
gcggaagagc ttgaaacata tataaagcaa agtgatttgg aatatgagga acagaagcaa    36240
ctaactttat tttaaaaggg cggaaacaat gaaaatcaaa attgaaaaag aaatgaatt    36300 acctgaactt atccaatggg cttgggataa ccccaagtta tcaggtaata aaagattcta    36360
ttcaaatgat gttgagcgca actgttttgt gacttttcat gttgatagca tcttatgtaa    36420
tgtgactgga tatgtatcaa ttaacgataa atttactgtt caagaggaga tataacaatg    36480
aaaatcaaag ttaaaaaga atgagatta gatgaattaa ttaaatgggc gcgagaaaat    36540
ccggatctat cacaaggaaa aatatttttt tcaacaggat ttagtgatgg attcgttcgt    36600
tttcatccaa atacaaataa gtgttcgacg tcaagtttta ttccaattga tatcccttc    36660 atagttgata ttgaaaaaga agtaacggaa gagactaagg ttgataggtt gattgaatta    36720
ttcgagattc aagaaggaga ctataactct acactatatg agaacactag tataaaagaa    36780
```

```
tgtttatatg gcagatgtgt gcctaccaaa gcattctaca tcttaaacga tgacctaact   36840
atgacgttaa tctggaaaga tggggagttg ctagtatgat gttgaaattt aaagcttggg   36900
ataaagataa aaaagttatg agtattattg acgaaatcga ttttaatagt gggtacattt   36960
tgatttcaac aggttataaa agtttcaatg aagtaaaact attacaatac acaggattta   37020
aagatgtgca cggtgtggag atttatgaag gggatattgt tcaagattgt tattcgagag   37080
aagtaagttt tatcgagttt aaagaaggag ccttttatat aacttttagc aatgtaactg   37140
aattactaag tgaaaatgac gatattattg aaattgttgg aaatattttt gaaaatgaga   37200
tgctattgga ggttatgaga tgacgttcac cttatcagat gaacaatata aaaatctttg   37260
tactaactct aacaagttat tagataaact tcacaaagca ttaaaagatc gtgaagagta   37320
caagaagcaa cgagatgagc ttattgggga tatagcgaag ttacgagatt gtaacaaaga   37380
tctagagaag aaagcaagcg catgggatag gtattgcaag agcgttgaaa aagatttaat   37440
aaacgaattc ggtaacgatg atgaaagagt taaattcgga atggaattaa acaataaaat   37500
ttttatggag gatgacacaa atgaataatc gcgaaaaaat cgaacagtcc gttattagtg   37560
ctagtgcgta taacggtaat gacacagagg ggttgctaaa agagattgag gacgtgtata   37620
agaaagcgca agcgtttgat gaaatacttg agggaatgac aaatgctatt caacattcag   37680
ttaaagaagg tattgaactt gatgaagcag tagggattat ggcaggtcaa gttgtctata   37740
aatatgagga ggaataggaa aatgactaac acattacaag taaaactatt atcaaaaaat   37800
gctagaatgc ccgaacgaaa tcataagacg gatgcaggtt atgacatatt ctcagctgaa   37860
actgtcgtac tcgaaccaca agaaaaagca gtgatcaaaa cagatgtagc tgtgagtata   37920
ccagagggct atgtcggact attaactagt cgtagtggtg taagtagtaa aacgtattta   37980
gtgattgaaa caggcaagat agacgcggga tatcatggca atttagggat taatatcaag   38040
aatgatgaag aacgtgatgg aatacccttt ttatatgatg atatagacgc tgaattagaa   38100
gatggattaa taagcatttt agatataaaa ggtaactatg tacaagatgg aagaggcata   38160
agaagagttt accaaatcaa caaaggcgat aaactagctc aattggttat cgtgcctata   38220
tggacaccgg aactaaagca agtggaggaa ttcgaaagtg tttcagaacg tggagcaaaa   38280
ggcttcggaa gtagcggagt gtaaagacat cttagatcga gttaaggagg ttttggggaa   38340
gtgacgcaat acttagtcac aacattcaaa gattcaacag gacgaccaca tgaacatatt   38400
actgtggcta gagataatca gacgtttaca gttattgagg cagagagtaa agaagaagcg   38460
aaagagaagt acgaggcaca agttaaaaga gatgcagtta ttaaagtggg tcagttgtat   38520
gaaaatataa gggagtgtgg gaaatgacgg atgttaaaat taaaactatt tcaggtggag   38580 tttatttttgt aaaaacagct gaacctttttg aaaaatatgt tgaaagaatg acgagtttta   38640
atggttatat ttacgcaagt actataatca gaaaccaac gtatattaaa acagatacga   38700
ttgaatcaat cacacttatt gaggagcatg ggaaatgaat cagctgagaa ttttattaca   38760
tgacggtagt agtttgatat tacatgaaga tgaattattt aacgaaatag tatttgtttt   38820
ggacaatttt agaaatgatg atgactattt aacgatagaa aaagattatg gcagagaact   38880
tgtattgaac aaaggttata tagttgggat caatgttgag gaggcagatg atgattaaca   38940
tacctaaaat gaaattcccg aaaaagtaca ctgaaataat caaaaaatat aaaaataaag   39000
cacctgaaga aaaggctaag attgaagatg atttttattaa agaaattaaa gataaagaca   39060
gtgaatttta cagtcctacg atggctaata tgaatgaata tgaattaagg gctatgttaa   39120
```

```
gaatgatgcc tagtttaatt gatactggag atgacaatga tgattaaaaa acttaaaaat  39180
atggatgggt tcgacatctt tattgttgga atactgtcat tattcggtat attcgcattg  39240
ctacttgtta tcacattgcc tatctataca gtggctagtt accaacacaa agaattacat  39300
caaggaacta ttacagataa atataacaag agacaagata aagaagacaa gttctatatt  39360
gtattagaca acaaacaagt cattgaaaat tccgacttat tattcaaaaa gaaatttgat  39420
agcgcagata tacaagctag gttaaaagta ggcgataagg tagaagttaa aacaatcggt  39480
tatagaatac acttttttaaa tttatatccg gtcttatacg aagtaaagaa ggtagataaa  39540
caatgattaa acaaatacta agactattat tcttactagc aatgtatgag ttaggtaagt  39600
atgtaactga gcaagtgtat attatgatga cggctaatga tgatgtagag gcgccgagtg  39660
attacgtctt tcgagcggag gtgagtgaat aatgagaata tttatttatg atttgatcgt  39720
tttgctgttt gctttcttaa tatccatata tattattgat gatggagtga taataaatgc  39780
attaggaatt tttggtatgt ataaaattat agattccttt tcagaaaata ttataaagag  39840
gtagataaaa atgaacgagc aaataatagg aagcatatat actttagcag gaggtgttgt  39900
gctttattca gttaaagaga ttttttaggta ttttacagat tctaacttac aacgtaaaaa  39960
aatcaattta gaacaaatat atccgatata tttagattgt tttaaaaagg ctaaaaagat  40020
gattggagct tatattattc caacagaaca gcatgaattt ttagatttttt ttgatattga  40080
agtctttaat aatttagata agcaaagtaa aaaagcgtat gaaaatgtta ttggatttag  40140
acaaatgatt aatttatcaa atagagttaa ggcaatggaa gattttaaga tgagtttcaa  40200
caatgaattt agtacaaatc agatttttttt taatccttct tttgttatgg aaacaattgc  40260
tattataaat gaatatcaaa aagatatatc ttatttaaaa aatataatta ataaaatgaa  40320
tgaaaataga gcttataatc atattgatag ttttatcact tcagagtacc gacgaaaaat  40380
aaacgattat aatctttatc ttgataaatt tgaagaacag tttagtcaaa agtttaaaat  40440
aaacagaact tcgataaaag aaagaattat tattaattta aacaagagga gatttaaatg  40500
atgtggatta ctatgactat tgtatttgct atattgctat tagtttgtat cagtattaat  40560
agtgatcgtg caagagagat acaagcactt agatatatga atgattatct acttgatgaa  40620
gtagttaaaa ctaaagggta caacgggtta gaagaataca ggattgaatt gaagcgaatg  40680
aataacgata ttaaaaagta atttatatta tcggaggtat tgcattgaat gataaagatt  40740
gagaaacacg atatcaaaaa gcttgaagaa tacattcagc acatcgataa ctatcgaaga  40800
gagttgaaga tgcgagaata tgaattactt gaaagtcatg aaccagataa tgcgggagct  40860
ggcaaaagta atttgccggg taacccgatt gaacgatgtg caataaagaa gtttagtgat  40920
aacaggtaca atacattaag aaatatagtt aacggtgtag atagattgat aggtgaaagt  40980
gatgaggata cgcttgagtt attaaggttt agatattggg attgtcctat tggttgttat  41040
gaatgggaag atatagcaca ttactttggt acaagtaaga caagtatatt acgtagaagg  41100
aatgcactga tcgataagtt agcaaagtat attggttatg tgtagcggac ttttacccta  41160
tgtaagtccg cattaaaaca gtttattatg ttagtatcag attaatattt aaagttatta  41220
aatgctaata cgacgcatga acaagaggcg catcactatg tgatgtgtct tttatttat  41280
gaggtatgaa catgttcaaa ctaattgtaa atacattact acacatcaag tatagatgag  41340
tcttgatact acttaagtta tataaggtga acattatga tgactaaaga cgaacgtata  41400
cgattctata agtctaaaga atggcaaata acaagaaaaa gagtgctaga aagagataat  41460
tatgaatgtc aacaatgtaa gagagacggc aagttaacga catatgacaa aagcaagcgt  41520
```

```
aagtcgttgg atgtagatca tatattatcg ctagaacatc atccggagtt tgctcatgac    41580
ttaaacaatt tagaaacact gtgtattaaa tgtcacaaca aaaagaaaa gagatttata    41640 aaaaaagaaa ataaatggaa agacgaaaaa tggtaaatac ccccgggtca aaaaatcaa    41700 aagcgatc                                                            41708
```

<210> SEQ ID NO 11
<211> LENGTH: 53
<212> TYPE: DNA
<213> ORGANISM: Synthetic Sequence

<400> SEQUENCE: 11
gatcccggtc gaccaagctt tacccatacg acgtcccaga ctacgccagc tga           53

<210> SEQ ID NO 12
<211> LENGTH: 53
<212> TYPE: DNA
<213> ORGANISM: Synthetic Sequence

<400> SEQUENCE: 12
agcttcagct ggcgtagtct gggacgtcgt atgggtaaag cttggtcgac cgg           53

<210> SEQ ID NO 13
<211> LENGTH: 21
<212> TYPE: DNA
<213> ORGANISM: Synthetic Sequence

<400> SEQUENCE: 13
aattctcgag taaaataaca t                                              21

<210> SEQ ID NO 14
<211> LENGTH: 37
<212> TYPE: DNA
<213> ORGANISM: Synthetic Sequence

<400> SEQUENCE: 14
aaatcaggtg actgttgaga aaaggaggcg gatcccg                             37

<210> SEQ ID NO 15
<211> LENGTH: 27
<212> TYPE: DNA
<213> ORGANISM: Synthetic Sequence

<400> SEQUENCE: 15
cgggatccat gaggggttcc gaagacg                                        27

<210> SEQ ID NO 16
<211> LENGTH: 24
<212> TYPE: DNA
<213> ORGANISM: Synthetic Sequence

<400> SEQUENCE: 16
gaaagtccaa attgtaagct tggg                                           24

<210> SEQ ID NO 17
<211> LENGTH: 27
<212> TYPE: DNA
<213> ORGANISM: Synthetic Sequence

<400> SEQUENCE: 17
ctcgaggaaa aggaggcgga tccgctt                                        27

```
<210> SEQ ID NO 18
<211> LENGTH: 237
<212> TYPE: PRT
<213> ORGANISM: Staphylococcus aureus bacteriophage 77

<400> SEQUENCE: 18

Met Thr His Asn Ile Glu Lys Arg Ile Asn Lys Leu Lys Thr Ser Gly
1               5                   10                  15

Asn Pro Lys Phe Lys Lys Leu Asp Ser Asp Ile His Tyr Leu Leu Lys
            20                  25                  30

Arg Phe Glu Gly Glu Lys Asn His Lys Gly Phe Tyr Pro Lys Phe Lys
        35                  40                  45

Gln Gly Glu Ile Val Phe Val Asp Phe Gly Ile Asn Val Asn Lys Glu
    50                  55                  60

Phe Ser Asn Ser His Phe Ala Ile Val Met Asn Lys Asn Asp Ser Asn
65                  70                  75                  80

Thr Glu Asp Ile Val Asn Val Ile Pro Leu Ser Ser Lys Glu Asn Lys
                85                  90                  95

Lys Tyr Leu Lys Met Asn Phe Asp Leu Lys Trp Glu Tyr Tyr Leu Arg
            100                 105                 110

Leu Phe Leu Asn Leu Ile Ser Ala Gln Asn Asn Ser Ala Ile Leu Lys
        115                 120                 125

Glu Val Phe Asp Lys Lys Tyr Gln Lys Asn Asn Thr Glu Phe Ile Thr
    130                 135                 140

Lys Asp Tyr Phe Ile Glu Phe Ile Ser Asp Ser Leu Glu Ile Glu Asn
145                 150                 155                 160

Lys Leu Asn Lys Ile Asp Arg Asn Ile Asn Asn Ile Val Ser Ala Ile
                165                 170                 175

Asp Lys Val Lys Lys Leu Lys Gly Asn Ser Tyr Ala Cys Ile Asn Ser
            180                 185                 190

Phe Gln Pro Ile Ser Lys Phe Arg Ile Arg Lys Val Leu Pro Gln Lys
        195                 200                 205

Ile Lys Asn Pro Val Ile Asp Ser Ser Asp Ile Met Leu Leu Ile Asn
    210                 215                 220

Arg Ile Asn Asn Asn Ile Leu Gln Ile Pro Asp Ile Arg
225                 230                 235

<210> SEQ ID NO 19
<211> LENGTH: 216
<212> TYPE: PRT
<213> ORGANISM: Staphylococcus aureus bacteriophage 77

<400> SEQUENCE: 19

Met Asn Glu Gln Ile Ile Gly Ser Ile Tyr Thr Leu Ala Gly Gly Val
1               5                   10                  15

Val Leu Tyr Ser Val Lys Glu Ile Phe Arg Tyr Phe Thr Asp Ser Asn
            20                  25                  30

Leu Gln Arg Lys Lys Ile Asn Leu Glu Gln Ile Tyr Pro Ile Tyr Leu
        35                  40                  45

Asp Cys Phe Lys Lys Ala Lys Lys Met Ile Gly Ala Tyr Ile Ile Pro
    50                  55                  60

Thr Glu Gln His Glu Phe Leu Asp Phe Asp Ile Glu Val Phe Asn
65                  70                  75                  80

Asn Leu Asp Lys Gln Ser Lys Lys Ala Tyr Glu Asn Val Ile Gly Phe
            85                  90                  95
```

```
Arg Gln Met Ile Asn Leu Ser Asn Arg Val Lys Ala Met Glu Asp Phe
            100                 105                 110

Lys Met Ser Phe Asn Asn Glu Phe Ser Thr Asn Gln Ile Phe Phe Asn
        115                 120                 125

Pro Ser Phe Val Met Glu Thr Ile Ala Ile Ile Asn Glu Tyr Gln Lys
    130                 135                 140

Asp Ile Ser Tyr Leu Lys Asn Ile Ile Asn Lys Met Asn Glu Asn Arg
145                 150                 155                 160

Ala Tyr Asn His Ile Asp Ser Phe Ile Thr Ser Glu Tyr Arg Arg Lys
                165                 170                 175

Ile Asn Asp Tyr Asn Leu Tyr Leu Asp Lys Phe Glu Gln Phe Ser
            180                 185                 190

Gln Lys Phe Lys Ile Asn Arg Thr Ser Ile Lys Glu Arg Ile Ile Ile
        195                 200                 205

Asn Leu Asn Lys Arg Arg Phe Lys
    210                 215

<210> SEQ ID NO 20
<211> LENGTH: 212
<212> TYPE: PRT
<213> ORGANISM: Staphylococcus aureus bacteriophage 77

<400> SEQUENCE: 20

Met Asn Glu Gln Ile Ile Gly Ser Ile Tyr Thr Leu Ala Gly Gly Val
  1               5                  10                  15

Val Lys Val Lys Glu Ile Phe Arg Tyr Phe Thr Asp Ser Asn Leu Gln
             20                  25                  30

Arg Lys Lys Ile Asn Leu Glu Gln Ile Tyr Pro Ile Tyr Leu Asp Cys
         35                  40                  45

Phe Lys Lys Ala Lys Lys Met Ile Gly Ala Tyr Ile Ile Pro Thr Glu
     50                  55                  60

Gln His Glu Phe Leu Asp Phe Phe Asp Ile Glu Val Phe Asn Asn Leu
 65                  70                  75                  80

Asp Lys Gln Ser Lys Lys Ala Tyr Glu Asn Val Ile Gly Phe Arg Gln
             85                  90                  95

Met Ile Asn Leu Ser Asn Arg Val Lys Ala Met Glu Asp Phe Lys Met
            100                 105                 110

Ser Phe Asn Asn Glu Phe Ser Thr Asn Gln Ile Phe Phe Asn Pro Ser
        115                 120                 125

Phe Val Met Ile Ala Ile Ile Asn Glu Tyr Gln Lys Asp Ile Ser Tyr
    130                 135                 140

Leu Lys Asn Ile Ile Asn Lys Met Asn Glu Asn Arg Ala Tyr Asn His
145                 150                 155                 160

Ile Asp Ser Phe Ile Thr Ser Glu Tyr Arg Arg Lys Ile Asn Asp Tyr
                165                 170                 175

Asn Leu Tyr Leu Asp Lys Phe Glu Glu Gln Phe Ser Gln Lys Phe Lys
            180                 185                 190

Ile Asn Arg Thr Ser Ile Lys Glu Arg Ile Ile Ile Asn Leu Asn Lys
        195                 200                 205

Arg Arg Phe Lys
    210

<210> SEQ ID NO 21
<211> LENGTH: 85
<212> TYPE: PRT
<213> ORGANISM: Staphylococcus aureus bacteriophage 77
```

```
<400> SEQUENCE: 21

Met Tyr Tyr Glu Ile Gly Glu Ile Ile Arg Lys Asn Ile His Val Asn
1               5                   10                  15

Gly Phe Asp Phe Lys Leu Phe Ile Leu Lys Gly His Met Gly Ile Ser
                20                  25                  30

Ile Gln Val Lys Asp Met Asn Asn Val Pro Ile Lys His Ala Tyr Val
            35                  40                  45

Val Asp Glu Asn Asp Leu Asp Met Ala Ser Asp Leu Phe Asn Gln Ala
        50                  55                  60

Ile Asp Glu Trp Ile Glu Glu Asn Thr Asp Gln Asp Arg Leu Ile Asn
65                  70                  75                  80

Leu Val Met Lys Trp
                85

<210> SEQ ID NO 22
<211> LENGTH: 86
<212> TYPE: PRT
<213> ORGANISM: Staphylococcus aureus bacteriophage 77

<400> SEQUENCE: 22

Met Tyr Tyr Glu Ile Gly Glu Ile Ile Arg Lys Asn Ile His Val Asn
1               5                   10                  15

Gly Phe Asp Phe Lys Leu Phe Ile Leu Lys Gly His Met Gly Ile Ser
                20                  25                  30

Ile Gln Val Lys Asp Met Asn Asn Val Pro Ile Lys His Ala Tyr Val
            35                  40                  45

Val Asp Glu Asn Asp Leu Asp Met Ala Ser Asp Leu Phe Asn Gln Ala
        50                  55                  60

Ile Asp Glu Trp Ile Glu Glu Asn Thr Asp Glu Gln Asp Arg Leu Ile
65                  70                  75                  80

Asn Leu Val Met Lys Trp
                85

<210> SEQ ID NO 23
<211> LENGTH: 53
<212> TYPE: PRT
<213> ORGANISM: Staphylococcus aureus bacteriophage 77

<400> SEQUENCE: 23

Met Ser Asn Ile Tyr Lys Ser Tyr Leu Val Ala Val Leu Cys Phe Thr
1               5                   10                  15

Val Leu Ala Ile Val Leu Met Pro Phe Leu Tyr Phe Thr Thr Ala Trp
                20                  25                  30

Ser Ile Ala Gly Phe Ala Ser Ile Ala Thr Phe Met Tyr Tyr Lys Glu
            35                  40                  45

Cys Phe Phe Lys Glu
        50

<210> SEQ ID NO 24
<211> LENGTH: 53
<212> TYPE: PRT
<213> ORGANISM: Staphylococcus aureus bacteriophage 77

<400> SEQUENCE: 24

Met Ser Asn Ile Tyr Lys Ser Tyr Leu Val Ala Val Leu Cys Phe Thr
1               5                   10                  15

Val Leu Ala Ile Val Leu Met Pro Phe Leu Tyr Phe Thr Thr Ala Trp
```

```
                 20                  25                  30

Ser Ile Ala Gly Phe Ala Ser Ile Ala Thr Phe Met Tyr Lys Glu
         35                  40                  45

Cys Phe Phe Lys Glu
         50

<210> SEQ ID NO 25
<211> LENGTH: 52
<212> TYPE: PRT
<213> ORGANISM: Staphylococcus aureus bacteriophage 77

<400> SEQUENCE: 25

Met Val Thr Lys Glu Phe Leu Lys Thr Lys Leu Glu Cys Ser Asp Met
  1               5                  10                  15

Tyr Ala Gln Lys Leu Ile Asp Glu Ala Gln Gly Asp Glu Asn Arg Leu
             20                  25                  30

Tyr Asp Leu Phe Ile Gln Lys Leu Ala Glu Arg His Thr Arg Pro Ala
         35                  40                  45

Ile Val Glu Tyr
     50

<210> SEQ ID NO 26
<211> LENGTH: 50
<212> TYPE: PRT
<213> ORGANISM: Staphylococcus aureus bacteriophage 77

<400> SEQUENCE: 26

Met Val Thr Lys Glu Phe Leu Lys Thr Lys Leu Glu Cys Ser Asp Met
  1               5                  10                  15

Tyr Ala Gln Lys Leu Ile Asp Glu Ala Gln Gly Asp Glu Asn Arg Leu
             20                  25                  30

Tyr Asp Leu Phe Ile Gln Lys Leu Ala Glu Arg His Trp Ala Ile Val
         35                  40                  45

Glu Tyr
     50

<210> SEQ ID NO 27
<211> LENGTH: 98
<212> TYPE: PRT
<213> ORGANISM: Staphylococcus aureus bacteriophage 77

<400> SEQUENCE: 27

Met Phe Asn Ile Lys Arg Lys Thr Glu Glu Val Lys Met Tyr Tyr Glu
  1               5                  10                  15

Ile Gly Glu Ile Ile Arg Lys Asn Ile His Val Asn Gly Phe Asp Phe
             20                  25                  30

Lys Leu Phe Ile Leu Lys Gly His Met Gly Ile Ser Ile Gln Val Lys
         35                  40                  45

Asp Met Asn Asn Val Pro Ile Lys His Ala Tyr Val Val Asp Glu Asn
     50                  55                  60

Asp Leu Asp Met Ala Ser Asp Leu Phe Asn Gln Ala Ile Asp Glu Trp
 65                  70                  75                  80

Ile Glu Glu Asn Thr Asp Glu Gln Asp Arg Leu Ile Asn Leu Val Met
                 85                  90                  95

Lys Trp

<210> SEQ ID NO 28
<211> LENGTH: 98
```

```
<212> TYPE: PRT
<213> ORGANISM: Staphylococcus aureus bacteriophage 77

<400> SEQUENCE: 28

Met Phe Asn Ile Lys Arg Lys Thr Glu Glu Val Lys Met Tyr Tyr Glu
 1               5                  10                  15

Ile Gly Glu Ile Ile Arg Lys Asn Ile His Val Asn Gly Phe Asp Phe
                20                  25                  30

Lys Leu Phe Ile Leu Lys Gly His Met Gly Ile Ser Ile Gln Val Lys
                35                  40                  45

Asp Met Asn Asn Val Pro Ile Lys His Ala Tyr Val Val Asp Glu Asn
 50                  55                  60

Asp Leu Asp Met Ala Ser Asp Leu Phe Asn Gln Ala Ile Asp Glu Trp
65                  70                  75                  80

Ile Glu Glu Asn Thr Asp Glu Gln Asp Arg Leu Ile Asn Leu Val Met
                85                  90                  95

Lys Trp

<210> SEQ ID NO 29
<211> LENGTH: 237
<212> TYPE: PRT
<213> ORGANISM: Staphylococcus aureus bacteriophage 77

<400> SEQUENCE: 29

Met Thr His Asn Ile Glu Lys Arg Ile Asn Lys Leu Lys Thr Ser Gly
 1               5                  10                  15

Asn Pro Lys Phe Lys Lys Leu Asp Ser Asp Ile His Tyr Leu Leu Lys
                20                  25                  30

Arg Phe Glu Gly Glu Lys Asn His Lys Gly Phe Tyr Pro Lys Phe Lys
                35                  40                  45

Gln Gly Glu Ile Val Phe Val Asp Phe Gly Ile Asn Val Asn Lys Glu
 50                  55                  60

Phe Ser Asn Ser His Phe Ala Ile Val Met Asn Lys Asn Asp Ser Asn
65                  70                  75                  80

Thr Glu Asp Ile Val Asn Val Ile Pro Leu Ser Ser Lys Glu Asn Lys
                85                  90                  95

Lys Tyr Leu Lys Met Asn Phe Asp Leu Lys Trp Glu Tyr Tyr Leu Arg
                100                 105                 110

Leu Phe Leu Asn Leu Ile Ser Ala Gln Asn Asn Ser Ala Ile Leu Lys
                115                 120                 125

Glu Val Phe Asp Lys Lys Tyr Gln Lys Asn Asn Thr Glu Phe Ile Thr
                130                 135                 140

Lys Asp Tyr Phe Ile Glu Phe Ile Ser Asp Ser Leu Glu Ile Glu Asn
145                 150                 155                 160

Lys Leu Asn Lys Ile Asp Arg Asn Ile Asn Asn Ile Val Ser Ala Ile
                165                 170                 175

Asp Lys Val Lys Lys Leu Lys Gly Asn Ser Tyr Ala Cys Ile Asn Ser
                180                 185                 190

Phe Gln Pro Ile Ser Lys Phe Arg Ile Arg Lys Val Leu Pro Gln Lys
                195                 200                 205

Ile Lys Asn Pro Val Ile Asp Ser Ser Asp Ile Met Leu Leu Ile Asn
                210                 215                 220

Arg Ile Asn Asn Asn Ile Leu Gln Ile Pro Asp Ile Arg
225                 230                 235
```

DNA SEQUENCES FROM *STAPHYLOCOCCUS AUREUS* BACTERIOPHAGE 77 THAT ENCODE ANTI-MICROBIAL POLYPEPTIDES

RELATED APPLICATIONS

This application claims the benefit of U.S. Provisional Application No. 60/110,992, filed Dec. 3, 1998, which is hereby incorporated by reference in its entirety, including drawings.

BACKGROUND OF THE INVENTION

This invention relates to the identification of antimicrobial agents and of microbial targets of such agents, and in particular to the isolation of bacteriophage DNA sequences, and their translated protein products, showing anti-microbial activity. The DNA sequences can be expressed in expression vectors. These expression constructs and the proteins produced therefrom can be used for a variety of purposes including therapeutic methods and identification of microbial targets.

The following description is provided to assist the understanding of the reader. None of the information provided or references cited is admitted to be prior art to the present invention.

The frequency and spectrum of antibiotic-resistant infections have, in recent years, increased in both the hospital and community. Certain infections have become essentially untreatable and are growing to epidemic proportions in the developing world as well as in institutional settings in the developed world. The staggering spread of antibiotic resistance in pathogenic bacteria has been attributed to microbial genetic characteristics, widespread use of antibiotic drugs and changes in society that enhance the transmission of drug-resistant organisms (for a review, see Cohen, 1992). This spread of drug resistant microbes is leading to ever-increasing morbidity, mortality and health-care costs.

There are over 160 antibiotics currently available for treatment of microbial infections, all based on a few basic chemical structures and targeting a small number of metabolic pathways: bacterial cell wall synthesis, protein synthesis, and DNA replication. Despite all these antibiotics, a person could succumb to an infection as a result of a resistant bacterial infection. Resistance now reaches all classes of antibiotics currently in use, including: β-lactams, fluoroquinolones, aminoglycosides, macrolide peptides, chloramphenicol, tetracyclines, rifampicin, folate inhibitors, glycopeptides, and mupirocin. There is thus a need for new antibiotics, and this need will not subside given the ability bacteria have to overcome each new agent synthesized. It is also likely that targeting new pathways will play an important role in discovery of these new antibiotics. In fact, a number of crucial cellular pathways, such as secretion, cell division, and many metabolic functions, remain untargeted today.

Most major pharmaceutical companies have on-going drug discovery programs for novel anti-microbials. These are based on screens for small molecule inhibitors (e.g., natural products, bacterial culture media, libraries of small molecules, combinatorial chemistry) of crucial metabolic pathways of the micro-organism of interest. The screening process is largely for cytotoxic compounds and in most cases is not based on a known mechanism of action of the compounds. Classical drug screening programs are being exhausted and many of these pharmaceutical companies are looking towards rational drug design programs. Several small to mid-size biotechnology companies, as well as large pharmaceutical companies, have developed systematic high-throughput sequencing programs to decipher the genetic code of specific micro-organisms of interest. The goal is to identify, through sequencing, unique biochemical pathways or intermediates that are unique to the microorganism. Knowledge of the function of these bacterial genes, may form the rationale for a drug discovery program based on the mechanism of action of the identified enzymes/proteins. However, one of the most critical steps in this approach is the ascertainment that the identified proteins and biochemical pathways are 1) non-redundant and essential for bacterial survival, and 2) constitute suitable and accessible targets for drug discovery. These two issues are not easily addressed since to date, 18 prokaryotic genomes have been sequenced and 200 sequenced genomes are expected by the year 2000. For a majority of the sequenced genomes, less than 50% of the open reading frames (ORFs) have been linked to a known function. Even with the genome of *Escherichia coli* (*E. coli*), the most extensively studied bacterium, less than two-thirds of the annotated protein coding genes showed significant similarity to genes with ascribed functions (Rusterholtz and Pohlschroder, 1999). Thus considerable work must be undertaken to identify appropriate bacterial targets for drug screening.

SUMMARY OF THE INVENTION

The present invention is based on the identification of, and demonstration that, specific DNA sequences of a bacteriophage, when introduced into a host bacterium can kill, or inhibit growth, of the host. Thus, these DNA sequences are anti-microbial agents. Information based on these DNA sequences can be utilized to develop peptide mimetics that can also function also as anti-microbials. The identification of the host bacterial proteins, targeted by the anti-microbial bacteriophage DNA sequences, can provide novel targets for drug design and compound screening.

In this regard, the terms "inhibit", "inhibition", "inhibitory", and "inhibitor" all refer to a function of reducing a biological activity or function. Such reduction in activity or function can, for example, be in connection with a cellular component (e.g., an enzyme), or in connection with a cellular process (e.g., synthesis of a particular protein), or in connection with an overall process of a cell (e.g., cell growth). In reference to cell growth, the inhibitory effects may be bactericidal (killing of bacterial cells) or bacteriostatic (i.e., stopping or at least slowing bacterial cell growth). The latter slows or prevents cell growth such that fewer cells of the strain are produced relative to uninhibited cells over a given time period. From a molecular standpoint, such inhibition may equate with a reduction in the level of, or elimination of, the transcription and/or translation of a specific bacterial target(s), or reduction or elimination of activity of a particular target biomolecule.

In a first aspect the invention provides methods for identifying a target for antibacterial agents by identifying the bacterial target(s) of at least one inhibitory gene product, e.g., protein from ORFs 17, 19, 43, 102, 104, and 182 of bacteriophage 77 or a homologous product. Such identification allows the development of antibacterial agents active on such targets. Preferred embodiments for identifying such targets involve the identification of binding of target and phage ORF products to one another. The target molecule may be a bacterial protein or other bacterial biomolecule, e.g., a nucleotprotein, a nucleic acid, a lipid or lipid-containing molecule, a nucleoside or nucleoside derivative, a polysaccharide or polysaccharide-containing molecule, or a peptidoglycan. The phage ORF products may be subportions of a larger ORF product that also binds the host target. Exemplary approaches are described below in the Detailed Description.

Additionally, the invention provides methods for identifying targets for antibacterial agents by identifying homologs of a *Staphylococcus aureus* target of a bacteriophage ORFs 17, 19, 43, 102, 104, or 182 product. Such homologs may be utilized in the various aspects and embodiments described herein.

The term "fragment" refers to a portion of a larger molecule or assembly. For proteins, the term "fragment" refers to a molecule which includes at least 5 contiguous amino acids from the reference polypeptide or protein, preferably at least 6, 8, 10, 12, 15, 20, 30, 50 or more contiguous amino acids. In connection with oligo- or polynucleotides, the term "fragment" refers to a molecule which includes at least 15 contiguous nucleotides from a reference polynucleotide, preferably at least 18, 21, 24, 30, 36, 45, 60, 90, 150, or more contiguous nucleotides. Also in preferred embodiments, the fragment has a length in a range with the minimum as described above and a maximum which is no more than 90% of the length (or contains that percent of the contiguous amino acids or nucleotides) of the larger molecule (e.g., of the specified ORF), in other embodiments, the upper limit is no more than 60, 70, or 80% of the length of the larger molecule.

Stating that an agent or compound is "active on" a particular cellular target, such as the product of a particular gene, means that the target is an important part of a cellular pathway which includes that target and that the agent acts on that pathway. Thus, in some cases the agent may act on a component upstream or downstream of the stated target, including a regulator of that pathway or a component of that pathway. In general, an antibacterial agent is active on an essential cellular function, often on a product of an essential gene.

By "essential", in connection with a gene or gene product, is meant that the host cannot survive without, or is significantly growth compromised, in the absence or depletion of functional product. An "essential gene" is thus one that encodes a product that is beneficial, or preferably necessary, for cellular growth in vitro in a medium appropriate for growth of a strain having a wild-type allele corresponding to the particular gene in question. Therefore, if an essential gene is inactivated or inhibited, that cell will grow significantly more slowly or even not at all. Preferably growth of a strain in which such a gene has been inactivated will be less than 20%, more preferably less than 10%, most preferably less than 5% of the growth rate of the wild-type, or not at all, in the growth medium. Preferably, in the absence of activity provided by a product of the gene, the cell will not grow at all or will be non-viable, at least under culture conditions similar to normal in vivo growth conditions: For example, absence of the biological activity of certain enzymes involved in bacterial cell wall synthesis can result in the lysis of cells under normal osmotic conditions, even though protoplasts can be maintained under controlled osmotic conditions. Preferably, but not necessarily, if such a gene is inhibited, e.g., with an antibacterial agent or a phage product, the growth rate of the inhibited bacteria will be less than 50%, more preferably less than 30%, still more preferably less than 20%, and most preferably less than 10% of the growth rate of the uninhibited bacteria. As recognized by those skilled in the art, the degree of growth inhibition will generally depend on the concentration of the inhibitory agent. In the context of the invention, essential genes are generally the preferred targets of antimicrobial agents. Essential genes can encode target molecules directly or can encode a product involved in the production, modification, or maintenance of a target molecule.

A "target" refers to a biomolecule that can be acted on by an exogenous agent, thereby modulating, preferably inhibiting, growth or viability of a cell. In most cases such a target will be a nucleic acid sequence or molecule, or a polypeptide or protein. However, other types of biomolecules can also be targets, e.g., membrane lipids and cell wall structural components.

The term "bacterium" refers to a single bacterial strain, and includes a single cell, and a plurality or population of cells of that strain unless clearly indicated to the contrary. In reference to bacteria or bacteriophage, the term "strain" refers to bacteria or phage having a particular genetic content. The genetic content includes genomic content as well as recombinant vectors. Thus, for example, two otherwise identical bacterial cells would represent different strains if each contained a vector, e.g., a plasmid, with different phage ORF inserts.

In the context of the phage nucleic acid sequences, e.g., gene sequences, of this invention, the terms "homolog" and "homologous" denote nucleotide sequences from different bacteria or phage strains or species or from other types of organisms that have significantly related nucleotide sequences, and consequently significantly related encoded gene products, preferably having related function. Homologous gene sequences or coding sequences have at least 70% sequence identity (as defined by the maximal base match in a computer-generated alignment of two or more nucleic acid sequences) over at least one sequence window of 48 nucleotides, more preferably at least 80 or 85%, still more preferably at least 90%, and most preferably at least 95%. The polypeptide products of homologous genes have at least 35% amino acid sequence identity over at least one sequence window of 18 amino acid residues, more preferably at least 40%, still more preferably at least 50% or 60%, and most preferably at least 70%, 80%, or 90%. Preferably, the homologous gene product is also a functional homolog, meaning that the homolog will functionally complement one or more biological activities of the product being compared. For nucleotide or amino acid sequence comparisons where a homology is defined by a % sequence identity, the percentage is determined using BLAST programs (with default parameters (Altschul et al., 1997, "Gapped BLAST and PSI-BLAST: a new generation of protein database search programs, Nucleic Acid Res. 25:3389–3402). Any of a variety of algorithms known in the art which provide comparable results can also be used, preferably using default parameters. Performance characteristics for three different algorithms in homology searching is described in Salamov et al., 1999, "Combining sensitive database searches with multiple intermediates to detect distant homologues." *Protein Eng.* 12:95–100. Another exemplary program package is the GCG™ package from the University of Wisconsin.

Homologs may also or in addition be characterized by the ability of two complementary nucleic acid strands to hybridize to each other under appropriately stringent conditions. Hybridizations are typically and preferably conducted with probe-length nucleic acid molecules, preferably 20–100 nucleotides in length. Those skilled in the art understand how to estimate and adjust the stringency of hybridization conditions such that sequences having at least a desired level of complementarity will stably hybridize, while those having lower complementarity will not. For examples of hybridization conditions and parameters, see, e.g., Maniatis, T. et al. (1989) *Molecular Cloning: A Laboratory Manual*, Cold Spring Harbor University Press, Cold Spring, N.Y.; Ausubel, F. M. et al. (1994) *Current Protocols in Molecular Biology*. John Wiley & Sons, Secaucus, N.J. Homologs and homologous gene sequences may thus be identified using any nucleic acid sequence of interest, including the phage ORFs and bacterial target genes of the present invention.

A typical hybridization, for example, utilizes, besides the labeled probe of interest, a salt solution such as 6×SSC (NaCl and Sodium Citrate base) to stabilize nucleic acid strand interaction, a mild detergent such as 0.5% SDS, together with other typical additives such as Denhardt's solution and salmon sperm DNA. The solution is added to the immobilized sequence to be probed and incubated at suitable temperatures to preferably permit specific binding while minimizing nonspecific binding. The temperature of the incubations and ensuing washes is critical to the success and clarity of the hybridization. Stringent conditions employ relatively higher temperatures, lower salt concentrations, and/or more detergent than do non-stringent conditions. Hybridization temperatures also depend on the length, complementarity level, and nature (i.e., "GC content") of the sequences to be tested. Typical stringent hybridizations and washes are conducted at temperatures of at least 40° C., while lower stringency hybridizations and washes are typically conducted at 37° C. down to room temperature (~25° C.). One of ordinary skill in the art is aware that these conditions may vary according to the parameters indicated above, and that certain additives such as formamide and dextran sulphate may also be added to affect the conditions.

By "stringent hybridization conditions" is meant hybridization conditions at least as stringent as the following: hybridization in 50% formamide, 5×SSC, 50 mM $NaH_2PO_4$, pH 6.8, 0.5% SDS, 0.1 mg/mL sonicated salmon sperm DNA, and 5× Denhart's solution at 42° C. overnight; washing with 2×SSC, 0.1% SDS at 45° C.; and washing with 0.2×SSC, 0.1% SDS at 45° C.

Homologous nucleotide sequences will distinguishably hybridize with a reference sequence with up to three mismatches in ten (i.e., at least 70% base match in two sequences of equal length). Preferably, the allowable mismatch level is up to two mismatches in 10, or up to one mismatch in ten, more preferably up to one mismatch in twenty. (Those ratios can, of course, be applied to larger sequences.)

Preferred embodiments involve identification of binding between ORF product and bacterial cellular component that include methods for distinguishing bound molecules, for example, affinity chromatography, immunoprecipitation, crosslinking, and/or genetic screen methods that permit protein:protein interactions to be monitored. One of skill in the art is familiar with these techniques and common materials utilized (see, e.g., Coligan, J. et al. (eds.) (1995) *Current Protocols in Protein Science*. John Wiley & Sons, Secaucus, N.J.).

Genetic screening for the identification of protein:protein interactions typically involves the co-introduction of both a chimeric bait nucleic acid sequence (here, the phage ORF to be tested) and a chimeric target nucleic acid sequence that, when co-expressed and having affinity for one another in a host cell, stimulate reporter gene expression to indicate the relationship. A "positive" can thus suggest a potential inhibitory effect in bacteria. This is discussed in further detail in the Detailed Description section below. In this way, new bacterial targets can be identified that are inhibited by specific phage ORF products or derivatives, fragments, mimetics, or other molecules.

Other embodiments involve the identification and/or utilization of a target which is mutated at the site of phage 77 protein interaction but still functional in the cell by virtue of their host's relatively unresponsive nature in the presence of expression of ORFs previously identified as inhibitory to the non-mutant or wild-type strain. Such mutants have the effect of protecting the host from an inhibition that would otherwise occur (e.g., by competing for binding with the phage ORF product) and indirectly allow identification of the precise responsible target. The identified target can then be used, e.g., for follow-up studies and anti-microbial development. In certain embodiments, rescue from inhibition occurs under conditions in which a bacterial target or mutant target is highly expressed. This is performed, for example, through coupling of the sequence with regulatory element promoters, e.g., as known in the art, which regulate expression at levels higher than wild-type, e.g., at a level sufficiently higher that the inhibitor can be competitively bound to the highly expressed target such that the bacterium is detectably less inhibited.

Identification of the bacterial target can involve identification of a phage-specific site of action. This can involve a newly identified target, or a target where the phage site of action differs from the site of action of a previously known antibacterial agent or inhibitor. For example, phage T7 genes 0.7 and 2.0 target the host RNA polymerase, which is also the cellular target for the antibacterial agent, rifampin. To the extent that a phage product is found to act at a different site than previously described inhibitors, aspects of the present invention can utilize those new, phage-specific sites for identification and use of new agents. The site of action can be identified by techniques known to those skilled in the art, for example, by mutational analysis, binding competition analysis, and/or other appropriate techniques.

Once a bacterial host target or mutant target sequence has been identified, it too can be conveniently sequenced, sequence analyzed (e.g., by computer), and the underlying gene(s), and corresponding translated product(s) further characterized. Preferred embodiments include such analysis and identification. Preferably such a target has not previously been identified as an appropriate target for antibacterial action.

Also in preferred embodiments in which the bacterial target is a polypeptide or nucleic acid molecule, the identification of a bacterial target of a phage ORF product or fragment includes identification of a cellular and/or biochemical function of the bacterial target. As understood by those skilled in the art, this can, for example, include identification of function by identification of homologous polypeptides or nucleic acid molecules having known function, or identification of the presence of known motifs or sequences corresponding to known function. Such identifications can be readily performed using sequence comparison computer software, such as the BLAST programs and similar other programs and sequence and motif databases.

In embodiments involving expression of a phage ORF in a bacterial strain, in preferred embodiments that expression is inducible. By "inducible" is meant that expression is absent or occurs at a low level until the occurrence of an appropriate environmental stimulus provides otherwise. For the present invention such induction is preferably controlled by an artificial environmental change, such as by contacting a bacterial strain population with an inducing compound (i.e., an inducer). However, induction could also occur, for example, in response to build-up of a compound produced by the bacteria in the bacterial culture, e.g., in the medium. As uncontrolled or constitutive expression of inhibitory ORFs can severely compromise bacteria to the point of eradication, such expression is therefore undesirable in many cases because it would prevent effective evaluation of the strain and inhibitor being studied. For example, such uncontrolled expression could prevent any growth of the strain following insertion of a recombinant ORF, thus preventing determination of effective transfection or transformation. A controlled or inducible expression is therefore advantageous and is generally provided through the provision of suitable regulatory elements, e.g., promoter/operator sequences that can be conveniently transcriptionally linked to a coding sequence to be evaluated. In most cases, the vector will also contain sequences suitable for efficient replication of the vector in the same or different host cells and/or sequences allowing selection of cells containing the vector, i.e., "selectable markers." Further, preferred vectors include convenient primer sequences flanking the cloning region from which PCR and/or sequencing may be performed. In preferred embodiments where the purification of phage product is desired, preferably the bacterium or other cell type does not produce a target for the inhibitory product, or is otherwise resistant to the inhibitory product.

In preferred embodiments, the target of the phage ORF product or fragment is identified from a bacterial animal pathogen, preferably a mammalian pathogen, more preferably a human pathogen, and is preferably a gene or gene product of such a pathogen. Also in preferred embodiments, the target is a gene or gene product, where the sequence of the target is homologous to a gene or gene product from such a pathogen as identified above.

As used herein, the term "mammal" has its usual biological meaning, and particularly includes bovines, swine, dogs, cats, and humans.

Other aspects of the invention provide isolated, purified, or enriched specific phage nucleic acid and amino acid sequences, subsequences, and homologs thereof from or corresponding to ORFs 17, 19, 43, 102, 104, and 182 from bacteriophage 77 (*Staphylococcus aureus* host bacterium). Such nucleotide sequences are at least 15 nucleotides in length, preferably at least 18, 21, 24, or 27 nucleotides in length, more preferably at least 30, 50, or 90 nucleotides in length. In certain embodiments, longer nucleic acids are preferred, for example those of at least 120, 150, 200, 300, 600, 900 or more nucleotides. Such sequences can, for example, be amplification oligonucleotides (e.g., PCR primers), oligonucleotide probes, sequences encoding a portion or all of a phage-encoded protein, or a fragment or all of a phage-encoded protein. In preferred embodiments, the nucleic acid sequence or amino acid sequence contains a sequence which has a lower length as specified above, and an upper-length limit which is no more than 50, 60, 70, 80, or 90% of the length of the full-length ORF or ORF product. The upper-length limit can also be expressed in terms of the number of base pairs of the ORF (coding region).

As it is recognized that alternate codons will encode the same amino acid for most amino acids due to the degeneracy of the genetic code, the sequences of this aspect includes nucleic acid sequences utilizing such alternate codon usage for one or more codons of a coding sequence. For example, all four nucleic acid sequences GCT, GCC, GCA, and GCG encode the amino acid, alanine. Therefore, if for an amino acid there exists an average of three codons, a polypeptide of 100 amino acids in length will, on average, be encoded by $3^{100}$, or $5 \times 10^{47}$, nucleic acid sequences. Thus, a nucleic acid sequence can be modified (e.g., a nucleic acid sequence from a phage as specified above) to form a second nucleic acid sequence encoding the same polypeptide as encoded by the first nucleic acid sequence using routine procedures and without undue experimentation. Thus, all possible nucleic acid sequences that encode the amino acid sequences encoded by the phage 77 ORFs 17, 19, 43, 102, 104, and 182, as if all were written out in full, taking into account the codon usage, especially that preferred in the host bacterium.

The alternate codon descriptions are available in common textbooks, for example, Stryer, BIOCHEMISTRY $3^{rd}$ ed., and Lehninger, BIOCHEMISTRY $3^{rd}$ ed. Codon preference tables for various types of organisms are available in the literature. Because of the number of sequence variations involving alternate codon usage, for the sake of brevity, individual sequences are not separately listed herein. Instead the alternate sequences are described by reference to the natural sequence with replacement of one or more (up to all) of the degenerate codons with alternate codons from the alternate codon table (Table 2), preferably with selection according to preferred codon usage for the normal host organism or a host organism in which a sequence is intended to be expressed. Those skilled in the art also understand how to alter the alternate codons to be used for expression in organisms where certain codons code differently than shown in the "universal" codon table.

For amino acid sequences, sequences contain at least 5 peptide-linked amino acid residues, and preferably at least 6, 7, 10, 15, 20, 30, or 40, amino acids having identical amino acid sequence as the same number of contiguous amino acid residues in a phage ORF 17, 19, 43, 102, 104, or 182 product. In some cases longer sequences may be preferred, for example, those of at least 50, 70, or 100 amino acids in length. In preferred embodiments, the sequence has bacteria-inhibiting function when expressed or otherwise present in a bacterial cell which is a host for the bacteriophage from which the sequence was derived.

By "isolated" in reference to a nucleic acid is meant that a naturally occurring sequence has been removed from its normal cellular (e.g., chromosomal) environment or is synthesized in a non-natural environment (e.g. artificially synthesized). Thus, the sequence may be in a cell-free solution or placed in a different cellular environment. The term does not imply that the sequence is the only nucleotide chain present, but that it is essentially free (about 90–95% pure at least) of non-nucleotide material naturally associated with it, and thus is distinguished from isolated chromosomes.

The term "enriched" means that the specific DNA or RNA sequence constitutes a significantly higher fraction (2–5 fold) of the total DNA or RNA present in the cells or solution of interest than in normal or diseased cells or in cells from which the sequence was originally taken. This could be caused by a person by preferential reduction in the amount of other DNA or RNA present, or by a preferential increase in the amount of the specific DNA or RNA sequence, or by a combination of the two. However, it should be noted that enriched does not imply that there are no other DNA or RNA sequences present, just that the relative amount of the sequence of interest has been significantly increased.

The term "significant" is used to indicate that the level of increase is useful to the person making such an increase and an increase relative to other nucleic acids of about at least 2-fold, more preferably at least 5- to 10-fold or even more. The term also does not imply that there is no DNA or RNA from other sources. The other source DNA may, for example, comprise DNA from a yeast or bacterial genome, or a cloning vector such as pUC119. This term distinguishes from naturally occurring events, such as viral infection, or tumor type growths, in which the level of one mRNA may be naturally increased relative to other species of mRNA. That is, the term is meant to cover only those situations in which a person has intervened to elevate the proportion of the desired nucleic acid.

It is also advantageous for some purposes that a nucleotide sequence be in purified form. The term "purified" in reference to nucleic acid does not require absolute purity (such as a homogeneous preparation). Instead, it represents an indication that the sequence is relatively more pure than in the natural environment (compared to the natural level, this level should be at least 2–5 fold greater, e.g., in terms of mg/mL). Individual clones isolated from a genomic or cDNA library may be purified to electrophoretic homogeneity. The claimed DNA molecules obtained from these clones could be obtained directly from total DNA or from total RNA. cDNA clones are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process which includes the construction of a cDNA library from mRNA and isolation of distinct cDNA clones yields an approximately $10^6$-fold purification of the native message. Thus, purification of at least one order of magnitude, preferably two or three orders, and more preferably four or five orders of magnitude is expressly contemplated. A genomic library can be used in the same way and yields the same approximate levels of purification.

The terms "isolated", "enriched", and "purified" with respect to the nucleic acids, above, may similarly be used to denote the relative purity and abundance of polypeptides (multimers of amino acids joined one to another by $\alpha$-carboxyl:$\alpha$-amino group (peptide) bonds). These, too, may be stored in, grown in, screened in, and selected from libraries using biochemical techniques familiar in the art. Such polypeptides may be natural, synthetic or chimeric and may be extracted using any of a variety of methods, such as antibody immunoprecipitation, other "tagging" techniques, conventional chromatography and/or electrophoretic methods. Some of the above utilize the corresponding nucleic acid sequence.

As indicated above, aspects and embodiments of the invention are not limited to entire genes and proteins. The invention also provides and utilizes fragments and portions thereof, preferably those which are "active" in the inhibitory sense described above. Such peptides or oligopeptides and oligo or polynucleotides have preferred lengths as specified above for nucleic acid and amino acid sequences from phage; corresponding recombinant constructs can be made to express the encoded same. Also included are homologous sequences and fragments thereof.

The nucleotide and amino acid sequences identified herein are believed to be correct, however, certain sequences may contain a small percentage of errors, e.g., 1–5%. In the event that any of the sequences have errors, the corrected sequences can be readily provided by one skilled in the art using routine methods. For example, the nucleotide sequences can be confirmed or corrected by obtaining and culturing the relevant phage, and purifying phage genomic nucleic acids. A region or regions of interest can be amplified, e.g., by PCR from the appropriate genomic template, using primers based on the described sequence. The amplified regions can then be sequenced using any of the available methods (e.g., a dideoxy termination method, for example, using commercially available products). This can be done redundantly to provide the corrected sequence or to confirm that the described sequence is correct. Alternatively, a particular sequence or sequences can be identified and isolated as an insert or inserts in a phage genomic library and isolated, amplified, and sequenced by standard methods. Confirmation or correction of a nucleotide sequence for a phage gene provides an amino acid sequence of the encoded product by merely reading off the amino acid sequence according to the normal codon relationships and/or expressed in a standard expression system and the polypeptide product sequenced by standard techniques. The sequences described herein thus provide unique identification of the corresponding genes and other sequences, allowing those sequences to be used in the various aspects of the present invention. Confirmation of a phage ORF encoded amino acid sequence can also be confirmed by constructing a recombinant vector from which the ORF can be expressed in an appropriate host (e.g., *E. coli*), purified, and sequenced by conventional protein sequencing methods.

In other aspects the invention provides recombinant vectors and cells harboring phage 77 ORF 17, 19, 43, 102, 104, or 182 or portions thereof, or bacterial target sequences described herein, preferably where the phage or bacterial sequence is inserted in a recombinant vector. As understood by those skilled in the art, vectors may assume different forms, including, for example, plasmids, cosmids, and virus-based vectors. See, e.g., Maniatis, T. et al. (1989) *Molecular Cloning: A Laboratory Manual*, Cold Spring Harbor University Press, Cold Spring, N.Y.; See also, Ausubel, F. M. et al. (eds.) (1994) *Current Protocols in Molecular Biology*. John Wiley & Sons, Secaucus, N.J.

In preferred embodiments, the vectors will be expression vectors, preferably shuttle vectors that permit cloning, replication, and expression within bacteria. An "expression vector" is one having regulatory nucleotide sequences containing transcriptional and translational regulatory information that controls expression of the nucleotide sequence in a host cell. Preferably the vector is constructed to allow amplification from vector sequences flanking an insert locus. In certain embodiments, the expression vectors may additionally or alternatively support expression, and/or replication in animal, plant and/or yeast cells due to the presence of suitable regulatory sequences, e.g., promoters, enhancers, 3' stabilizing sequences, primer sequences, etc. In preferred embodiments, the promoters are inducible and specific for the system in which expression is desired, e.g., bacteria, animal, plant, or yeast. The vectors may optionally encode a "tag" sequence or sequences to facilitate protein purification or protein detection. Convenient restriction enzyme cloning sites and suitable selective marker(s) are also optionally included. Such selective markers can be, for example, antibiotic resistance markers or markers which supply an essential nutritive growth factor to an otherwise deficient mutant host, e.g., tryptophan, histidine, or leucine in the Yeast Two-Hybrid systems described below.

The term "recombinant vector" relates to a single- or double-stranded circular nucleic acid molecule that can be transfected into cells and replicated within or independently of a cell genome. A circular double-stranded nucleic acid molecule can be cut and thereby linearized upon treatment with appropriate restriction enzymes. An assortment of nucleic acid vectors, restriction enzymes, and the knowledge of the nucleotide sequences cut by restriction enzymes are readily available to those skilled in the art. A nucleic acid molecule encoding a desired product can be inserted into a vector by cutting the vector with restriction enzymes and ligating the two pieces together. Preferably the vector is an expression vector, e.g., a shuttle expression vector as described above.

By "recombinant cell" is meant a cell possessing introduced or engineered nucleic acid sequences, e.g., as described above. The sequence may be in the form of or part of a vector or may be integrated into the host cell genome. Preferably the cell is a bacterial cell.

In preferred embodiments, the inserted nucleic acid sequence corresponding to at least a portion of a bacteriophage 77 ORF 17, 19, 43, 102, 104, and 182 gene product has a length as specified for the isolated purified or enriched nucleic acid sequences in an aspect above.

In another aspect, the invention also provides methods for identifying and/or screening compounds "active on" at least one bacterial target of a bacteriophage inhibitor protein or RNA. Preferred embodiments involve contacting bacterial target proteins with a test compound, and determining whether the compound binds to or reduces the level of activity of the bacterial target, e.g., a bacterial protein. Preferably this is done in vivo under approximately physiological conditions. The compounds that can be used may be large or small, synthetic or natural, organic or inorganic, proteinaceous or non-proteinaceous. In preferred embodiments, the compound is a peptidomimetic, as described herein, a bacteriophage inhibitor protein or fragment or derivative thereof, preferably an "active portion", or a small molecule. In particular embodiments, the methods include the identification of bacterial targets as described above or otherwise described herein. Preferably the fragment of a bacteriophage inhibitor protein includes less than 80% of an intact bacteriophage inhibitor protein. Preferably, the at least one target includes a plurality of different targets of bacteriophage inhibitor proteins, preferably a plurality of different targets. The plurality of targets can be in or from a plurality of different bacteria, but preferably is from a single bacterial species.

In embodiments involving binding assays, preferably binding is to a fragment or portion of a bacterial target protein, where the fragment includes less than 90%, 80%, 70%, 60%, 50%, 40%, or 30% of an intact bacterial target protein. Preferably, the at least one bacterial target includes a plurality of different targets of bacteriophage inhibitor proteins, preferably a plurality of different targets. The plurality of targets can be in or from a plurality of different bacteria, but preferably is from a single bacterial species.

A "method of screening" refers to a method for evaluating a relevant activity or property of a large plurality of compounds, rather than just one or a few compounds. For example, a method of screening can be used to conveniently test at least 100, more preferably at least 1000, still more preferably at least 10,000, and most preferably at least 100,000 different compounds, or even more.

In the context of this invention, the term "small molecule" refers to compounds having molecular mass of less than 3000 Daltons, preferably less than 2000 or 1500, still more preferably less than 1000, and most preferably less than 600 Daltons. Preferably but not necessarily, a small molecule is not an oligopeptide.

In a related aspect or in preferred embodiments, the invention provides a method of screening for potential antibacterial agents by determining whether any of a plurality of compounds, preferably a plurality of small molecules, is active on at least one target of a bacteriophage inhibitor protein or RNA. Preferred embodiments include those described for the above aspect, including embodiments which involve determining whether one or more test compounds bind to or reduce the level of activity of a bacterial target, and embodiments which utilize a plurality of different targets as described above.

The identification of bacteria-inhibiting phage ORFs and their encoded products also provides a method for identifying an active portion of such an encoded product. This also provides a method for identifying a potential antibacterial agent by identifying such an active portion of a phage ORF or ORF product. In preferred embodiments, the identification of an active portion involves one or more of mutational analysis, deletion analysis, or analysis of fragments of such products. The method can also include determination of a 3-dimensional structure of an active portion, such as by analysis of crystal diffraction patterns. In further embodiments, the method involves constructing or synthesizing a peptidomimetic compound, where the structure of the peptidomimetic compound corresponds to the structure of the active portion.

In this context, "corresponds" means that the peptidomimetic compound structure has sufficient similarities to the structure of the active portion that the peptidomimetic will interact with the same molecule as the phage protein and preferably will elicit at least one cellular response in common which relates to the inhibition of the cell by the phage protein.

The methods for identifying or screening for compounds or agents active on a bacterial target of a phage-encoded inhibitor can also involve identification of a phage-specific site of action on the target.

An "active portion" as used herein denotes an epitope, a catalytic or regulatory domain, or a fragment of a bacteriophage inhibitor protein that is responsible for, or a significant factor in, bacterial target inhibition. The active portion preferably may be removed from its contiguous sequences and, in isolation, still effect inhibition.

By "mimetic" is meant a compound structurally and functionally related to a reference compound that can be natural, synthetic, or chimeric. In terms of the present invention, a "peptidomimetic," for example, is a compound that mimics the activity-related aspects of the 3-dimensional structure of a peptide or polypeptide in a non-peptide compound, for example mimics the structure of a peptide or active portion of a phage- or bacterial ORF-encoded polypeptide.

A related aspect provides a method for inhibiting a bacterial cell by contacting the bacterial cell with a compound active on a bacterial target of a bacteriophage inhibitor protein or RNA encoded by bacteriophage 77 ORF 17, 19, 43, 102, 104, or 182, where the target was uncharacterized. In preferred embodiments, the compound is such a protein, or a fragment or derivative thereof; a structural mimetic, e.g., a peptidomimetic, of such a protein or fragment; a small molecule; the contacting is performed in vitro, the contacting is performed in vivo in an infected or at risk organism, e.g., an animal such as a mammal or bird, for example, a human, or other mammal described herein, or in a plant.

In the context of this invention, the term "bacteriophage inhibitor protein" refers to a protein encoded by a bacteriophage nucleic acid sequence which inhibits bacterial function in a host bacterium. Thus, it is a bacteria-inhibiting phage product.

In the context of this invention, the phrase "contacting the bacterial cell with a compound active on a bacterial target of a bacteriophage inhibitor protein" or equivalent phrases refer to contacting with an isolated, purified, or enriched compound or a composition including such a compound, but specifically does not rely on contacting the bacterial cell with an intact naturally occurring phage which encodes the compound. Preferably no intact phage are involved in the contacting.

Related aspects provide methods for prophylactic or therapeutic treatment of a bacterial infection by administering to an infected, challenged or at risk organism a therapeutically or prophylactically effective amount of a compound active on a target of a bacteriophage 77 ORF 17, 19, 43, 102, 104, or 182 product, e.g., as described for the previous aspect. Preferably the bacterium involved in the infection or risk of infection produces the identified target of the bacteriophage inhibitor protein or alternatively produces a homologous target compound. In preferred embodiments, the host organism is a plant or animal, preferably a mammal or bird, and more preferably, a human or other mammal described herein. Preferred embodiments include, without limitation, those as described for the preceding aspect.

Compounds usefll for the methods of inhibiting, methods of treating, and pharmaceutical compositions can include novel compounds, but can also include compounds which had previously been identified for a purpose other than inhibition of bacteria. Such compounds can be utilized as described and can be included in pharmaceutical compositions.

By "treatment" or "treating" is meant administering a compound or pharmaceutical composition for prophylactic and/or therapeutic purposes. The term "prophylactic treatment" refers to treating a patient or animal that is not yet infected but is susceptible to or otherwise at risk of a bacterial infection. The term "therapeutic treatment" refers to administering treatment to a patient already suffering from infection.

The term "bacterial infection" refers to the invasion of the host organism, animal or plant, by pathogenic bacteria. This includes the excessive growth of bacteria which are normally present in or on the body of the organism, but more generally, a bacterial infection can be any situation in which the presence of a bacterial population(s) is damaging to a host organism. Thus, for example, an organism suffers from a bacterial infection when excessive numbers of a bacterial population are present in or on the organism's body, or when the effects of the presence of a bacterial population(s) is damaging to the cells, tissue, or organs of the organism.

The terms "administer", "administering", and "administration" refer to a method of giving a dosage of a compound or composition, e.g., an antibacterial pharmaceutical composition, to an organism. Where the organism is a mammal, the method is, e.g., topical, oral, intravenous, transdermal, intraperitoneal, intramuscular, or intrathecal. The preferred method of administration can vary depending on various factors, e.g., the components of the pharmaceutical composition, the site of the potential or actual bacterial infection, the bacterium involved, and the infection severity.

The term "mammal" has its usual biological meaning, referring to any organism of the Class Mammalia of higher vertebrates that nourish their young with milk secreted by mammary glands, e.g., mouse, rat, and, in particular, human, bovine, sheep, swine, dog, and cat.

In the context of treating a bacteria infection a "therapeutically effective amount" or "pharmaceutically effective amount" indicates an amount of an antibacterial agent, e.g., as disclosed for this invention, which has a therapeutic effect. This generally refers to the inhibition, to some extent, of the normal cellular functioning of bacterial cells that renders or contributes to bacterial infection.

The dose of antibacterial agent that is useful as a treatment is a "therapeutically effective amount." Thus, as used herein, a therapeutically effective amount means an amount of an antibacterial agent that produces the desired therapeutic effect as judged by clinical trial results and/or animal models. This amount can be routinely determined by one skilled in the art and will vary depending on several factors, such as the particular bacterial strain involved and the particular antibacterial agent used.

In connection with claims to methods of inhibiting bacteria and therapeutic or prophylactic treatments, "a compound active on a target of a bacteriophage inhibitor protein" or terms of equivalent meaning differ from administration of or contact with an intact phage naturally encoding the full-length inhibitor compound. While an intact phage may conceivably be incorporated in the present methods, the method at least includes the use of an active compound as specified different from a full length inhibitor protein naturally encoded by a bacteriophage and/or a delivery or contacting method different from administration of or contact with an intact phage naturally encoding the full-length protein. Similarly, pharmaceutical compositions described herein at least include an active compound or composition different from a phage naturally coding the full-length inhibitor protein, or such a full-length protein is provided in the composition in a form different from being encoded by an intact phage. Preferably the methods and compositions do not include an intact phage.

In accordance with the above aspects, the invention also provides antibacterial agents and compounds active on a bacterial target of bacteriophage ORF 17, 19, 43, 102, 104, or 182, where the target was uncharacterized as indicated above. As previously indicated, such active compounds include both novel compounds and compounds which had previously been identified for a purpose other than inhibition of bacteria. Such previously identified biologically active compounds can be used in embodiments of the above methods of inhibiting and treating. In preferred embodiments, the targets, bacteriophage, and active compound are as described herein for methods of inhibiting and methods of treating. Preferably the agent or compound is formulated in a pharmaceutical composition which includes a pharmaceutically acceptable carrier, excipient, or diluent. In addition, the invention provides agents, compounds, and pharmaceutical compositions where an active compound is active on an uncharacterized phage-specific site on the target.

In preferred embodiments, the target is as described for embodiments of aspects above.

Likewise, the invention provides a method of making an antibacterial agent. The method involves identifying a target of a bacteriophage 77 ORF 17, 19, 43, 102, 104, or 182 product, screening a plurality of compounds to identify a compound active on the target, and synthesizing the compound in an amount sufficient to provide a therapeutic effect when administered to an organism infected by a bacterium naturally producing the target.

In preferred embodiments, the identification of the target and identification of active compounds include steps or methods and/or components as described above (or otherwise herein) for such identification. Likewise, the active compound can be as described above, including fragments and derivatives of phage inhibitor proteins, peptidomimetics, and small molecules. As recognized by those skilled in the art, peptides can be synthesized by expression systems and purified, or can be synthesized artificially by methods well known in the art.

In the context of nucleic acid or amino acid sequences of this invention, the term "corresponding" indicates that the sequence is at least 95% identical, preferably at least 97% identical, and more preferably at least 99% identical to a sequence from the specified phage genome or bacterial genome, a ribonucleotide equivalent, a degenerate equivalent (utilizing one or more degenerate codons), or a homologous sequence, where the homolog provides functionally equivalent biological function.

In embodiments where the bacterial target of a bacteriophage inhibitor ORF product, e.g., an inhibitory protein or polypeptide, the target is preferably encoded by a *S. aureus* nucleic acid coding sequence from a host bacterium for bacteriophage 77. Target sequences are described herein by reference to sequence source sites. The sequence encoding the target preferably corresponds to a *S. aureus* nucleic acid sequence available from numerous sources including *S. aureus* sequences deposited in GenBank, *S. aureus* sequences found in European Patent Application NO: 97100110.7 to Human Genome Sciences, Inc. filed Jan. 7, 1997, *S. aureus* sequences available from TIGR at the Web site for which the remainder of the address after www is tigr.org/tdb/mdb/mdb.html, and *S. aureus* sequences available from the Oklahoma University *S. aureus* sequencing project at the Web site for which the remainder of the address following www is genome.ou.edu/staph_new.html.

The amino acid sequence of a polypeptide target is readily provided by translating the corresponding coding region. For the sake of brevity, the sequences are not reproduced herein. Also, in preferred embodiments, a target sequence corresponds to a *S. aureus* coding sequences corresponding to a sequence listed in Table 6 herein. The listing in Table 6 describes *S. aureus* sequences currently deposited in GenBank. Again, for the sake of brevity, the sequences are described by reference to the GenBank entries instead of being written out in full herein. In cases where an entry for a coding region is not complete, the complete sequence can be readily obtained by routine methods, e.g., by isolating a clone in a phage 77 host *S. aureus* genomic library, and sequencing the clone insert to provide the relevant coding region. The boundaries of the coding region can be identified by conventional sequence analysis and/or by expression in a bacterium in which the endogenous copy of the coding region has been inactivated and using subcloning to identify the functional start and strop codons for the coding region.

As used in the claims to describe the various inventive aspects and embodiments, "comprising" means including, but not limited to, whatever follows the word "comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

Additional features and embodiments of the present invention will be apparent from the following Detailed Description and from the claims, all within the scope of the present invention.

BRIEF DESCRIPTION OF THE DRAWINGS

FIG. 3 shows a schematic representation of the functional assays used to characterize the bactericidal and bacteriostatic potential of all predicted ORFs (>33 amino acids) encoded by bacteriophage 77.

DETAILED DESCRIPTION OF THE PREFERRED EMBODIMENTS

Preliminarily the tables will be briefly described.

Table 1 shows the complete nucleotide sequence of the genome of *Staphylococcus aureus* bacteriophage 77.

Table 2 is a table from Alberts et al., MOLECULAR BIOLOGY OF THE CELL $3^{rd}$ ed., showing the redundancy of the universal" genetic code.

Figure 3A:
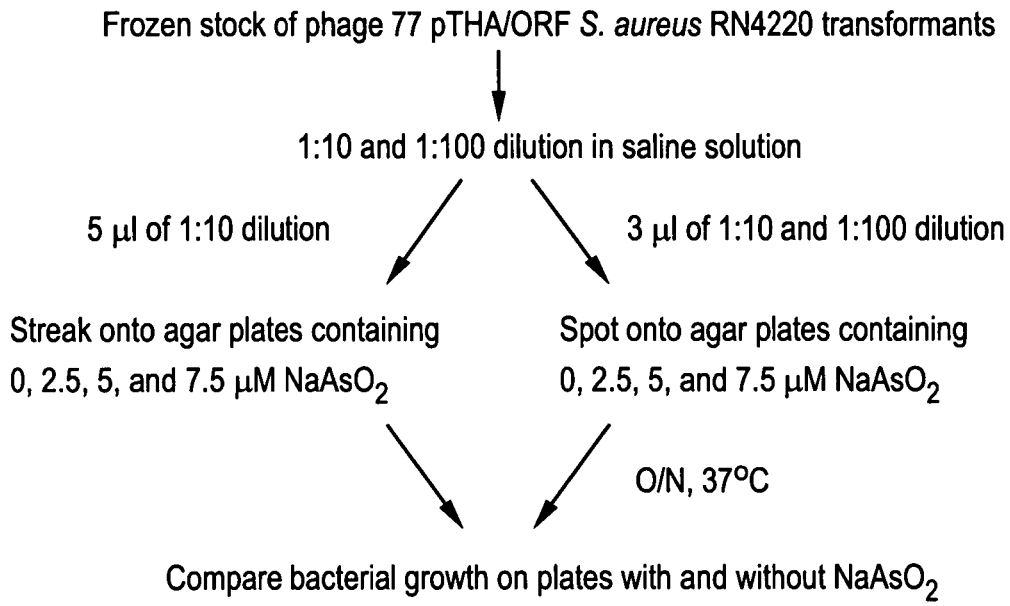
FIG. 3A) Functional assay on semi-solid support media.
Figure 3B:
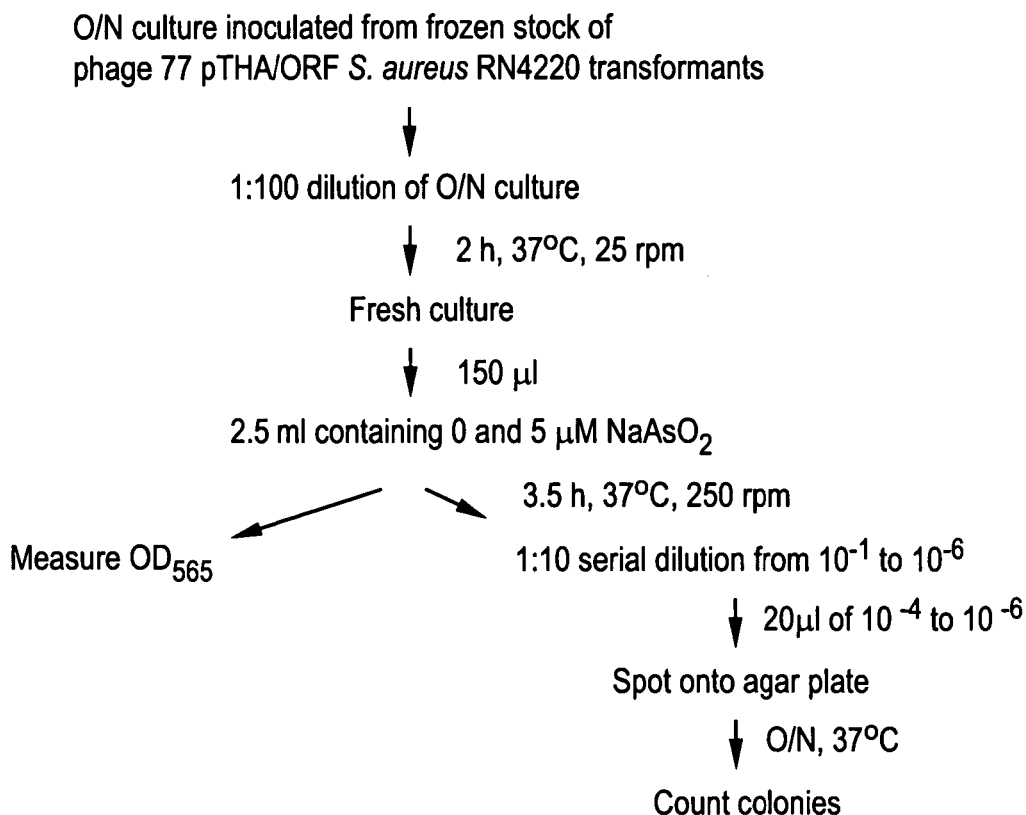
FIG. 3B) Functional assay in liquid culture.
Figure 4A:
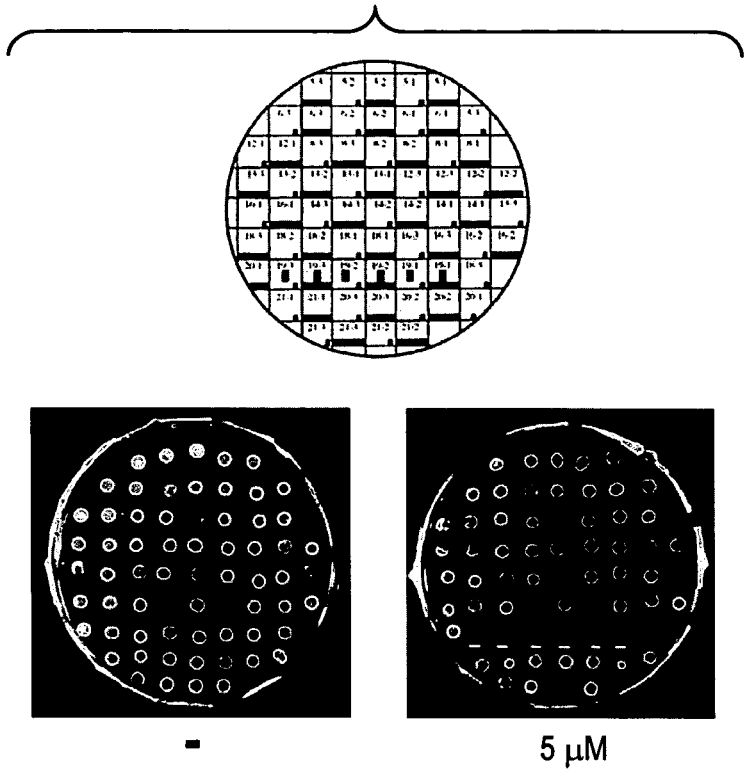
FIG. 4 shows the results of a screen to assess killing potential of bacteriophage 77 encoded ORFs (>33 amino acids) on semi-solid support media. For each ORF tested between one to three independent transformants were tested at two different concentrations. Each panel (A–H) consists of 3 sections: I) A grid showing the position of spotting of individual *Staphylococcus aureus* transformant clones containing a given ORF. The number on the grid refers to the ORF contained within a given Staph A. clone and the number following the dash identifies the different transformants. For example, 5-3 and 5-1 refers to ORF 5, transformant #3 and ORF 5, transformant #1, respectively. A full darkened bar under the name of the Staph clone infers that an undiluted sample of the overnight culture was spotted onto the agar plate; whereas a shortened bar indicates that a 10-fold diluted sample of the overnight culture was spotted onto the agar plate. II) An overnight culture of the *Staphylococcus aureus* transformant was spotted onto directly, or after a 10-fold diluted, onto an agar plate lacking arsenite. III) II) An overnight culture of the *Staphylococcus aureus* transformant was spotted onto directly, or after a 10-fold diluted, onto an agar plate containing 5 $\mu$M arsenite, to induce expression of the ars promoter and hence of the bacteriophage 77 ORF. From this experiment, it is clear that expression of bacteriophage ORF 19 (PanelA) and ORF 182 (Panel C) lead to inhibition of growth of *Staphylococcus aureus*. Positive controls for this experiment included expression of the lysis cassette from bacteriophage 77 (Panel H, Lys-1, Lys-2, Lys-3) and the lysis cassette from bacteriophage 77 (TH-1, TH-2, TH-3).
Figure 4B:
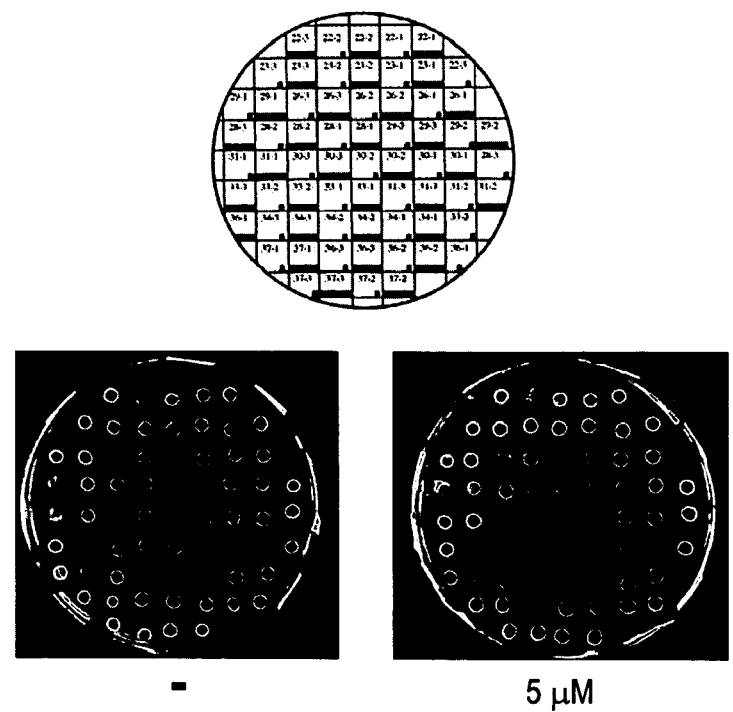
Figures 4C, 4D:
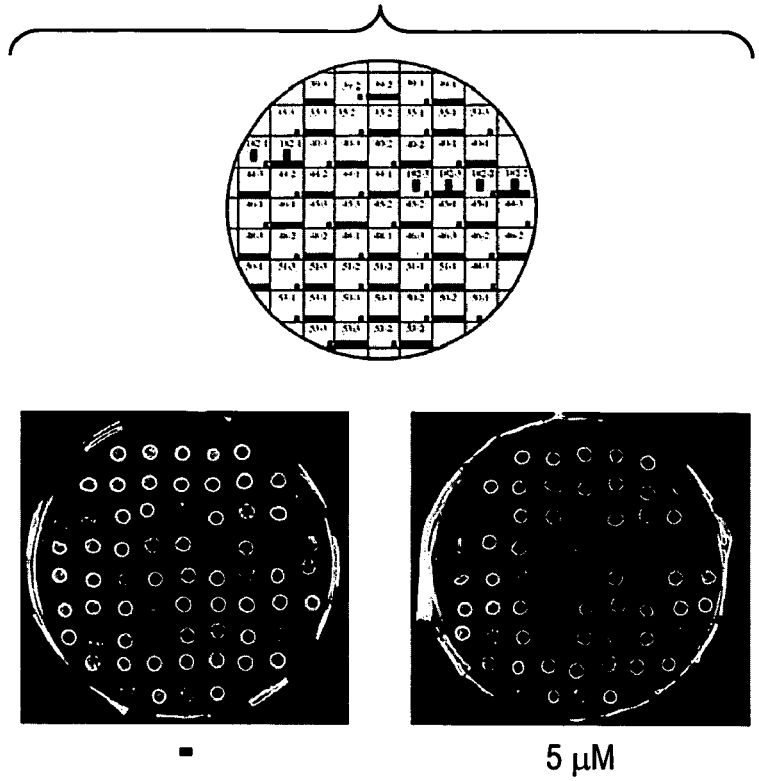
Figure 4E:
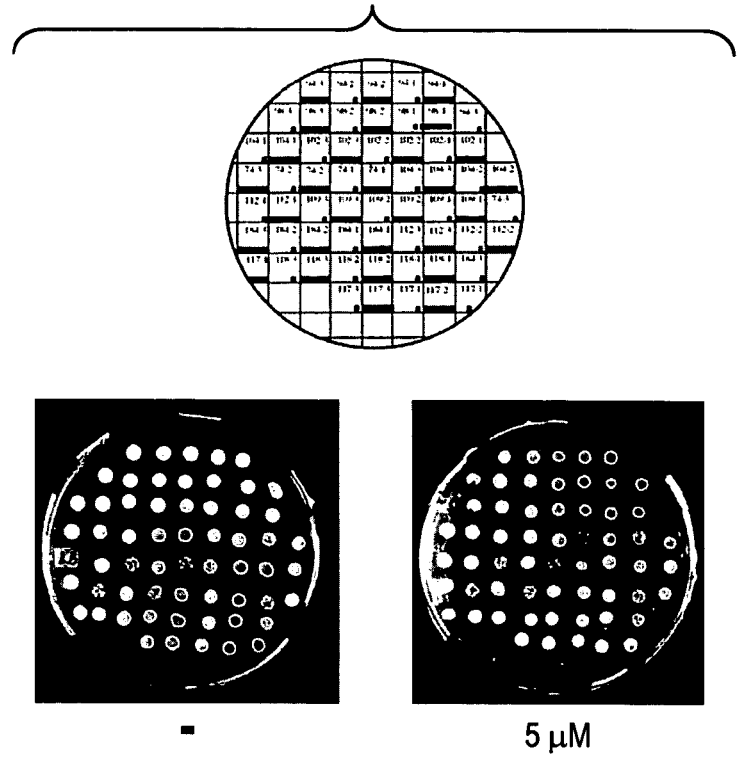
Figure 4F:
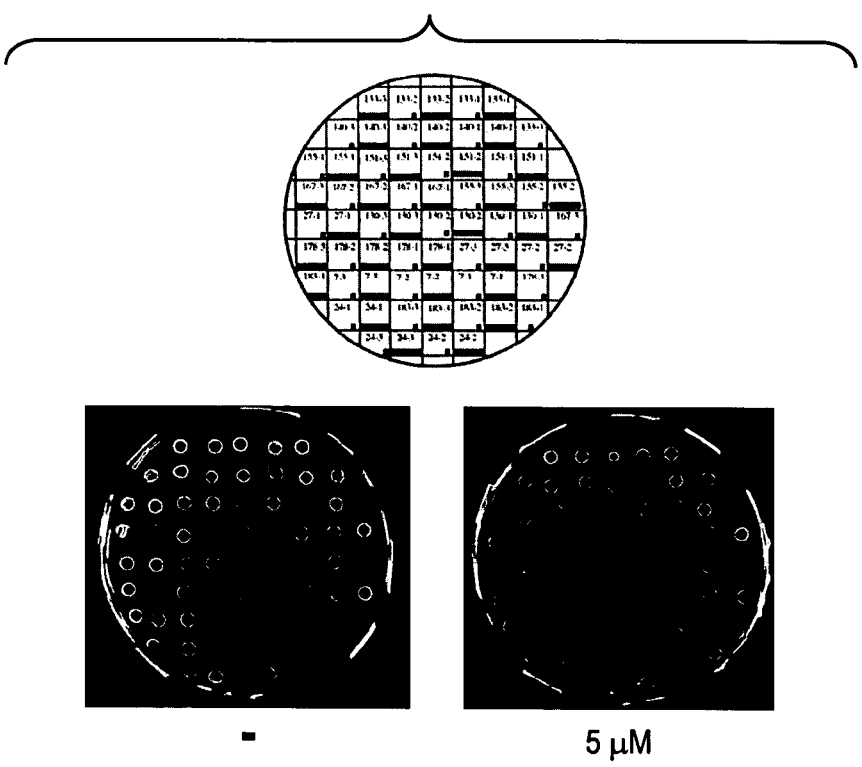
Figure 4G:
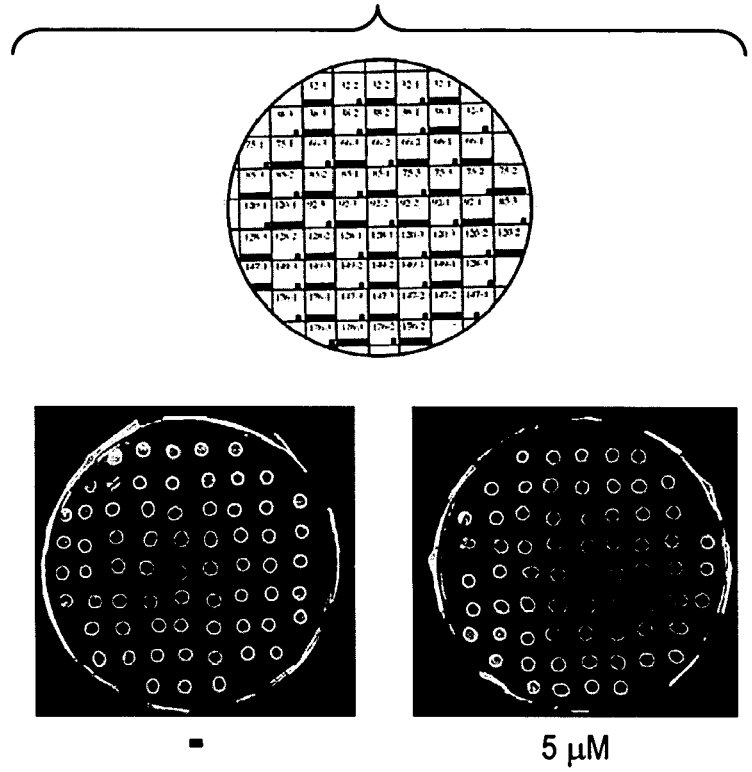
Figure 4H:
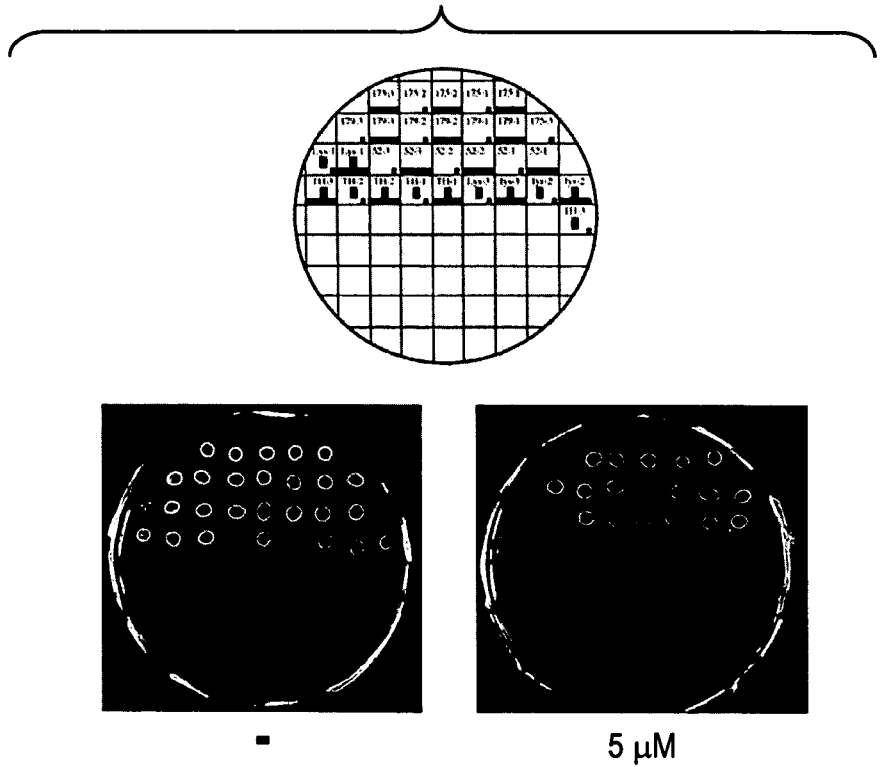
Figure 5A:
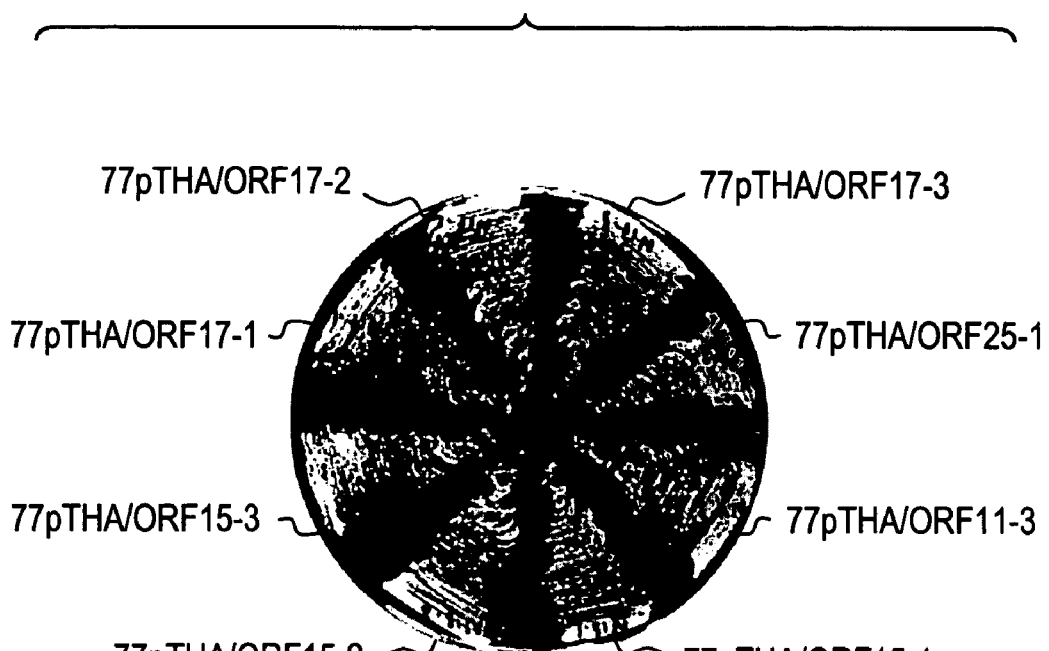
FIG. 5 shows the results of a screen to assess killing potential of bacteriophage 77 encoded ORFs (>33 amino acids) on semi-solid support media. In this experiment, clones of *Staphylococcus aureus* harboring a given bacteriophage 77 ORF were streaked on plates lacking or containing 5 $\mu$M arsenite. Following incubation of the plates at 37° C. overnight, inhibition of growth was visually assessed. The identity of the expression vector and subcloned ORF harbored by the *Staphylococcus* transformant is given around the border of each plate. From this experiment, it is clear that expression of bacteriophage ORF 17 (Panel A), ORF 43 (Panel B), ORF 102, (Panel B and C), and ORF 104 (Panel D) lead to inhibition of growth of *Staphylococcus aureus*.
Figure 5A:
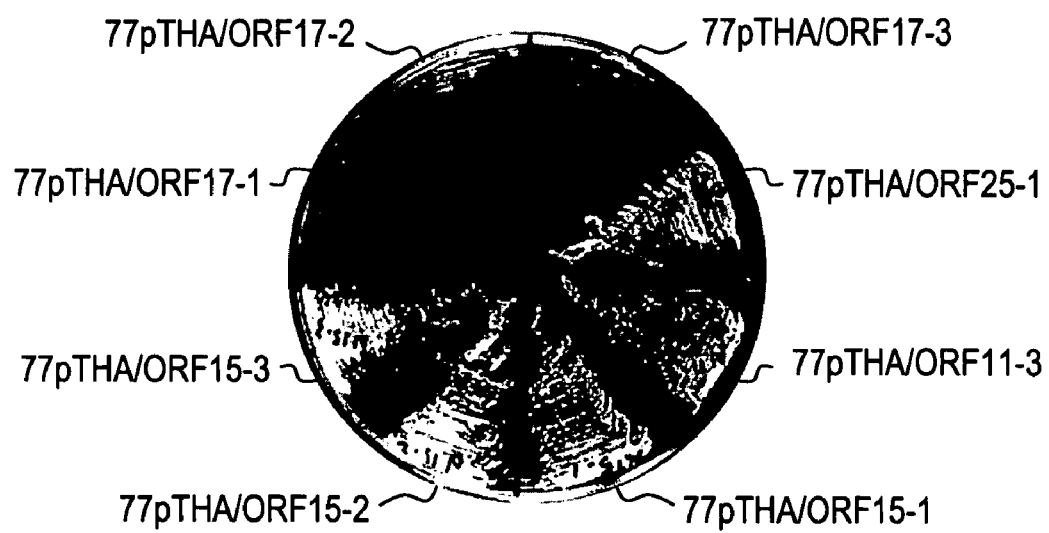
Figure 5B:
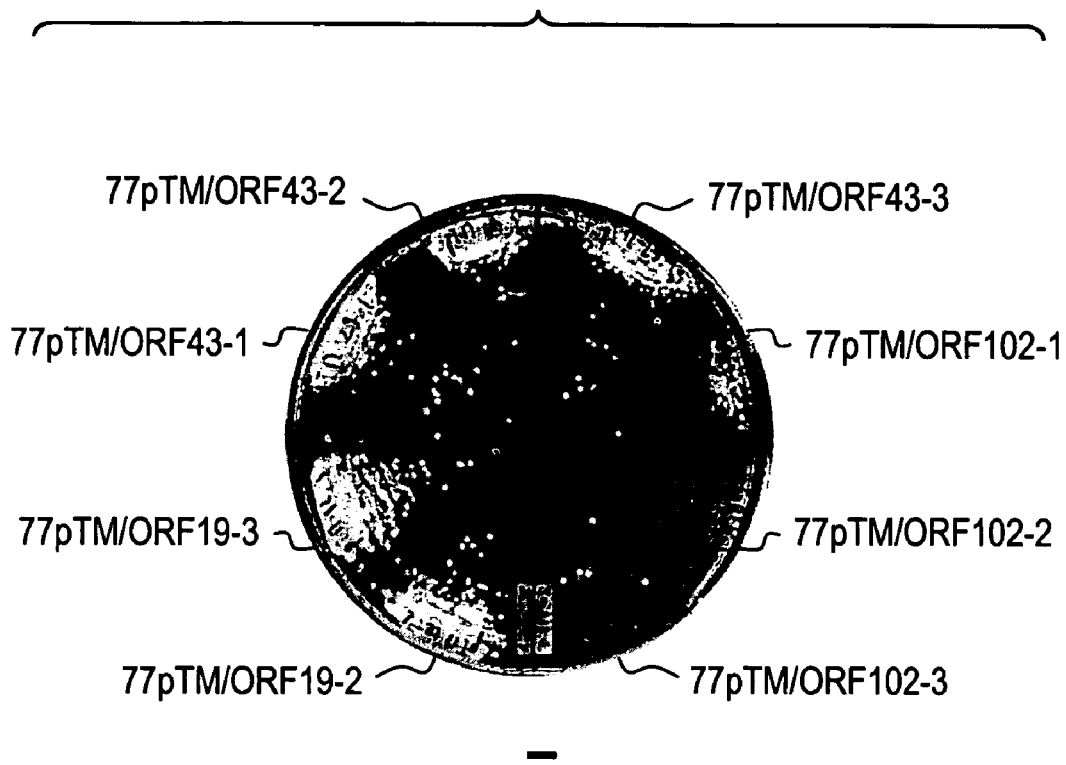
Figure 5B:
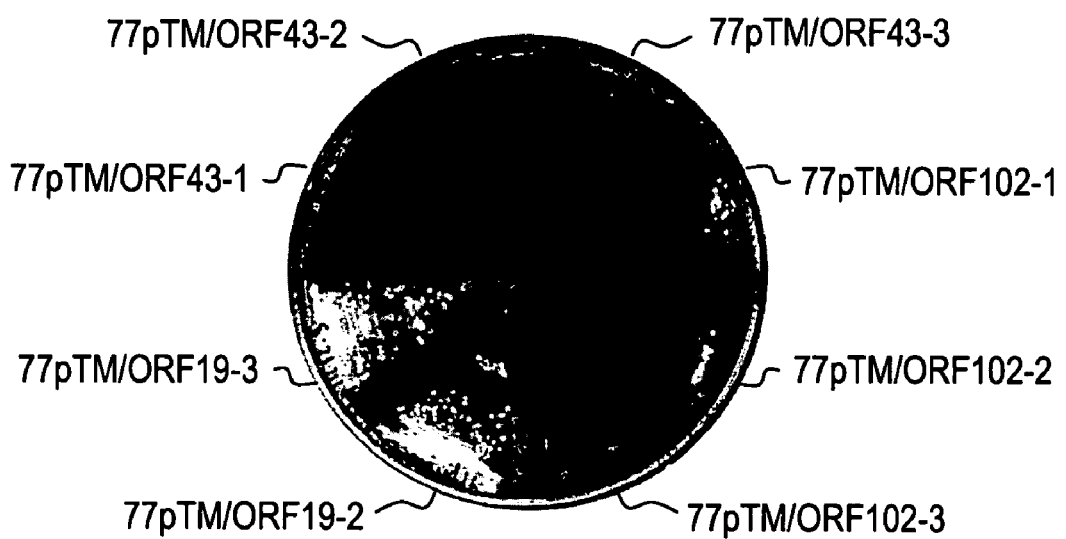
Figure 5C:
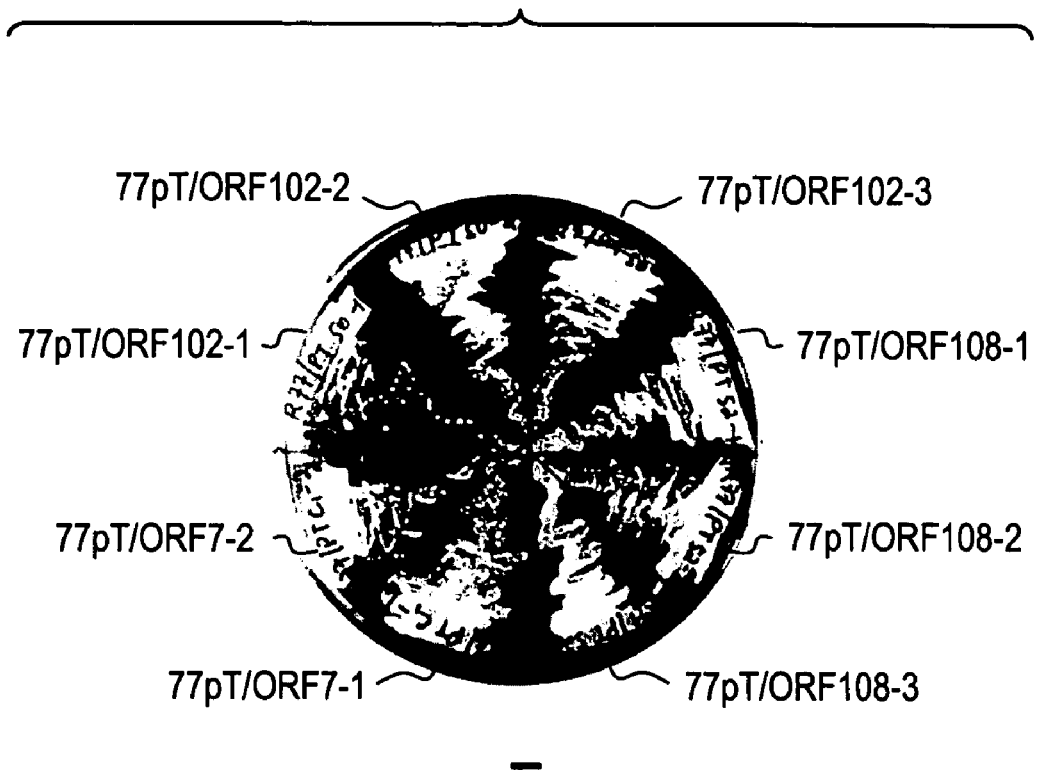
Figure 5C:
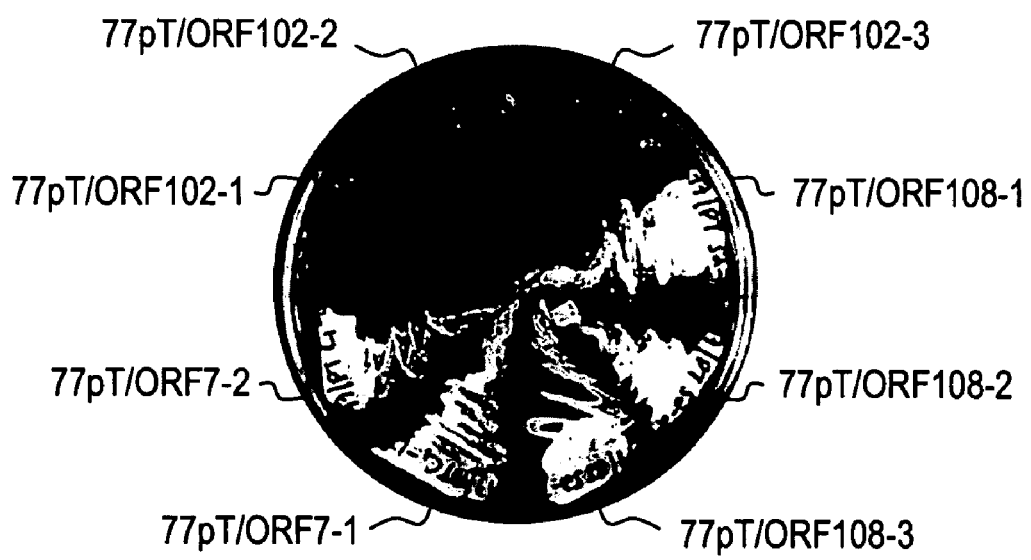
Figure 5D:
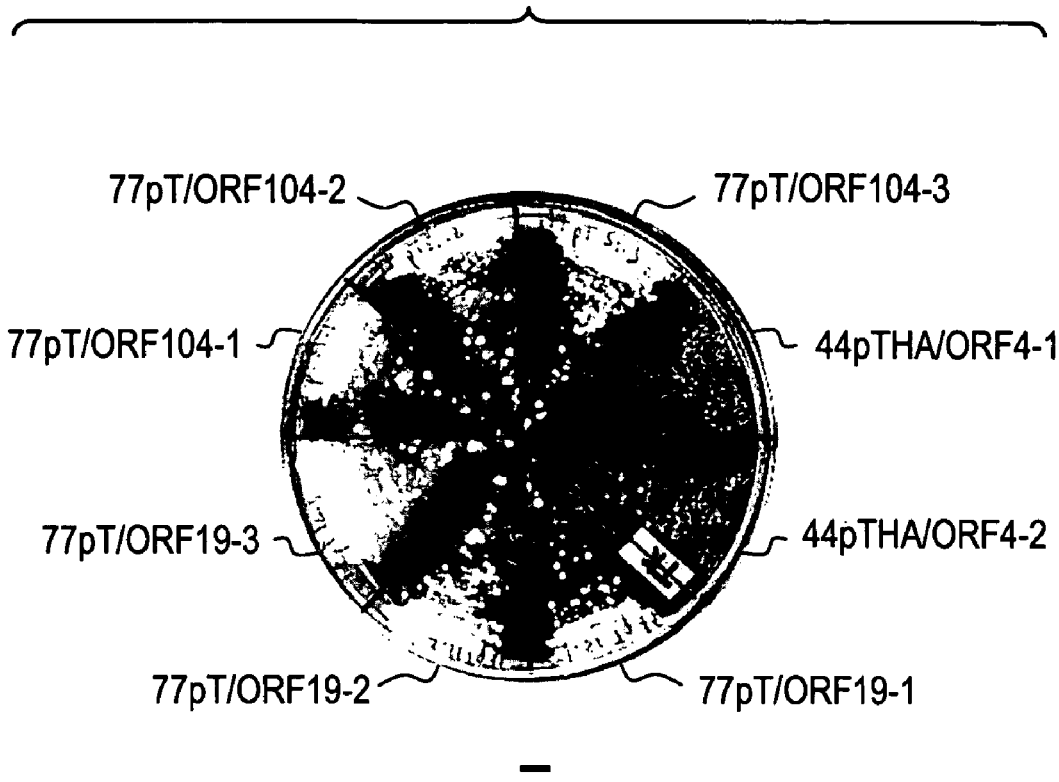
Figure 5D:
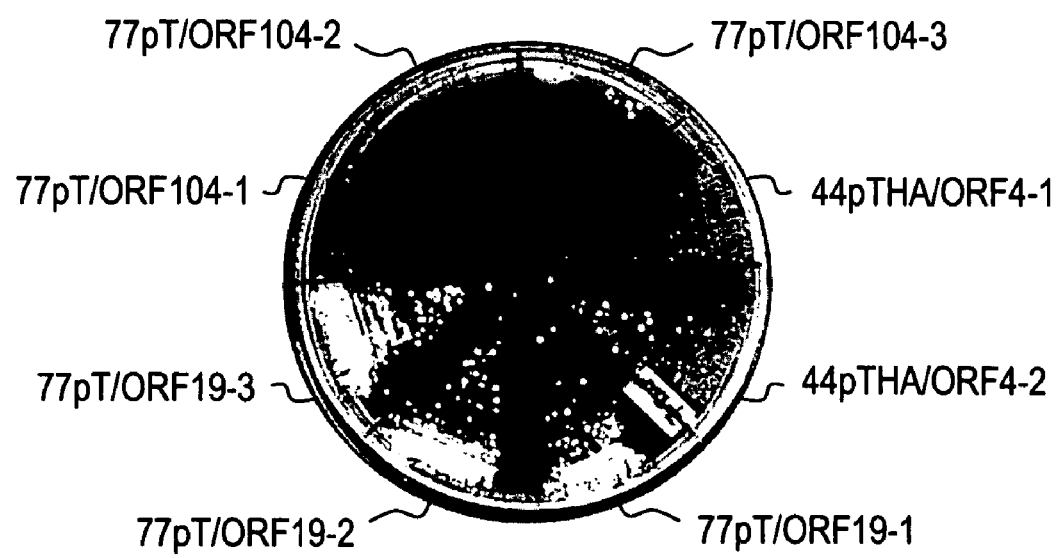
Figure 6A:
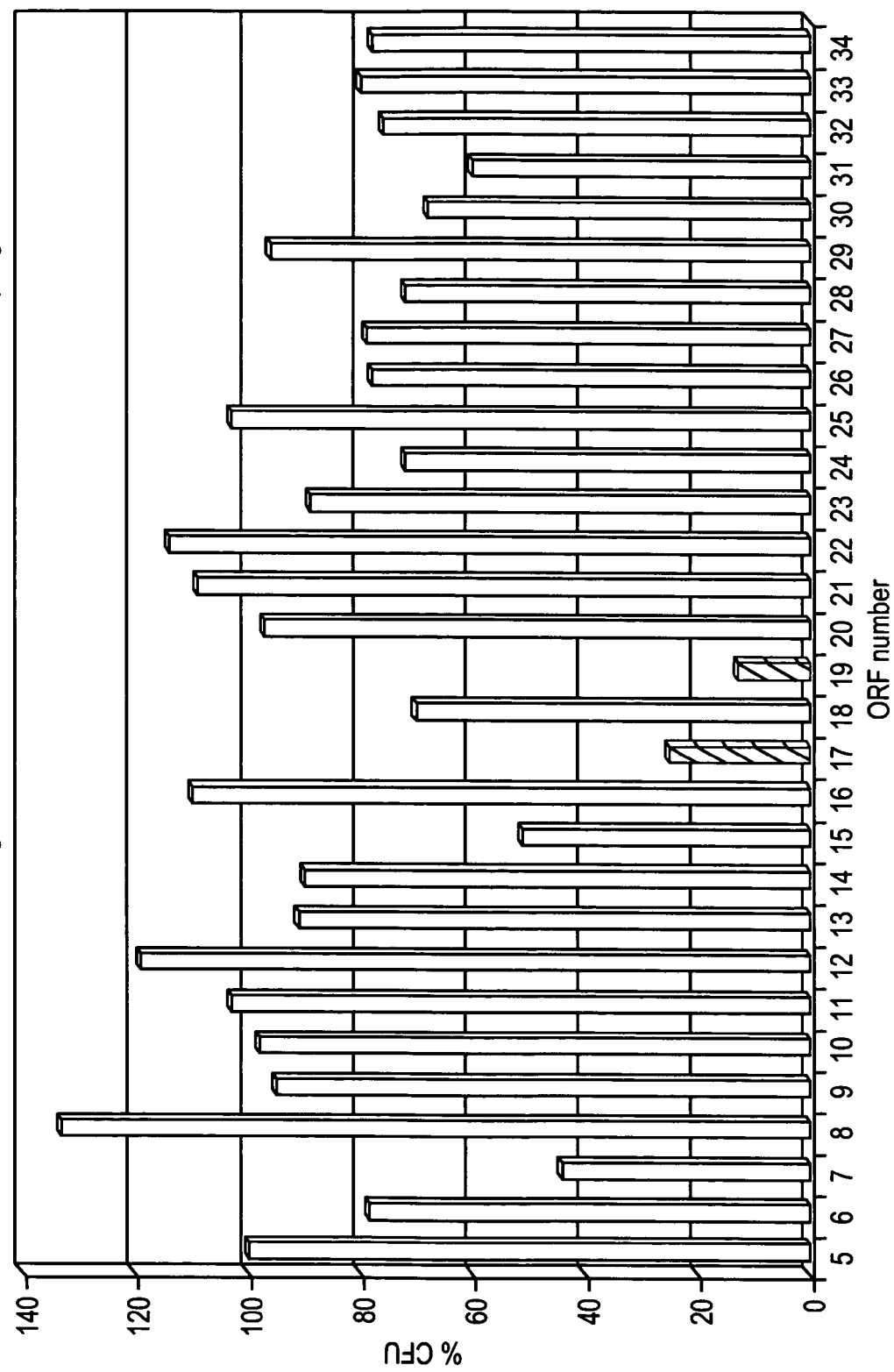
FIG. 6 is a bar graph showing the results of a screen in liquid media to assess bacteriostatic or bactericidal activity of 93 predicted ORFs (>33 amino acids) encoded by bacteriophage 77. Growth inhibition assays were performed as detailed in the Detailed Description. The relative growth of *Staphylococcus aureus* transformants harboring a given bacteriophage 77 ORF (identified on the bottom of the graph), in the absence or presence of arsenite, is plotted relative to growth of a *Staphylococcus aureus* transformant containing ORF 5, a non-toxic bacteriophage 77 ORF (which is set at 100%). Each bar represents the average obtained from three Staph A transformants grown in duplicate. Bacteriophage 77 ORFs showing significant growth inhibition are plotted in red and consist or ORF 17, 19, 102, 104, and 182.
Figure 6C:
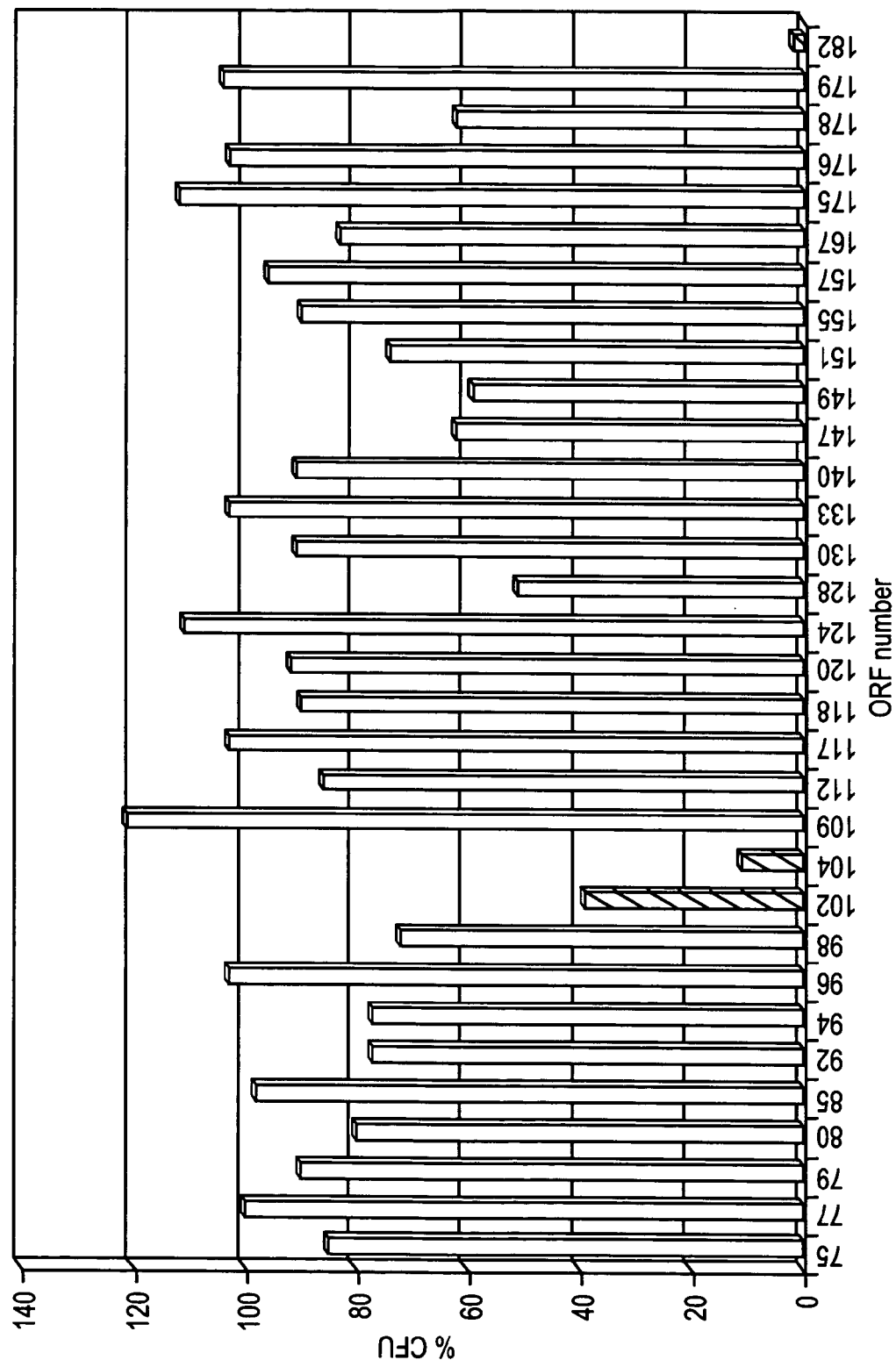

Table 3 FIG. 3 shows the predicted nucleotide sequence, predicted amino acid sequence, and physiochemical parameters of ORF 17/ 19/ 43/ 102/ 104/ 182. These include the primary amino acid sequence of the predicted protein, the average molecular weight, amino acid composition, theoretical pI, hydrophobicity map, and predicted secondary structure map.

Table 4 FIG. 4 Shows homology search results. BLAST analysis was performed with ORFs 17/ 19/ 43/ 102/ 104/ 182 against NCBI non-redundant nucleotide and Swissprot databases. The results of this search indicate that: I) ORF 17 has no significant homology to any gene in the NCBI non-NCBI non-redundant nucleotide database, II) ORF 19 has significant homology to one gene in the NCBI non-redundant nucleotide database—the gene encoding ORF 59 of bacteriophage phi PVL, III) ORF 43 has significant homology to one gene in the NCBI non-redundant nucleotide database—the gene encoding ORF 39 of phi PVL, IV) ORF 102 has significant homology to one gene in the NCBI non-redundant nucleotide database—the gene encoding ORF 38 of phi PVL, V) ORF 104 has no significant homology to any gene in the NCBI non-redundant nucleotide database, VI) ORF 182 has significant homology to one gene in the NCBI non-redundant nucleotide database—the gene encoding ORF 39 of phi PVL.

Table 5 FIG. 7 shows a list of all the ORFs from Bacteriophage 77 that were screened in the functional assay to identify those with anti-microbial activity.

Table 6 is a list of *Staphylococcus aureus* sequences which may represent genes coding for target sequences for the phage 77-encoded antimicrobial proteins or peptides.

The present invention is based on the identification of naturally-occurring DNA sequence elements encoding RNA or proteins with anti-microbial activity. Bacteriophages or phages, are viruses that infect and kill bacteria. They are natural enemies of bacteria and, over the course of evolution have perfected enzymes (products of DNA sequences) which enable them to infect a host bacterium, replicate their genetic material, usurp host metabolism, and ultimately kill their host. The scientific literature documents well the fact that many known bacteria have a large number of such bacteriophages than can infect and kill them (for example, see the ATCC bacteriophage collection at the Web site atcc.org) (Ackermann and DuBow, 1987). Although we know that many bacteriophages encode proteins which can significantly alter their host's metabolism, determination of the killing potential of a given bacteriophage gene product can only be assessed by expressing the gene product in the target bacterial strain.

As indicated in the Summary above, the present invention is concerned with the use of bacteriophage 77 coding sequences and the encoded polypeptides or RNA transcripts to identify bacterial targets for potential new antibacterial agents. Thus, the invention concerns the selection of relevant bacteria. Particularly relevant bacteria are those which are pathogens of a complex organism such as an animal, e.g., mammals, reptiles, and birds, and plants. However, the invention can be applied to any bacterium (whether pathogenic or not) for which bacteriophage are available or which are found to have cellular components closely homologous to components targeted by phage 77 ORFs 17, 19, 43, 102, 104, and 182.

Identification of ORFs 17, 19, 43, 102, 104, and 182 and products from the phage which inhibit the host bacterium both provides an inhibitor compound and allows identification of the bacterial target affected by the phage-encoded inhibitor. Such a target is thus identified as a potential target for development of other antibacterial agents or inhibitors and the use of those targets to inhibit those bacteria. As indicated above, even if such a target is not initially identified in a particular bacterium, such a target can still be identified if a homologous target is identified in another bacterium. Usually, but not necessarily, such another bacterium would be a genetically closely related bacterium. Indeed, in some cases, an inhibitor encoded by phage 77 ORF 17, 19, 43, 102, 104, or 182 can also inhibit such a homologous bacterial cellular component.

The demonstration that bacteriophage have adapted to inhibiting a host bacterium by acting on a particular cellular component or target provides a strong indication that that component is an appropriate target for developing and using antibacterial agents, e.g, in therapeutic treatments. Thus, the present invention provides additional guidance over mere identification of bacterial essential genes, as the present invention also provides an indication of accessibility of the target to an inhibitor, and an indication that the target is sufficiently stable over time (e.g., not subject to high rates of mutation) as phage acting on that target were able to develop and persist. Thus, the present invention identifies a particular subset of essential cellular components which are particularly likely to be appropriate targets for development of antibacterial agents.

The invention also, therefore, concerns the development or identification of inhibitors of bacteria, in addition to the phage-encoded inhibitory proteins (or RNA transcripts), which are active on the targets of bacteriophage-encoded inhibitors. As described herein, such inhibitors can be of a variety of different types, but are preferably small molecules.

The following description provides preferred methods for implementing the various aspects of the invention. However, as those skilled in the art will readily recognize, other approaches can be used to obtain and process relevant information. Thus, the invention is not limited to the specifically described methods. In addition, the following description provides a set of steps in a particular order. That series of steps describes the overall development involved in the present invention. However, it is clear that individual steps or portions of steps may be usefully practiced separately, and, further, that certain steps may be performed in a different order or even bypassed if appropriate information is already available or is provided by other sources or methods.

Identification of Inhibitory ORF

The methodology previously described in U.S. Provisional Patent Application No. 60/110,992, and filed Dec. 3, 1998, was used to to identify and characterize DNA sequences from *Staphylococcus aureus* bacteriophage 77 that can act as anti-microbials. A nucleic acid segment isolated from *Staphylococcus aureus* bacteriophage 77 encodes a protein, whose gene is referred to as ORF (open reading frame) 17, 19, 43, 102, 104, or 182. Thus, the present invention provides a nucleic acid sequence isolated from *Staphylococcus aureus* (Staph A or *S. aureus*) bacteriophage 77 comprising at least a portion of the gene encoding ORF 17, 19, 43, 102, 104, or 182 with anti-microbial activity. The nucleic acid sequence can be isolated using a method similar to those described herein, or using another method. In addition, such a nucleic acid sequence can be chemically synthesized. Having the anti-microbial nucleic acid sequence of the present invention, parts thereof or oligonucleotides derived therefrom, other anti-microbial sequences from other bacteriophage sources using methods described herein or other methods can be isolated, including screening methods based on nucleic acid sequence hybridization.

The present invention provides the use of the Staph A bacteriophage 77 anti-microbial DNA segment encoding ORF 17, 19, 43, 102, 104, or 182, as a pharmacological agent—either wholly or in part—as well as the use of peptidomimetics, developed from amino acid or nucleotide sequence knowledge of Staph A bacteriophage 77 ORF 17, 19, 43, 102, 104, or 182. This can be achieved where the structure of the peptidomimetic compound corresponds to the structure of the active portion of ORF 17, 19, 43, 102, 104, or 182. In this analysis, the peptide backbone is transformed into a carbon-based hydrophobic structure that can retain cytostatic or cytocidal activity for the bacterium. This is done by standard medicinal chemistry methods, measuring growth inhibition of the various molecules in liquid cultures or on solid medium. These mimetics also represent lead compounds for the development of novel antibiotics.

In this context, "corresponds" means that the peptidomimetic compound structure has sufficient similarities to the structure of the active portion of ORF 17, 19, 43, 102, 104, or 182 that the peptidomimetic will interact with the same molecule as the product of ORF 17, 19, 43, 102, 104, or 182 and preferably will elicit at least one cellular response in common which relates to the inhibition of the cell by the phage protein.

The invention also provides bacteriophage anti-microbial DNA segments from other phages based on nucleic acids and sequences hybridizing to the presently identified inhibitory ORF under high stringency conditions or sequences which are homologous as described above. The bacteriophage anti-microbial DNA segment from bacteriophage 77 ORF 17, 19, 43, 102, 104, or 182 can be used to identify a related segment from another related or unrelated phage based on conditions of hybridization or sequence comparison.

Identification of Bacterial Targets

The present invention provides the use of *Staphylococcus* bacteriophage 77 ORFs 17, 19, 43, 102, 104, and 182 anti-microbial activity to identify essential host bacterium interacting proteins or other targets that could, in turn, be used for drug design and/or screening of test compounds. Thus, the invention provides a method of screening for antibacterial agents by determining whether test compounds interact with (e.g., bind to) the bacterial target. The invention also provides a method of making an antibacterial agent based on production and purification of the protein or RNA product of bacteriophage 77 ORF 17, 19, 43, 102, 104, or 182. The method involves identifying a bacterial target of the product of ORF 17, 19, 43, 102, 104, or 182, screening a plurality of compounds to identify a compound active on the target, and synthesizing the compound in an amount sufficient to provide a therapeutic effect when administered to an organism infected by a bacterium naturally producing the target. The rationale is that the product of ORFs 17, 19, 43, 102, 104, and 182 can physically interact and/or modify certain microbial host components to block their function.

A variety of methods are known to those skilled in the art for identifying interacting molecules and for identifying target cellular components. Several approaches and techniques are described below which can be used to identify the host bacterial pathway and protein that interact or are inhibited by ORF 17, 19, 43, 102, 104, or 182.

The first approach is a genetic screen for protein:protein interaction, e.g., either some form of two hybrid screen or some form of suppressor screen. In one form of the two hybrid screen involving the yeast two hybrid system, the nucleic acid segment encoding ORF 17, 19, 43, 102, 104, or 182, or a portion thereof, is fused to the carboxyl terminus of the yeast Gal4 activation domain II (amino acids 768–881) to create a bait vector. A cDNA library of cloned *S. aureus* sequences which have been engineered into a plasmid where the *S. aureus* sequences are fused to the DNA binding domain of Gal4 is also generated. These plasmids are introduced alone, or in combination, into a yeast strain, e.g., Y190, previously engineered with chromosomally integrated copies of the *E. coli* lacZ and the selectable His3 genes, both under Gal4 regulation (Durfee et al., 1993). If the two proteins expressed in yeast interact, the resulting complex will activate transcription from promoters containing Gal4 binding sites. A lacZ and His3 gene, each driven by a promoter containing Gal4 binding sites, have been integrated into the genome of the host yeast system and are used for measuring protein—protein interactions. Such a system provides a physiological environment in which to detect potential protein interactions.

This system has been extensively used to identify novel protein—protein interaction partners and to map the sites required for interaction (for example, to identify interacting partners of translation factors (Qui et al., 1998), transcription factors (Katagiri et al., 1998), proteins involved in signal transduction (Endo et al., 1997). Alternatively, a bacterial two-hybrid screen can be utilized to circumvent the need for the interacting proteins to be targeted to the nucleus, as is the case in the yeast system (Karimova et al., 1998).

The protein targets of ORFs 17, 19, 43, 102, 104, and 182 can also be identified using bacterial genetic screens. One approach involves the overexpression of ORF 17, 19, 43, 102, 104, or 182 protein in mutagenized *S. aureus* followed by plating the cells and searching for colonies that can survive the anti-microbial activity of ORF 17, 19, 43, 102, 104, or 182. These colonies are then grown, their DNA extracted, and cloned into an expression vector that contains a replicon of a different incompatibility group from the plasmid expressing ORF 17, 19, 43, 102, 104, or 182. This library is then introduced into a wild-type Staph A bacterium in conjunction with an expression vector driving synthesis of ORF 17, 19, 43, 102, 104, or 182, followed by selection for surviving bacteria. Thus, Staph A DNA fragments from the survivors presumably contain a DNA fragment from the original mutagenized Staph A genome that can protect the cell from the antimicrobial activity of ORF 17, 19, 43, 102, 104, or 182. This fragment can be sequenced and compared with that of the bacterial host to determine in which gene the mutation lies. This approach enables one to determine the targets and pathways that are affected by the killing function.

Alternatively, the bacterial targets can be determined in the absence of selecting for mutations using the approach known as "multicopy suppression". In this approach, the DNA from the wild type Staph A host is cloned into an expression vector that can coexist with the one containing ORF 17, 19, 43, 102, 104, or 182. Those plasmids that contain host DNA fragments and genes which protect the host from the anti microbial activity of ORF 17, 19, 43, 102, 104, or 182 can then be isolated and sequenced to identify putative targets and pathways in the host bacteria.

Another approach is based on identifying protein:protein interactions between the product of ORF 17, 19, 43, 102, 104, or 182 and *S. aureus* host proteins, using a biochemical approach based on affinity chromatography. This approach has been used to identify interactions between lambda phage proteins and proteins from their *E. coli* host (Sopta et al., 1995). The product of ORF 17, 19, 43, 102, 104, or 182 is fused to a tag (e.g.-glutathione-S-transferase) after insertion in a commercially available plasmid vector which directs high-level expression after induction of the responsive promoter driving the fusion protein. The fusion protein is expressed in *E. coli*, purified, and immobilized on a solid phase matrix. Total cell extracts from *S. aureus* are then passed through the affinity matrix containing the immobilized phage ORF fusion protein; host proteins retained on the column are then eluted under different conditions of ionic strength, pH, and detergents and identified by gel electrophoresis. They are recovered from the gel by transfer to a high affinity membrane. The proteins are individually digested to completion with a protease (e.g.-trypsin) and either molecular mass or the amino acid sequence of the tryptic fragments can be determined by mass spectrometry using MALDI-TOF technology (Qin et al., 1997). The sequence of the individual peptides from a single protein are then analyzed by a bioinformatics approach to identify the *S. aureus* protein interacting with the phage ORF. This is performed by a computer search of the *S. aureus* genome for the identified sequence. Alternatively, tryptic peptide fragments of the *S. aureus* genome can be predicted by computer software based on the nucleotide sequence of the genome, and the predicted molecular mass of peptide fragments generated in silico compared to the molecular mass of the peptides obtained from each interacting protein eluted from the affinity matrix.

In addition, an oligonucleotide cocktail can be synthesized based on the primary amino acid sequence determined for an interacting *S. aureus* protein fragment. This oligonucleotide cocktail would comprise a mixture of oligonucleotides based on the nucleotide sequences of the primary amino acid of the predicted peptide, but in which all possible codons for a particular amino acid sequence are present in a subset of the oligonucleotide pool. This cocktail can then be used as a degenerate probe set to screen, by hybridization to genomic or cDNA libraries, to isolate the corresponding gene.

Alternatively, antibodies raised to peptides which correspond to an interacting *S. aureus* protein fragment can be used to screen expression libraries (genomic or cDNA) to identify the gene encoding the interacting protein.

Vectors

The invention also provides vectors, preferably expression vectors, harboring the anti-microbial DNA nucleic acid segment of the invention in an expressible form, and cells transformed with the same. Such cells can serve a variety of purposes, such as in vitro models for the function of the anti-microbial nucleic acid segment and screening for downstream targets of the anti-microbial nucleic acid segment, as well as expression to provide relatively large quantities of the inhibitory product. Thus, an expression vector harboring the anti-microbial nucleic acid segment or parts thereof (Staph A bacteriophage 77 ORF 17, 19, 43, 102, 104, or 182) can also be used to obtain substantially pure protein. Well-known vectors, such as the pGEX series (available from Pharmacia), can be used to obtain large amounts of the protein which can then be purified by standard biochemical methods based on charge, molecular mass, solubility, or affinity selection of the protein by using gene fusion techniques (such as GST fusion, which permits the purification of the protein of interest on a glutathione column). Other types of purification methods or fusion proteins could also be used as recognized by those skilled in the art.

Likewise, vectors containing bacteriophage 77 ORFs 17, 19, 43, 102, 104, and 182 can be used in methods for identifying targets of the encoded antibacterial ORF product, e.g., as described above, and/or for testing inhibition of homologous bacterial targets or other potential targets in bacterial species other than *Staphylococcus aureus*.

Antibodies

Antibodies, both polyclonal and monoclonal, can be prepared against the protein encoded by a bacteriophage anti-microbial DNA segment of the invention (e.g., Staph A bacteriophage 77 ORF 17, 19, 43, 102, 104, or 182) by methods well known in the art. Protein for preparation of such antibodies can be prepared by purification, usually from a recombinant cell expressing the specified ORF or fragment thereof. Those skilled in the art are familiar with methods for preparing polyclonal or monoclonal antibodies (See, e.g., *Antibodies: A Laboratory Manual*, Harlow and Lane, Cold Spring Harbor Laboratory, CSHL. Press, N.Y., 1988).

Such antibodies can be used for a variety of purposes including affinity purification of the protein encoded by the bacteriophage anti-microbial DNA segment, tethering of the protein encoded by the bacteriophage anti-microbial DNA segment to a solid matrix for purposes of identifying interacting host bacterium proteins, and for monitoring of expression of the protein encoded by the bacteriophage anti-microbial DNA segment.

Recombinant Cells

Bacterial cells containing an inducible vector regulating expression of the bacteriophage anti-microbial DNA segment can be used to generate an animal model system for the study of infection by the host bacterium. The functional activity of the proteins encoded by the bacteriophage anti-microbial DNA segments, whether native or mutated, can be tested in animal in vitro or in vivo models.

While such cells containing inducible expression vectors is preferred, other recombinant cells containing a recombinant phage 77 ORF 17, 19, 43, 102, 104, or 182 sequence or portion thereof are also provided by the present invention.

Also, a recombinant cell may contain a recombinant sequence encoding at least a portion of a protein which is a target of phage 77 ORF 17, 19, 43, 102, 104, or 182 inhibitory ORF product.

In the context of this invention, in connection with nucleic acid sequences, the term "recombinant" refers to nucleic acid sequences which have been placed in a genetic location by intervention using molecular biology techniques, and does not include the relocation of phage sequences during or as a result of phage infection of a bacterium or normal genetic exchange processes such as bacterial conjugation.

Derivatization of Identified Anti-Microbials

In cases where the identified anti-microbials above are peptidic compounds, the in vivo effectiveness of such compounds may be advantageously enhanced by chemical modification using the natural polypeptide as a starting point and incorporating changes that provide advantages for use, for example, increased stability to proteolytic degradation, reduced antigenicity, improved tissue penetration, and/or improved delivery characteristics.

In addition to active modifications and derivative creations, it can also be useful to provide inactive modifications or derivatives for use as negative controls or introduction of immunologic tolerance. For example, a biologically inactive derivative which has essentially the same epitopes as the corresponding natural antimicrobial can be used to induce immunological tolerance in a patient being treated. The induction of tolerance can then allow uninterrupted treatment with the active anti-microbial to continue for a significantly longer period of time.

Modified anti-microbial polypeptides and derivatives can be produced using a number of different types of modifications to the amino acid chain. Many such methods are known to those skilled in the art. The changes can include, for example, reduction of the size of the molecule, and/or the modification of the amino acid sequence of the molecule. In addition, a variety of different chemical modifications of the naturally occurring polypeptide can be used, either with or without modifications to the amino acid sequence or size of the molecule. Such chemical modifications can, for example, include the incorporation of modified or non-natural amino acids or non-amino acid moieties during synthesis of the peptide chain, or the post-synthesis modification of incorporated chain moieties.

The oligopeptides of this invention can be synthesized chemically or through an appropriate gene expression system. Synthetic peptides can include both naturally occurring amino acids and laboratory synthesized, modified amino acids.

Also provided herein are functional derivatives of anti-microbial proteins or polypeptides. By "functional derivative" is meant a "chemical derivative," "fragment," "variant," "chimera," or "hybrid" of the polypeptide or protein, which terms are defined below. A functional derivative retains at least a portion of the function of the protein, for example, reactivity with a specific antibody, enzymatic activity or binding activity.

A "chemical derivative" of the complex contains additional chemical moieties not normally a part of the protein or peptide. Such moieties may improve the molecule's solubility, absorption, biological half-life, and the like. The moieties may alternatively decrease the toxicity of the molecule, eliminate or attenuate any undesirable side effect of the molecule, and the like. Moieties capable of mediating such effects are disclosed in Alfonso and Gennaro (1995). Procedures for coupling such moieties to a molecule are well known in the art. Covalent modifications of the protein or peptides are included within the scope of this invention. Such modifications may be introduced into the molecule by reacting targeted amino acid residues of the peptide with an organic derivatizing agent that is capable of reacting with selected side chains or terminal residues, as described below.

Cysteinyl residues most commonly are reacted with alpha-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, chloroacetyl phosphate, N-alkylmaleimides, 3-nitro-2-pyridyl disulfide, methyl 2-pyridyl disulfide, p-chloro-mercuribenzoate, 2-chloromercuri-4-nitrophenol, or chloro-7-nitrobenzo-2-oxa-1,3-diazole.

Histidyl residues are derivatized by reaction with diethylprocarbonate at pH 5.5–7.0 because this agent is relatively specific for the histidyl side chain. Para-bromophenacyl bromide also is useful; the reaction is preferably performed in 0.1 M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing primary amine-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine alpha-amino group.

Tyrosyl residues are well-known targets of modification for introduction of spectral labels by reaction with aromatic diazonium compounds or tetranitromethane. Most commonly, N-acetylimidizol and tetranitromethane are used to form O-acetyl tyrosyl species and 3-nitro derivatives, respectively.

Carboxyl side groups (aspartyl or glutamyl) are selectively modified by reaction carbodiimide (R'—N—C—N—R') such as 1-cyclohexyl-3-(2-morpholinyl(4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Derivatization with bifunctional agents is useful, for example, for cross-linking component peptides to each other or the complex to a water-insoluble support matrix or to other macromolecular carriers. Commonly used cross-linking agents include, for example, 1,1-bis (diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[p-azidophenyl) dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691, 016; 4,195,128; 4,247,642; 4,229,537; and 4,330,440 are employed for protein immobilization.

Other modifications include hydroxylation of proline and lysine, phosphorylation of hydroxyl groups of seryl or threonyl residues, methylation of the alpha-amino groups of lysine, arginine, and histidine side chains (Creighton, T. E., *Proteins: Structure and Molecular Properties*, W. H. Freeman & Co., San Francisco, pp. 79–86 (1983)), acetylation of the N-terminal amine, and, in some instances, amidation of the C-terminal carboxyl groups.

Such derivatized moieties may improve the stability, solubility, absorption, biological half-life, and the like. The moieties may alternatively eliminate or attenuate any undesirable side effect of the protein complex. Moieties capable of mediating such effects are disclosed, for example, in Alfonso and Gennaro (1995).

The term "fragment" is used to indicate a polypeptide derived from the amino acid sequence of the protein or polypeptide having a length less than the full-length polypeptide from which it has been derived. Such a fragment may, for example, be produced by proteolytic cleavage of the full-length protein. Preferably, the fragment is obtained recombinantly by appropriately modifying the DNA sequence encoding the proteins to delete one or more amino acids at one or more sites of the C-terminus, N-terminus, and/or within the native sequence.

Another functional derivative intended to be within the scope of the present invention is a "variant" polypeptide which either lacks one or more amino acids or contains additional or substituted amino acids relative to the native polypeptide. The variant may be derived from a naturally occurring polypeptide by appropriately modifying the protein DNA coding sequence to add, remove, and/or to modify codons for one or more amino acids at one or more sites of the C-terminus, N-terminus, and/or within the native sequence.

A functional derivative of a protein or polypeptide with deleted, inserted and/or substituted amino acid residues may be prepared using standard techniques well-known to those of ordinary skill in the art. For example, the modified components of the functional derivatives may be produced using site-directed mutagenesis techniques (as exemplified by Adelman et al., 1983, *DNA* 2:183; Sambrook et al., 1989) wherein nucleotides in the DNA coding sequence are modified such that a modified coding sequence is produced, and thereafter expressing this recombinant DNA in a prokaryotic or eukaryotic host cell, using techniques such as those described above. Alternatively, components of functional derivatives of complexes with amino acid deletions, insertions and/or substitutions may be conveniently prepared by direct chemical synthesis, using methods well-known in the art.

Insofar as other anti-microbial inhibitor compounds identified by the invention described herein may not be peptidal in nature, other chemical techniques exist to allow their suitable modification, as well, and according the desirable principles discussed above.

Administration and Pharmaceutical Compositions

For the therapeutic and prophylactic treatment of infection, the preferred method of preparation or administration of anti-microbial compounds will generally vary depending on the precise identity and nature of the anti-microbial being delivered. Thus, those skilled in the art will understand that administration methods known in the art will also be appropriate for the compounds of this invention. Pharmaceutical compositions are prepared, as understood by those skilled in the art, to be appropriate for therapeutic use. Thus, generally the components and composition are prepared to be sterile and free of components or contaminants which would pose an unacceptable risk to a patient. For compositions to be administered internally is is generally important that the composition be pyrogen free, for example.

The particularly desired anti-microbial can be administered to a patient either by itself, or in pharmaceutical compositions where it is mixed with suitable carriers or excipient(s). In treating an infection, a therapeutically effective amount of an agent or agents is administered. A therapeutically effective dose refers to that amount of the compound that results in amelioration of one or more symptoms of bacterial infection and/or a prolongation of patient survival or patient comfort.

Toxicity, therapeutic and prophylactic efficacy of anti-microbials can be determined by standard pharmaceutical procedures in cell cultures and/or experimental organisms such as animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized.

For any compound identified and used in the method of the invention, the therapeutically effective dose can be estimated initially from cell culture assays. Such information can be used to more accurately determine useful doses in organisms such as plants and animals, preferably mammals, and most preferably humans. Levels in plasma may be measured, for example, by HPLC or other means appropriate for detection of the particular compound.

The exact formulation, route of administration and dosage can be chosen by the individual physician in view of the patient's condition (see e.g. Fingl et. al., in *The Pharmacological Basis of Therapeutics,* 1975, Ch. 1 p. 1).

It should be noted that the attending physician would know how and when to terminate, interrupt, or adjust administration due to toxicity, organ dysfunction, or other systemic malady. Conversely, the attending physician would also know to adjust treatment to higher levels if the clinical response were not adequate (precluding toxicity). The magnitude of an administered dose in the management of the disorder of interest will vary with the severity of the condition to be treated and the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above also may be used in veterinary or phyto medicine.

Depending on the specific infection target being treated and the method selected, such agents may be formulated and administered systemically or locally, i.e., topically. Techniques for formulation and administration may be found in Alfonso and Gennaro (1995). Suitable routes may include, for example, oral, rectal, transdermal, vaginal, transmucosal, intestinal, parenteral, intramuscular, subcutaneous, or intramedullary injections, as well as intrathecal, intravenous, or intraperitoneal injections.

For injection, the agents of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

Use of pharmaceutically acceptable carriers to formulate identified anti-microbials of the present invention into dosages suitable for systemic administration is within the scope of the invention. With proper choice of carrier and suitable manufacturing practice, the compositions of the present invention, in particular those formulated as solutions, may be administered parenterally, such as by intravenous injection. Appropriate compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, small organic molecules may be directly administered intracellularly.

Pharmaceutical compositions suitable for use in the present invention include compositions wherein the active ingredients are contained in an effective amount to achieve the intended purpose. Determination of the effective amounts is well within the capability of those skilled in the art.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions, including those formulated for delayed release or only to be released when the pharmaceutical reaches the small or large intestine.

The pharmaceutical compositions of the present invention may be manufactured in a manner that is itself known, e.g., by means of conventional mixing, dissolving, granulating, dragee-making, levitating, emulsifying, encapsulating, entrapping or lyophilizing processes.

Pharmaceutical formulations for parenteral administration include aqueous solutions of the active anti-microbial compounds in water-soluble form. Alternatively, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

The above methodologies may be employed either actively or prophylactically against an infection of interest.

To identify DNA segments of Staph A bacteriophage 77 capable of acting as anti-microbial agents, a strategy described in a existing provisional patent was employed (U.S. Provisional Application No. 60/110,992, and filed Dec. 3, 1998). In essence, the procedure involved sequence characterization of the bacteriophage, identification of protein coding regions (open reading frames or ORFs), subcloning of all ORFs into an appropriate inducible expression vector, transfer of the ORF subclones into Staph. A, followed by induction of ORF expression and assessment of effect on growth. We employed discovery steps as described in the Examples.

EXAMPLE I

Growth of Staph A Bacteriophage 77 and Purification of Genomic DNA

The *Staphylococcus aureus* propagating strain (PS 77; ATCC #27699) was used as a host to propagate its respective phage 77 (ATCC # 27699-B1). Two rounds of plaque purification of phage 77 were performed on soft agar essentially as described in Sambrook et al (1989). Briefly, the PS 77 strain was grown overnight at 37° C. in Nutrient broth [NB: 0.3% Bacto beef extract, 0.5% Bacto peptone (Difco Laboratories) and 0.5% NaCl (w/v)]. The culture was then diluted 20× in NB and incubated at 37° C. until the $OD_{540}$=0.2 (early log phase) with constant agitation. In order to obtain single plaques, phage 77 was subjected to 10-fold serial dilutions using phage buffer (1 mM $MgSO_4$, 5 mM $MgCl_2$, 80 mM NaCl and 0.1% Gelatin (w/v)) and 10 µl of each dilution was used to infect 0.5 ml of the cell suspension in the presence of 400 µg/ml $CaCl_2$. After incubation of 15 min at room temperature (RT), 2 ml of melted soft agar kept at 45° C. (NB supplemented with 0.6% agar) was added to the mixture and poured onto the surface of 100 mm nutrient agar plates (0.3% Bacto Beef extract, 0.5% Bacto peptone, 0.5% NaCl and 1.5% Bacto agar (w/v)). After overnight incubation at 30° C., a single plaque was isolated, resuspended in 1 ml of phage buffer by end over end rotation for 2 hrs at 20° C., and the phage suspension was diluted and used for a second infection as described above. After overnight incubation at 30° C., a single plaque was isolated and used as a stock.

The propagation procedure for bacteriophage 77 was modified from the agar layer method of Swanstörm and Adams (1951). Briefly, the PS 77 strain was grown to stationary phase overnight at 37° C. in Nutrient broth. The culture was then diluted twenty-fold in NB and incubated at 37° C. until the $OD_{540}$=0.2. The suspension (15×10$^7$ Bacteria) was then mixed with 15×10$^5$ plaque forming units (pfu) to give a ratio of 100-bacteria/phage particle in the presence of 400 µg/ml of $CaCl_2$. After incubation for 15 min at 20° C., 7.5 ml of melted soft agar (NB plus 0.6% agar) were added to the mixture and poured onto the surface of 150 mm nutrient agar plates and incubated 16 hrs at 30° C. To collect the phage plate lysate, 20 ml of NB were added to each plate and the soft agar layer was collected by scrapping off with a clean microscope slide followed by shaking of the agar suspension for 5 min to break up the agar. The mixture was then centrifuged for 10 min at 4,000 RPM (2,830×g) in a JA-10 rotor (Beckman) and the supernatant fluid (lysate) was collected and subjected to a treatment with 10 µg/ml of DNase I and RNase A for 30 min at 37° C. To precipitate the phage particles, the phage suspension was adjusted to 10% (w/v) PEG 8000 and 0.5 M of NaCl followed by incubation at 4° C. for 16 hrs. The phage was recovered by centrifugation at 4,000 rpm (3,500×g) for 20 min at 4° C. on a GS-6R table top centrifuge (Beckman). The pellet was resuspended with 2 ml of phage buffer (1 mM $MgSO_4$, 5 mM $MgCl_2$, 80 mM NaCl and 0.1% Gelatin). The phage suspension was extracted with 1 volume of chloroform and further purified by centrifugation on a cesium chloride step gradient as described in Sambrook et al. (1989), using a TLS 55 rotor centrifuged in an Optima TLX ultracentrifuge (Beckman) for 2 h at 28,000 rpm (67,000×g) at 4° C. Banded phage was collected and ultracentrifuged again on an isopycnic cesium chloride gradient (1.45 g/ml) at 40,000 rpm (64,000×g) for 24 h at 4° C. using a TLV rotor (Beckman). The phage was harvested and dialyzed for 4 h at room temperature against 4 L of dialysis buffer consisting of 10 mM NaCl, 50 mM Tris-HCl [pH 8] and 10 mM $MgCl_2$. Phage DNA was prepared from the phage suspension by adding 20 mM EDTA, 50 mg/ml Proteinase K and 0.5% SDS and incubating for 1 h at 65° C., followed by successive extractions with 1 volume of phenol, 1 volume of phenol-chloroform and 1 volume of chloroform. The DNA was then dialyzed overnight at 4° C. against 4 L of TE (10 mM Tris pH 8.0, 1 mM EDTA).

EXAMPLE II

DNA Sequencing of Bacteriophage 77 Genome

Four micrograms of phage DNA was diluted in 200 µl of TE (10 mM Tris, [pH 8.0], 1 mM EDT A) in a 1.5 ml eppendorf tube and sonication was performed (550 Sonic Dismembrator™, Fisher Scientific). Samples were sonicated under an amplitude of 3 µm with bursts of 5 s spaced by 15 s cooling in ice/water for 3 to 4 cycles. The sonicated DNA was then size fractionated by electrophoresis on 1% agarose gels utilizing TAE (1×TAE is: 40 mM Tris-acetate, 1 mM EDTA [pH 8.0]) as the running buffer. Fractions ranging from 1 to 2 kbp were excised from the agarose gel and purified using a commercial DNA extraction system according to the instructions of the manufacturer (Qiagen), with a final elution of 50 µl of 1 mM Tris (pH 8.5).

The ends of the sonicated DNA fragments were repaired with a combination of T4 DNA polymerase and the Klenow fragment of *E. coli* DNA polymerase I, as follows. Reactions were performed in a reaction mixture (final volume, 100 µl) containing sonicated phage DNA, 10 mM Tris-HCl [pH 8.0], 50 mM NaCl, 10 mM $MgCl_2$, 1 mM DTT, 50 µg/ml BSA, 100 µM of each dNTP and 15 units of T4 DNA polymerase (New England Biolabs) for 20 min at 12° C. followed by addition of 12.5 units of Klenow large fragment (New England Biolabs) for 15 min at room temperature. The reaction was stopped by two phenol/chloroform extractions and the DNA was precipitated with ethanol and the final DNA pellet was resuspended in 20 µl of $H_2O$.

Blunt-ended DNA fragments were cloned by ligation directly into the Hinc II site of pKSII+ vector (New England Biolabs) dephosphorylated by treatment with calf intestinal alkaline phosphatase (New England Biolabs)-treated pKS II+ vector (Stratagene). A typical ligation reaction contained 100 ng of vector DNA, 2 to 5 µl of repaired sonicated phage DNA (50–100 ng) in a final volume of 20 µl containing 800 units of T4 DNA ligase (New England Biolabs) and was incubated overnight at 16° C. Transformation and selection of bacterial clones containing recombinant plasmids was performed in *E. coli* DH10β according to standard procedures (Sambrook et al., 1989).

Recombinant clones were picked from agar plates into 96-well plates containing 100 µl LB and 100 µg/ml ampicillin and incubated at 37° C. The presence of phage DNA insert was confirmed by PCR amplification using T3 and T7 primers flanking the Hinc II cloning site of the pKS II+ vector. PCR amplification of foreign insert was performed in a 15 µl reaction volume containing 10 mM Tris (pH 8.3), 50 mM KCl, 1.5 mM $MgCl_2$, 0.02% gelatin, 1 µM primer, 187.5 µM each dNTP, and 0.75 units Taq polymerase (BRL). The thermocycling parameters were as follows: 2 min initial denaturation at 94° C. for 2 min, followed by 20 cycles of 30 sec denaturation at 94° C., 30 sec annealing at 57° C., and 2 min extension at 72° C., followed by a single extension step at 72° C. for 10 min. Clones with insert sizes of 1 to 2 kbp were selected and plasmid DNA was prepared from the selected clones using QIAprep™ spin miniprep kit (Qiagen).

The nucleotide sequence of the extremities of each recombinant clone was determined using an ABI 377-36 automated sequencer with two types of chemistry: ABI prism Big Dye™ primer or ABI prism Big Dye™ terminator cycle sequencing ready reaction kit (Applied Biosystems). To ensure co-linearity of the sequence data and the genome, all regions of phage genome were sequenced at least once from both directions on two separate clones. In areas that this criteria was not initially met, a sequencing primer was selected and phage DNA was used directly as sequencing template employing ABI prism Big Dye™ terminator cycle sequencing ready reaction kit.

EXAMPLE III

Bioinformatic Management of Primary Nucleotide Sequence

Sequence contigs were assembled using Sequencher™ 3.1 software (GeneCodes). To close contig gaps, sequencing primers were selected near the edge of the contigs. Phage DNA was used directly as sequencing template employing ABI prism BIG DYE™ terminator cycle sequencing ready reaction kit. The complete sequence of bacteriophage 77 is shown in Table 1.

A software program was developed and used on the assemble sequence of bacteriophage 77 to identify all putative ORFs larger than 33 codons. Other ORF identification software can also be utilized, preferably programs which allow alternative start codons. The software scans the primary nucleotide sequence starting at nucleotide #1 for an appropriate start codon. Three possible selections can be made for defining the nature of the start codon: I) selection of ATG, II) selection of ATG or GTG, and III) selection of either ATG, GTG, TTG, CTG, ATT, ATC, and ATA. This latter initiation codon set corresponds to the one reported by the NCBI (at the Web site ncbi.nlm.nih.gov/htbin-post/taxonomy/wprintgc?mode=c) for the bacterial genetic code.

When an appropriate start codon is encountered, a counting mechanism is employed to count the number of codons (groups of three nucleotides) between this start codon and the next stop codon downstream of it. If a threshold value of 33 is reached, or exceeded, then the sequence encompassed by these two codons (start and stop codons) is defined as an ORF. This procedure is repeated, each time starting at the next nucleotide following the previous stop codon found, in order to identify all the other putative ORFs. The scan is performed on all three reading frames of both DNA strands of the phage sequence.

Sequence homology (BLAST) searches for each ORF are then carried out using an implementation of BLAST programs, although any of a variety of different sequence comparison and matching programs can be utilized as known to those skilled in the art. Downloaded public databases used for sequence analysis include:

i) non-redundant GenBank (at the ftp site ncbi.nlm.nih.gov/blast/db/nr.Z),
ii) Swissprot (at the ftp site ncbi.nlm.nih.gov/blast/db/swissprot.Z);
iii) vector (at the ftp site ncbi.nlm.nih.gov/blast/db/vector.Z);
iv) pdbaa databases (at the ftp site ncbi.nlm.nih.gov/blast/db/pdbaa.Z);
v) *Staphylococcus aureus* NCTC 8325(at the ftp site ftp.genome.ou.edu/pub/staph/staph-1 k.fa);
vi) *Streptococcus pyogenes* (at the ftp site ftp.genome.ou.edu/pub/strep/strep-1 k.fa);
vii) *Streptococcus pneumoniae* (at the ftp site ftp.tigr.org/pub/data/s_pneumoniae/gsp.contigs. 112197.Z);
viii) *Mycobacterium tuberculosis* CSU#9 (at the ftp site ftp.tigr.org/pub/data/m_tuberculosis/TB_091097.Z) and
ix) *Pseudomonas aeruginosa* (at the Web site genome.washington.edu/pseudo/data.html).

The results of the homology searches performed on the ORFs is shown in Table 4.

EXAMPLE IV

Subcloning of Bacteriophage 77 ORFs into a Staph A Inducible Expression System

Figure 1B:
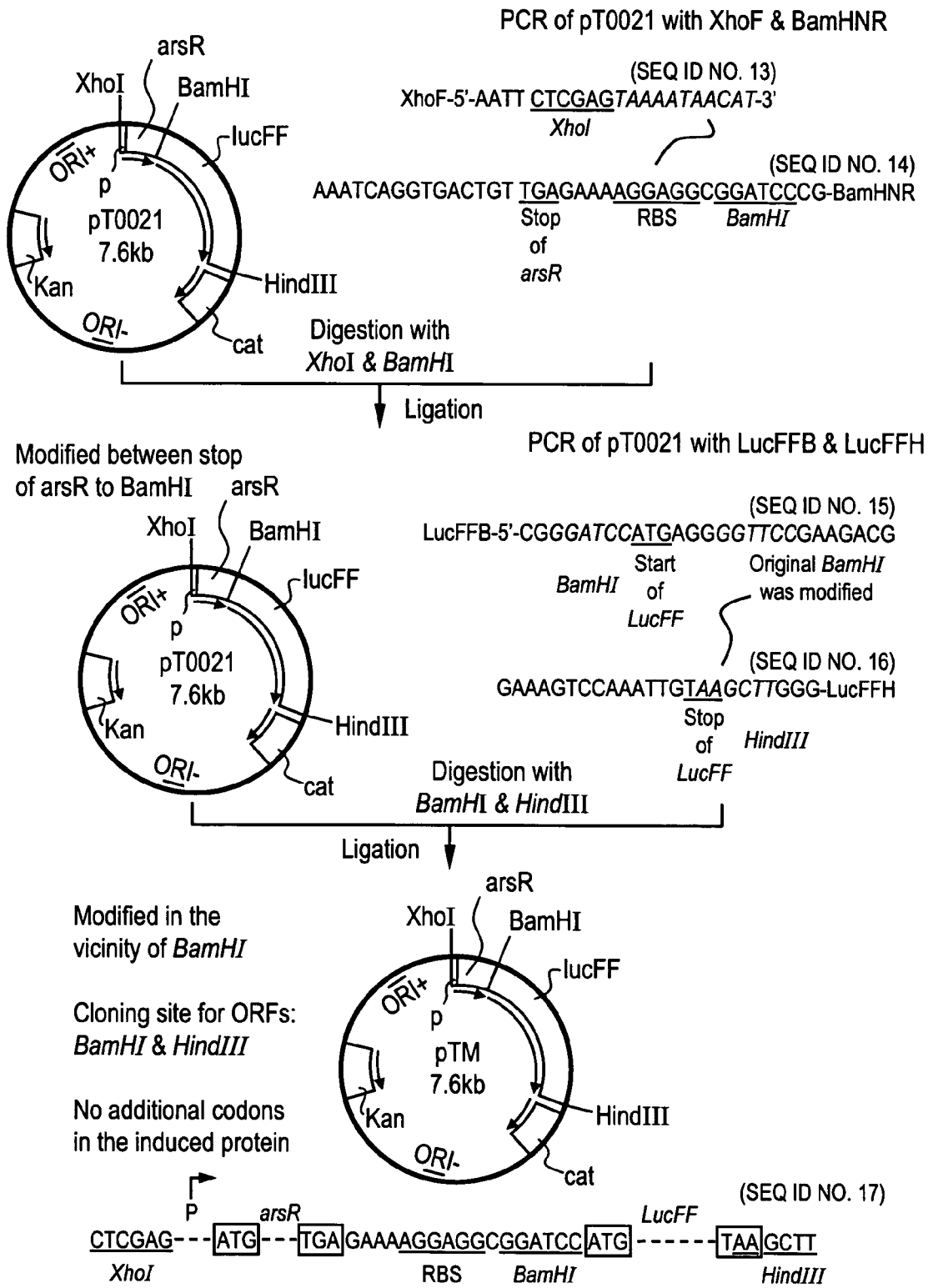
FIG. 1 is a flow schematic showing the manipulations necessary to convert pT0021, an arsenite inducible vector containing the luciferase gene, into pTHA or pTM, two ars inducible vectors. Vector pTHA contains BamH I, Sal I, and Hind III cloning sites and a downstream HA epitope tag. Vector pTM contains Bam HI and Hind III cloning sites and no HA epitope tag.
Figure 2:
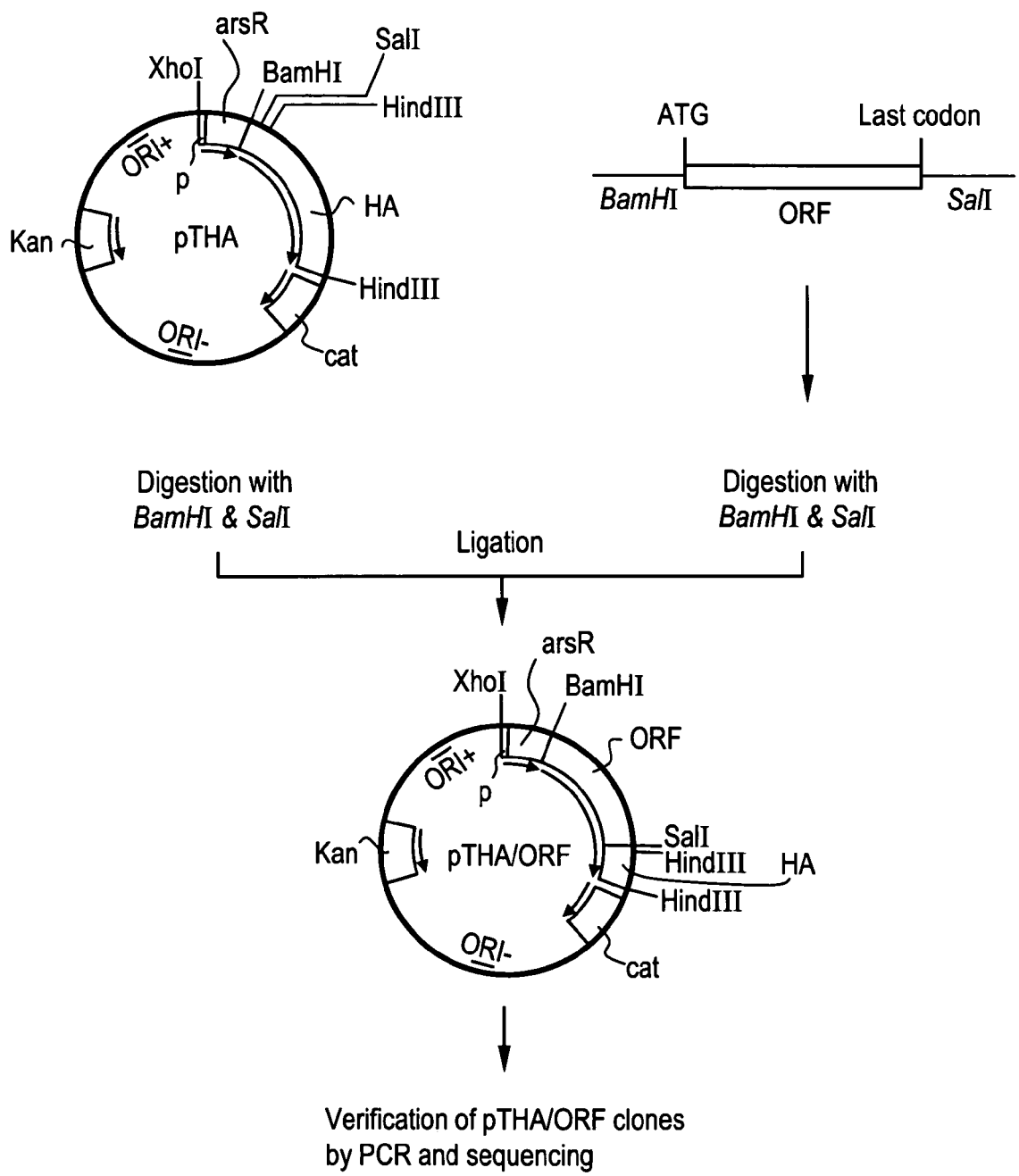
FIG. 2 is a schematic representation of the cloning steps involved to place the DNA segments of any of ORFs 17/ 19/ 43/ 102/ 104/ 182 or other sequences into pTHA to assess inhibitory potential. For subcloning into pTM or pT0021, Individual ORFs were amplified by the PCR using oligonucleotides targeting the ATG and stop codons of the ORFs. Using this strategy, Bam HI and Hind III sites were positioned immediately upstream or downstream, respectively of the start and stop codons of each ORF. Following digestion with Bam HI and Hind III, the PCR fragments were subcloned into the same sites of pT0021 or p™. Clones were verified by PCR and direct sequencing.

The shuttle vector pT0021, in which the firefly luciferase (lucFF) expression is controlled by the ars (arsenite) promoter/operator (Tauriainen et al., 1997), was modified in the following fashion. Two oligonucleotides corresponding to a short antigenic peptide derived from the heamaglutinin protein of influenza virus (HA epitope tag) were synthesized (Field et al., 1988). The sense strand HA tag sequence (with BamHI, SalI and HindIII cloning sites) is: 5'-gatcccggtcgaccaagcttTACCCATACGACGTCCCAGAC-TACGCCAGCTGA-3' (SEQ ID NO. 11) (where upper case letters denote the nucletotide sequence of the HA tag); the antisense strand HA tag sequence (with a HindIII cloning site) is: 5'-agctTCAGCTGGCGTAGTCTGG-GACGTCGTATGGGTAaagcttggtcgaccgg-3' (SEQ ID NO. 12) (where upper case letters denote the sequence of the HA tag). The two HA tag oligonucleotides were annealed and ligated into pT0021 vector which had been digested with BamHI and HindIII. This manipulation resulted in replacement of the lucFF gene by the HA tag. This modified shuttle vector containing the arsenite inducible promoter, the arsR gene, and HA tag was named pTHA. A diagram outlining our modification of pT0021 to generate pTHA is shown in FIG. 1.

Each ORF, encoded by Bacteriophage 77, larger than 33 amino acids and having a Shine-Dalgarno sequence upstream of the initiation codon was selected for functional analysis for bacterial inhibition. In total, 98 ORFs were selected and screened as detailed below. A list of these is presented in Table 5. Each individual ORF, from initiation codon to last codon (excluding the stop codon), was amplified from phage genomic DNA using the polymerase chain reaction (PCR). For PCR amplification of ORFs, each sense strand primer targets the initiation codon and is preceded by a BamHI restriction site ($^{5'}$cgggatcc$^{3'}$) and each antisense oligonucleotide targets the pentultimate codon (the one before the stop codon) of the ORF and is preceded by a Sal I restriction site ($^{5'}$gcgtcgaccg$^{3'}$) (SEQ ID NO. 1). The PCR product of each ORF was gel purified and digested with BamHI and SalI. The digested PCR product was then gel purified using the Qiagen kit as described, ligated into BamHI and SalI digested pTHA vector, and used to transform *E. coli* bacterial strain DH10β(as described above). As a result of this manipulation, the HA tag is set inframe with the ORF and is positioned at the carboxy terminus of each ORF (pTHA/ORF clones). Recombinant pTHA/ORF clones were picked and their insert sizes were confirmed by PCR analysis using primers flanking the cloning site. The names and sequences of the primers that were used for the PCR amplification were: HAF: $^{5'}$TATTATCCAAAACT-TGAACA$^{3'}$ (SEQ ID NO. 2); HAR: $^{5'}$CGGTGGTATATC-CAGTGATT$^{3'}$ (SEQ ID NO. 3). The sequence integrity of cloned ORFs was verified directly by DNA sequencing using primers HAF and HAR. In cases where verification of ORF sequence could not be achieved by one pass with the sequencing primers, additional internal primers were selected and used for sequencing. *Staphylococcus aureus* strain RN4220 (Kreiswirth et al., 1983) was used as a recipient for the expression of recombinant plasmids. Electoporation was performed essentially as previously described (Schenk and Laddaga, 1992). Selection of recombinant clones was performed on Luria-Broth agar (LB-agar) plates containing 30 μg/ml of kanamycin.

For each ORF introduced in the pTHA plasmid, 3 independent transformants were isolated and used to individually inoculate cultures in 5 ml of TSB containing 30 µg/ml kanamycin, followed by growth to saturation (16 hrs at 30° C.). An aliquot of this stationary phase culture was used to generate a frozen glycerol stock of the transformant (stored at −80° C.). The remaining culture was used for plasmid DNA extraction. Bacterial cells were harvested by centrifugation at 3000×g at 22° C. for 5 min. The pellet was resuspended in 200 µl 25% sucrose containing 25 U/ml of lysostaphin and incubated for 15 min at 37° C. Then, 400 µl of alkaline SDS solution (3% SDS, 0.2N NaOH) were added, well mixed and incubated for 7 min at room temperature. After the alkaline SDS treatment, 300 µl of ice-cold 3M sodium acetate pH 4.8 were added, and the mix is immediately spun at 13000 g for 15 min at room temperature. The supernatant was transferred to a new 1.5 ml conical centrifuge tube and 650 µl of isopropanol (stored at room temperature) were added. The mix was then centrifuged at 13,000×g for 5 min. The supernatant fluid was discarded, the pellet washed with 70% ethanol, and resuspended in 320 µl sterile distilled water.

The presence of individual phage 77 ORF DNA inserts in the plasmid was verified by PCR amplification using 1.5 µl transformant miniprep DNA in a PCR with primers flanking the cloning site of ORF in pTHA vector (HAF and HAR). The composition of the PCR reaction and the cycling parameters are identical to those employed for library screening described above.

EXAMPLE V

Functional Assay for Bacterial Inhibitory Activity of Bacteriophage 77 ORFs

The anti-microbial activity of individual phage 77 ORFs was monitored by two growth inhibitory assays, one on solid agar medium, the other in liquid medium. In general, *Staphylococcus* bacteria transformed with expression plasmids containing individual ORFs were grown in normal TSA medium and stored in 19% glycerol. At pre-determined times, arsenite was added to the culture to induce transcription of the phage 77 ORFs cloned immediately downstream from an arsenite-inducible promoter in the pTHA expression plasmid.

The effect of ORF induction on bacterial growth characteristics was then monitored and quantitated. The growth inhibition assay on solid medium was performed by streaking pTHA/ORF containing *S. aureus* transformant onto LB-Kn and TSA-Kn plates containing increasing concentrations of sodium arsenite (0; 2.5; 5; and 7.5 µM). Arsenite is used to induce the expression of cloned DNA in pTHA vector. In parallel, 3 µl of 1/10 and 1/100 dilutions of the frozen cultures of the pTHA/ORF transformants were spotted as single drops onto LB-Kn and TSA-Kn plates containing increasing concentration of sodium arsenite (0; 2.5; 5; and 7.5 µM). The plates were then incubated 16 hrs at 37° C., and the effect of arsenite-induced ORF expression on bacterial growth was monitored and quantitated by comparing the extent to that seen in control plates. As positive controls for growth inhibition, the holin/lysin genes of the *Sthaphylococcus aureus* phage Twort (Loessner et al., 1998) was subcloned into the pTHA ars inducible vector and used.

For the growth inhibition assay in liquid medium, stationary phase cultures were prepared by inoculating 2.5 ml TSB-Kn with frozen *S. aureus* RN4220 transformants containing phage 77 ORFs cloned in pTHA vector followed by incubation for 16 hrs at 37° C. These cultures were then diluted 1/100 in the same medium, and the bacteria were allowed to grow for 2 hrs at 37° C. to reach early log phase. 150 µl of such culture were then mixed with 2.35 ml TSB-Kn medium with or without arsenite (the final concentration of arsenite in the medium was 0 or 5 µM arsenite). After 3.5 hrs incubation at 37° C. with shaking at 250 rpm, 100 µl of bacterial culture was removed from each tube for $OD_{565}$ measurement. Serial ten-fold dilutions of the culture in buffered saline solution (0.85% NaCl) were then spotted onto TSB-Kn plates. The plates were incubated at 37° C. 16 hrs and the number of surviving colonies counted the following day. The growth inhibitory property of individual ORFs was then quantitated by comparing CFU numbers under normal or arsenite-induction conditions. Inhibition results are shown in FIGS. 5 and 5.

REFERENCES

Cohen, M. L. (1992). Science 257: 1050–1055.
Rusterholtz, K., and Pohlschroder, M. (1999). Cell 96, 469–470.
Ackermann, H.-W. and DuBow, M. S. (1987). Viruses of Prokaryotes. CRC Press. Volumes 1 and 2.
Durfee, T., Becherer, K., Chen, P.-L., Yeh, S.-H., Yang, Y., Kilburn, A. E., Lee, W.-H., and Elledge, S. J. (1993). Genes & Dev. 7: 555–569.
Sopta, M., Carthew, R. W., and Greenblatt, J. (1995) J. Biol. Chem. 260: 10353–10369.
Qin, J., Fenyo, D., Zhao, Y., Hall, W.W., Chao, D. M., Wilson, C. J., Young, R. A. and Chait, B. T. (1997). Anal. Chem. 69: 3995–4001.
Sambrook, J., Fritsch, E. F. and Maniatis, T (1989). Molecular cloning: A laboratory Manual. Cold Spring Harbor Laboratory, New York. Cold Spring Harbor Laboratory Press.
Swanström, M. and Adams, M. H. (1951). Agar layer method for production of high titer phage stocks. Proc. Soc. Exptl. Biol. & Med. 78: 372–375.
Tauriainen, S., Karp, M., Chang, W and Virta, M. (1997). Recombinant luminescent bacteria for measuring bioavailable arsenite and antimonite. Appl. Environ. Microbiol. 63:4456–4461.
Field, J., Nikawa, J.-I., Broek, D., MacDonald, B., Rodgers, L., Wilson, I. A., Lerner, R. A., and Wigler, M. (1988). Purification of a RAS-responsive adenylyl cyclase complex from *Saccharomyces cerevisiae* by use of an epitope addition method. Mol. Cell. Biol. 8: 2159–2165.
Kreiswirth, B N., Lofdahl, S., Belley, M J., O'Reilly, M., Shlievert, P M., Bergdoll, M S. and Novicks, R P. 1983. Nature #305: 709–712.
Schenk, S. and Laddaga, R A. 1992. FEMS Microbiology Letters #94: 133–138.
Loessner, M J., Gaeng, S., Wendlinger, G., Maier, S K. and Scherer, S. 1998. FEMS Microbiology Letters #162: 265–274.

All patents and publications mentioned in the specification are indicative of the levels of skill of those skilled in the art to which the invention pertains. All references cited in this disclosure are incorporated by reference to the same extent as if each reference had been incorporated by reference in its entirety individually.

One skilled in the art would readily appreciate that the present invention is well adapted to carry out the objects and obtain the ends and advantages mentioned, as well as those inherent therein. The specific methods and compositions described herein as presently representative of preferred embodiments are exemplary and are not intended as limitations on the scope of the invention. Changes therein and other uses will occur to those skilled in the art which are encompassed within the spirit of the invention are defined by the scope of the claims.

It will be readily apparent to one skilled in the art that varying substitutions and modifications may be made to the invention disclosed herein without departing from the scope and spirit of the invention. For example, those skilled in the art will recognize that the invention may suitably be practiced using a variety of different expression vectors and sequencing methods within the general descriptions provided.

The invention illustratively described herein suitably may be practiced in the absence of any element or elements, limitation or limitations which is not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is not. intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group. For example, if there are alternatives A, B, and C, all of the following possibilities are included: A separately, B separately, C separately, A and B, A and C, B and C, and A and B and C.

Thus, additional embodiments are within the scope of the invention and within the following claims.

What is claimed is:

1. An isolated, purified, or enriched nucleic acid sequence at least 90 nucleotides in length, wherein said sequence is at least 95% identical to a *Staphylococcus aureus* bacteriophage 77 open reading frame (ORF) selected from the group consisting of ORF 17 (SEQ ID NO: 4), ORF 19 (SEQ ID NO: 5), ORF 43 (SEQ ID NO: 6), ORF 102 (SEQ ID NO: 7), ORF 104 (SEQ ID NO: 8), and ORF 182 (SEQ ID NO: 9).

2. A recombinant expression vector comprising a nucleic acid sequence at least 90 nucleotides in length, wherein said sequence is at least 95% identical to a *Staphylococcus aureus* bacteriophage 77 open reading frame (ORF) selected from the group consisting of ORF 17 (SEQ ID NO: 4), ORF 19 (SEQ ID NO: 5), ORF 43 (SEQ ID NO: 6), ORF 102 (SEQ ID NO: 7), ORF 104 (SEQ ID NO: 8), and ORF 182 (SEQ ID NO: 9).

3. A cell comprising an expression vector, wherein said vector comprises a nucleic acid sequence at least 90 nucleotides in length, wherein said sequence is at least 95% identical to a *Staphylococcus aureus* bacteriophage 77 open reading frame (ORF) selected from the group consisting or ORF 17 (SEQ ID NO: 4), ORF 19 (SEQ ID NO: 5), ORF 43 (SEQ ID NO: 6), ORF 102 (SEQ ID NO: 7), ORF 104 (SEQ ID NO: 8), and ORF 182 (SEQ ID NO: 9).

4. The nucleic acid sequence of claim 1, wherein said open reading frame is open reading frame 17 (SEQ ID NO. 4).

5. The nucleic acid sequence of claim 1, wherein said open reading frame is open reading frame 19 (SEQ ID NO. 5).

6. The nucleic acid sequence of claim 1, wherein said open reading frame is open reading frame 43 (SEQ ID NO. 6).

7. The nucleic acid sequence of claim 1, wherein said open reading frame is open reading frame 102 (SEQ ID NO. 7).

8. The nucleic acid sequence of claim 1, wherein said open reading frame is open reading frame 104 (SEQ ID NO. 8).

9. The nucleic acid sequence of claim 1, wherein said open reading frame is open reading frame 182 (SEQ ID NO. 9).

10. The nucleic acid sequence of claim 1, wherein said nucleic acid is at least 120 nucleotides in length.

11. The nucleic acid sequence of claim 1, wherein said nucleic acid sequence is transcriptionally linked with regulatory sequences enabling induction of expression of said sequence.

12. The vector of claim 2, wherein expression of said nucleic acid sequence is inducible.

13. The vector of claim 12, wherein said expression is inducible using arsenite inducible operator and promoter.

14. The cell of claim 3, wherein expression from said nucleic acid sequence in said expression vector is inducible.

15. The cell of claim 14, wherein said expression is inducible using arsenite inducible operator and promoter.

16. A method for preparing a polypeptide encoded by nucleic acid sequence which is at least 90 nucleotides in length, wherein said sequence is at least 95% identical to a *Staphylococcus aureus* bacteriophage 77 open reading frame (ORF) selected from the group consisting of ORF 17 (SEQ ID NO: 4), ORF 19 (SEQ ID NO: 5), ORF 43 (SEQ ID NO: 6), ORF 102 (SEQ ID NO: 7), ORF 104 (SEQ ID NO: 8), and ORF 182 (SEQ ID NO: 9), said method comprising culturing a cell according to claim 13 under conditions promoting expression of said polypeptide and recovering the polypeptide so expressed.

* * * * *